(12) United States Patent
Thompson et al.

(10) Patent No.: US 10,084,880 B2
(45) Date of Patent: Sep. 25, 2018

(54) SOCIAL MEDIA NETWORKING BASED ON PHYSIOLOGIC INFORMATION

(71) Applicant: Proteus Digital Health, Inc., Redwood City, CA (US)

(72) Inventors: Andrew Thompson, Portola Valley, CA (US); Todd Thompson, San Jose, CA (US); Yashar Behzadi, Anaheim, CA (US); Danielle Cojuangco Abraham, San Francisco, CA (US); Robert Duck, San Francisco, CA (US); Arna Ionescu, San Francisco, CA (US); Ray Lee, San Francisco, CA (US); Robin Suchan, Albany, CA (US); William Turner, San Francisco, CA (US); Veeraperumanallu Muralidharan, Santa Clara, CA (US); Erika Karplus, Silverthorne, CO (US); George Savage, Portola Valley, CA (US)

(73) Assignee: PROTEUS DIGITAL HEALTH, INC., Redwood City, CA (US)

( * ) Notice: Subject to any disclaimer, the term of this patent is extended or adjusted under 35 U.S.C. 154(b) by 462 days.

(21) Appl. No.: 14/532,786

(22) Filed: Nov. 4, 2014

(65) Prior Publication Data
US 2015/0127737 A1 May 7, 2015

Related U.S. Application Data

(60) Provisional application No. 61/899,704, filed on Nov. 4, 2013.

(51) Int. Cl.
*H04L 29/08* (2006.01)
*G06F 19/00* (2018.01)
(Continued)

(52) U.S. Cl.
CPC ........ *H04L 67/306* (2013.01); *G06F 19/3418* (2013.01); *G16H 10/60* (2018.01); *H04W 4/21* (2018.02); *H04W 4/80* (2018.02)

(58) Field of Classification Search
CPC ...... G06F 19/322; G06F 19/3418; G01J 3/02; G01J 3/0202; G01J 3/0208; G01J 3/0256;
(Continued)

(56) References Cited

U.S. PATENT DOCUMENTS

| 1,548,459 A | 8/1925 | Hammer |
| 2,587,158 A | 2/1952 | Hofberg |

(Continued)

FOREIGN PATENT DOCUMENTS

| CA | 2953847 | 11/2006 |
| CN | 1588649 | 3/2005 |

(Continued)

OTHER PUBLICATIONS

Greene, "Medicaid Efforts to Incentivize Healthy Behaviours", Center for Health Care Strategies, Inc., Resource Paper, Jul. 2007.
(Continued)

*Primary Examiner* — Michael C Lai
(74) *Attorney, Agent, or Firm* — K&L Gates LLP

(57) ABSTRACT

A method comprising receiving physiologic information at a social-networking system from a body-associated personal communicator is disclosed. A social-networking system configured to receive physiological information from a body-associated personal communicator and a body-associated personal communicator configured to receive physiologic information and communicate the physiologic information to a social-networking system also are disclosed.

20 Claims, 14 Drawing Sheets

(51) Int. Cl.
  *G16H 10/60* (2018.01)
  *H04W 4/21* (2018.01)
  *H04W 4/80* (2018.01)

(58) Field of Classification Search
  CPC .......... G01J 3/0259; G01J 3/0262; G01J 3/18;
           G01J 3/2803; H04L 67/306; H04W
                      4/008; H04W 4/206
  USPC ........................................................ 709/204
  See application file for complete search history.

(56) References Cited

U.S. PATENT DOCUMENTS

| | | |
|---|---|---|
| 2,973,555 A | 3/1961 | Schwepke |
| 3,048,526 A | 8/1962 | Boswell |
| 3,079,824 A | 3/1963 | Schott |
| 3,096,248 A | 7/1963 | Rudzki |
| 3,176,399 A | 4/1965 | Marino et al. |
| 3,340,866 A | 9/1967 | Noller |
| 3,345,989 A | 10/1967 | Reynolds |
| 3,409,721 A | 11/1968 | Applezweig |
| 3,419,736 A | 12/1968 | Walsh |
| 3,589,943 A | 6/1971 | Grubb et al. |
| 3,607,788 A | 9/1971 | Adolph |
| 3,628,669 A | 12/1971 | McKinnis et al. |
| 3,642,008 A | 2/1972 | Bolduc |
| 3,679,480 A | 7/1972 | Brown et al. |
| 3,682,160 A | 8/1972 | Murata |
| 3,719,183 A | 3/1973 | Schwartz |
| 3,727,616 A | 4/1973 | Lenzkes |
| 3,799,802 A | 3/1974 | Schneble, Jr. et al. |
| 3,825,016 A | 7/1974 | Lale et al. |
| 3,828,766 A | 8/1974 | Krasnow |
| 3,837,339 A | 9/1974 | Aisenberg et al. |
| 3,849,041 A | 11/1974 | Knapp |
| 3,893,111 A | 7/1975 | Cotter |
| 3,944,064 A | 3/1976 | Bashaw et al. |
| 3,967,202 A | 6/1976 | Batz |
| 3,989,050 A | 11/1976 | Buchalter |
| 4,017,856 A | 4/1977 | Wiegand |
| 4,055,178 A | 10/1977 | Harrigan |
| 4,062,750 A | 12/1977 | Butler |
| 4,067,014 A | 1/1978 | Wheeler et al. |
| 4,077,397 A | 3/1978 | Ellis |
| 4,077,398 A | 3/1978 | Ellis |
| 4,082,087 A | 4/1978 | Howson |
| 4,090,752 A | 5/1978 | Long |
| 4,105,023 A | 8/1978 | Merchese et al. |
| 4,106,348 A | 8/1978 | Auphan |
| 4,121,573 A | 10/1978 | Crovella et al. |
| 4,129,125 A | 12/1978 | Lester |
| 4,133,730 A | 1/1979 | DuBois et al. |
| 4,139,589 A | 2/1979 | Beringer et al. |
| 4,141,349 A | 2/1979 | Ory et al. |
| 4,143,770 A | 3/1979 | Grimmell et al. |
| 4,149,168 A | 4/1979 | Hose |
| 4,166,453 A | 9/1979 | McClelland |
| 4,185,172 A | 1/1980 | Melindo et al. |
| 4,239,046 A | 12/1980 | Ong |
| 4,251,795 A | 2/1981 | Shibasaki et al. |
| 4,269,189 A | 5/1981 | Abraham |
| 4,281,664 A | 8/1981 | Duggan |
| 4,331,654 A | 5/1982 | Morris |
| 4,333,150 A | 6/1982 | Matty et al. |
| 4,345,588 A | 8/1982 | Widder et al. |
| 4,418,697 A | 12/1983 | Tama |
| 4,425,117 A | 1/1984 | Hugemann |
| 4,439,196 A | 3/1984 | Higuchi |
| 4,494,950 A | 1/1985 | Fischell |
| 4,513,385 A | 4/1985 | Muir |
| 4,526,474 A | 7/1985 | Simon |
| 4,547,391 A | 10/1985 | Jenkins |
| 4,559,950 A | 12/1985 | Vaughan |
| 4,564,363 A | 1/1986 | Bagnall et al. |
| 4,578,061 A | 3/1986 | Lemelson |
| 4,618,533 A | 10/1986 | Steuck |
| 4,635,641 A | 1/1987 | Hoffman |
| 4,654,165 A | 3/1987 | Eisenber |
| 4,663,250 A | 5/1987 | Ong et al. |
| 4,669,479 A | 6/1987 | Dunseath |
| 4,681,111 A | 7/1987 | Silvian |
| 4,687,660 A | 8/1987 | Baker et al. |
| 4,725,997 A | 2/1988 | Urquhart et al. |
| 4,749,575 A | 6/1988 | Rotman et al. |
| 4,763,659 A | 8/1988 | Dunseath |
| 4,767,627 A | 8/1988 | Caldwell et al. |
| 4,775,536 A | 10/1988 | Patell |
| 4,784,162 A | 11/1988 | Ricks |
| 4,793,825 A | 12/1988 | Benjamin et al. |
| 4,809,705 A | 3/1989 | Ascher |
| 4,814,181 A | 3/1989 | Jordan et al. |
| 4,835,373 A | 5/1989 | Adams et al. |
| 4,844,076 A | 7/1989 | Lesho |
| 4,847,090 A | 7/1989 | Della Posta et al. |
| 4,858,617 A | 8/1989 | Sanders |
| 4,871,974 A | 10/1989 | Davis et al. |
| 4,876,093 A | 10/1989 | Theeuwes et al. |
| 4,896,261 A | 1/1990 | Nolan |
| 4,975,230 A | 12/1990 | Pinkhasov |
| 4,987,897 A | 1/1991 | Funke |
| 5,000,957 A | 3/1991 | Eckenhoff et al. |
| 5,016,634 A | 5/1991 | Vock et al. |
| 5,018,335 A | 5/1991 | Yamamoto et al. |
| 5,079,006 A | 1/1992 | Urquhart |
| 5,110,441 A | 5/1992 | Kinlen et al. |
| 5,113,859 A | 5/1992 | Funke |
| 5,160,885 A | 11/1992 | Hannam et al. |
| 5,167,626 A | 12/1992 | Casper |
| 5,176,626 A | 1/1993 | Soehendra |
| 5,179,578 A | 1/1993 | Ishizu |
| 5,187,723 A | 2/1993 | Mueller |
| 5,213,738 A | 5/1993 | Hampton et al. |
| 5,218,343 A | 6/1993 | Stobbe et al. |
| 5,232,382 A | 8/1993 | Barnick |
| 5,232,383 A | 8/1993 | Barnick |
| 5,245,332 A | 9/1993 | Katzenstein et al. |
| 5,261,402 A | 11/1993 | DiSabito |
| 5,263,481 A | 11/1993 | Axelgaard et al. |
| 5,273,066 A | 12/1993 | Graham et al. |
| 5,276,710 A | 1/1994 | Iwasaki |
| 5,279,607 A | 1/1994 | Schentag et al. |
| 5,281,287 A | 1/1994 | Lloyd |
| 5,283,136 A | 2/1994 | Peled et al. |
| 5,288,564 A | 2/1994 | Klein |
| 5,305,745 A | 4/1994 | Zacouto |
| 5,318,557 A | 6/1994 | Gross |
| 5,331,953 A | 7/1994 | Andersson et al. |
| 5,394,882 A | 3/1995 | Mawhinney |
| 5,395,366 A | 3/1995 | D'Andrea et al. |
| 5,411,535 A | 5/1995 | Fujii et al. |
| 5,412,372 A | 5/1995 | Parkhurst et al. |
| 5,428,961 A | 7/1995 | Sakakibara |
| 5,436,091 A | 7/1995 | Shackle et al. |
| 5,443,461 A | 8/1995 | Atkinson et al. |
| 5,443,843 A | 8/1995 | Curatolo et al. |
| 5,458,141 A | 10/1995 | Neil et al. |
| 5,458,994 A | 10/1995 | Nesselbeck et al. |
| 5,468,222 A | 11/1995 | Altchuler |
| 5,485,841 A | 1/1996 | Watkin et al. |
| 5,506,248 A | 4/1996 | Nikfar et al. |
| 5,511,548 A | 4/1996 | Riazzi et al. |
| 5,551,020 A | 8/1996 | Flax et al. |
| 5,551,953 A | 9/1996 | Lattin et al. |
| 5,567,210 A | 10/1996 | Bates et al. |
| 5,596,302 A | 1/1997 | Mastrocola et al. |
| D377,983 S | 2/1997 | Sabri et al. |
| 5,600,548 A | 2/1997 | Nguyen et al. |
| 5,603,363 A | 2/1997 | Nelson |
| 5,623,520 A | 4/1997 | Kaiser |
| 5,634,466 A | 6/1997 | Gruner |
| 5,634,468 A | 6/1997 | Platt |
| 5,638,406 A | 6/1997 | Sogabe |
| 5,645,063 A | 7/1997 | Straka et al. |
| 5,659,247 A | 8/1997 | Clements |

(56) References Cited

U.S. PATENT DOCUMENTS

| | | |
|---|---|---|
| 5,703,463 A | 12/1997 | Smith |
| 5,705,189 A | 1/1998 | Lehmann et al. |
| 5,720,771 A | 2/1998 | Snell |
| 5,724,432 A | 3/1998 | Bouvet et al. |
| 5,738,708 A | 4/1998 | Peachey et al. |
| 5,740,811 A | 4/1998 | Hedberg |
| 5,757,326 A | 5/1998 | Koyama et al. |
| 5,772,575 A | 6/1998 | Lesinski et al. |
| 5,792,048 A | 8/1998 | Schaefer |
| 5,802,467 A | 9/1998 | Salazar |
| 5,833,716 A | 11/1998 | Bar-Or |
| 5,836,474 A | 11/1998 | Wessberg |
| 5,842,324 A | 12/1998 | Grosskopf et al. |
| 5,845,265 A | 12/1998 | Woolston |
| 5,862,803 A | 1/1999 | Besson |
| 5,862,808 A | 1/1999 | Albarello |
| 5,868,136 A | 2/1999 | Fox |
| 5,914,132 A | 6/1999 | Kelm et al. |
| 5,914,701 A | 6/1999 | Gersheneld et al. |
| 5,917,346 A | 6/1999 | Gord |
| 5,921,925 A | 7/1999 | Cartmell et al. |
| 5,925,030 A | 7/1999 | Gross et al. |
| 5,925,066 A | 7/1999 | Kroll et al. |
| 5,957,854 A | 9/1999 | Besson et al. |
| 5,963,132 A | 10/1999 | Yoakum et al. |
| 5,965,629 A | 10/1999 | Jung et al. |
| 5,974,124 A | 10/1999 | Schlueter, Jr. et al. |
| 5,981,166 A | 11/1999 | Mandecki |
| 5,999,846 A | 12/1999 | Pardey et al. |
| 6,009,350 A | 12/1999 | Renken |
| 6,018,229 A | 1/2000 | Mitchell et al. |
| 6,023,631 A | 2/2000 | Cartmell et al. |
| 6,038,464 A | 3/2000 | Axelgaard et al. |
| 6,042,710 A | 3/2000 | Dubrow |
| 6,047,203 A | 4/2000 | Sackner |
| 6,068,465 A | 5/2000 | Wilson |
| 6,068,589 A | 5/2000 | Neukermans |
| 6,076,016 A | 6/2000 | Feierbach et al. |
| 6,081,734 A | 6/2000 | Batz |
| 6,083,248 A | 7/2000 | Thompson |
| 6,090,489 A | 7/2000 | Hayakawa et al. |
| 6,091,975 A | 7/2000 | Daddona et al. |
| 6,095,985 A | 8/2000 | Raymond et al. |
| 6,099,482 A | 8/2000 | Brune et al. |
| 6,115,636 A | 9/2000 | Ryan |
| 6,117,077 A | 9/2000 | Del Mar et al. |
| 6,122,351 A | 9/2000 | Schlueter, Jr. et al. |
| 6,141,592 A | 10/2000 | Pauly |
| 6,149,940 A | 11/2000 | Maggi et al. |
| 6,151,353 A | 11/2000 | Harrison et al. |
| 6,200,265 B1 | 3/2001 | Walsh et al. |
| 6,200,625 B1 | 3/2001 | Beckett |
| 6,204,764 B1 | 3/2001 | Maloney |
| 6,206,702 B1 | 3/2001 | Hayden et al. |
| 6,217,744 B1 | 4/2001 | Crosby |
| 6,231,593 B1 | 5/2001 | Meserol |
| 6,238,338 B1 | 5/2001 | DeLuca et al. |
| 6,245,057 B1 | 6/2001 | Sieben et al. |
| 6,269,058 B1 | 7/2001 | Yamanoi et al. |
| 6,275,476 B1 | 8/2001 | Wood |
| 6,285,897 B1 | 9/2001 | Kilcoyne et al. |
| 6,287,252 B1 | 9/2001 | Lugo |
| 6,288,629 B1 | 9/2001 | Cofino et al. |
| 6,289,238 B1 | 9/2001 | Besson et al. |
| 6,301,298 B1 | 10/2001 | Kuntz et al. |
| 6,315,719 B1 | 11/2001 | Rode et al. |
| 6,317,714 B1 | 11/2001 | Del Castillo |
| 6,342,774 B1 | 1/2002 | Kreisinger et al. |
| 6,344,824 B1 | 2/2002 | Takasugi et al. |
| 6,358,202 B1 | 3/2002 | Arent |
| 6,364,834 B1 | 4/2002 | Reuss |
| 6,366,206 B1 | 4/2002 | Ishikawa et al. |
| 6,368,190 B1 | 4/2002 | Easter et al. |
| 6,371,927 B1 | 4/2002 | Brune |
| 6,374,670 B1 | 4/2002 | Spelman |
| 6,380,858 B1 | 4/2002 | Yarin et al. |
| 6,390,088 B1 | 5/2002 | Noehl et al. |
| 6,394,953 B1 | 5/2002 | Devlin et al. |
| 6,394,997 B1 | 5/2002 | Lemelson |
| 6,409,674 B1 | 6/2002 | Brockway et al. |
| 6,411,567 B1 | 6/2002 | Niemiec et al. |
| 6,426,863 B1 | 7/2002 | Munshi |
| 6,432,292 B1 | 8/2002 | Pinto et al. |
| 6,440,069 B1 | 8/2002 | Raymond et al. |
| 6,441,747 B1 | 8/2002 | Khair |
| 6,453,199 B1 | 9/2002 | Kobozev |
| 6,477,424 B1 | 11/2002 | Thompson et al. |
| 6,482,156 B2 | 11/2002 | Lliff |
| 6,494,829 B1 | 12/2002 | New et al. |
| 6,496,705 B1 | 12/2002 | Ng et al. |
| 6,505,077 B1 | 1/2003 | Kast et al. |
| 6,525,996 B1 | 2/2003 | Miyazawa |
| 6,526,315 B1 | 2/2003 | Inagawa |
| 6,531,026 B1 | 3/2003 | Takeichi et al. |
| 6,544,174 B2 | 4/2003 | West |
| 6,547,994 B1 | 4/2003 | Monkhouse et al. |
| 6,564,079 B1 | 5/2003 | Cory |
| 6,567,685 B2 | 5/2003 | Takamori et al. |
| 6,572,636 B1 | 6/2003 | Hagen et al. |
| 6,574,425 B1 | 6/2003 | Weiss et al. |
| 6,577,893 B1 | 6/2003 | Besson et al. |
| 6,579,231 B1 | 6/2003 | Phipps |
| 6,595,929 B2 | 7/2003 | Stivoric |
| 6,599,284 B2 | 7/2003 | Faour et al. |
| 6,602,518 B2 | 8/2003 | Seielstad et al. |
| 6,605,038 B1 | 8/2003 | Teller |
| 6,605,046 B1 | 8/2003 | Del Mar |
| 6,609,018 B2 | 8/2003 | Cory |
| 6,612,984 B1 | 9/2003 | Kerr |
| 6,632,175 B1 | 10/2003 | Marshall |
| 6,632,216 B2 | 10/2003 | Houzego et al. |
| 6,635,279 B2 | 10/2003 | Kolter et al. |
| 6,638,231 B2 | 10/2003 | Govari et al. |
| 6,643,541 B2 | 11/2003 | Mok et al. |
| 6,650,718 B1 | 11/2003 | Fujimura et al. |
| 6,654,638 B1 | 11/2003 | Sweeney |
| 6,663,846 B1 | 12/2003 | McCombs |
| 6,673,474 B2 | 1/2004 | Yamamoto |
| 6,679,830 B2 | 1/2004 | Kolarovic et al. |
| 6,680,923 B1 | 1/2004 | Leon |
| 6,683,493 B1 | 1/2004 | Fujimora et al. |
| 6,689,117 B2 | 2/2004 | Sweeney et al. |
| 6,694,161 B2 | 2/2004 | Mehrotra |
| 6,704,602 B2 | 3/2004 | Berg et al. |
| 6,720,923 B1 | 4/2004 | Hayward et al. |
| 6,738,671 B2 | 5/2004 | Christophersom et al. |
| 6,740,033 B1 | 5/2004 | Olejniczak et al. |
| 6,745,082 B2 | 6/2004 | Axelgaard et al. |
| 6,755,783 B2 | 6/2004 | Cosentino |
| 6,757,523 B2 | 6/2004 | Fry |
| 6,759,968 B2 | 7/2004 | Zierolf |
| 6,767,200 B2 | 7/2004 | Sowden et al. |
| 6,771,174 B2 | 8/2004 | Broas |
| 6,773,429 B2 | 8/2004 | Sheppard et al. |
| 6,800,060 B2 | 10/2004 | Marshall |
| 6,801,137 B2 | 10/2004 | Eggers et al. |
| 6,804,558 B2 | 10/2004 | Haller et al. |
| 6,814,706 B2 | 11/2004 | Barton et al. |
| 6,816,794 B2 | 11/2004 | Alvi |
| 6,822,554 B2 | 11/2004 | Vrijens et al. |
| 6,824,512 B2 | 11/2004 | Warkentin et al. |
| 6,836,862 B1 | 12/2004 | Erekson et al. |
| 6,839,659 B2 | 1/2005 | Tarassenko et al. |
| 6,840,904 B2 | 1/2005 | Goldberg |
| 6,842,636 B2 | 1/2005 | Perrault |
| 6,845,272 B1 | 1/2005 | Thomsen |
| 6,856,832 B1 | 2/2005 | Matsumura et al. |
| 6,864,780 B2 | 3/2005 | Doi |
| 6,879,810 B2 | 4/2005 | Bouet |
| 6,882,881 B1 | 4/2005 | Lesser et al. |
| 6,888,337 B2 | 5/2005 | Sawyers |
| 6,889,165 B2 | 5/2005 | Lind et al. |
| 6,897,788 B2 | 5/2005 | Khair et al. |
| 6,909,878 B2 | 6/2005 | Haller |

(56) References Cited

U.S. PATENT DOCUMENTS

| | | |
|---|---|---|
| 6,922,592 B2 | 7/2005 | Thompson et al. |
| 6,928,370 B2 | 8/2005 | Anuzis et al. |
| 6,929,636 B1 | 8/2005 | Von Alten |
| 6,937,150 B2 | 8/2005 | Medema |
| 6,939,292 B2 | 9/2005 | Mizuno |
| 6,942,616 B2 | 9/2005 | Kerr |
| 6,946,156 B2 | 9/2005 | Bunick |
| 6,951,536 B2 | 10/2005 | Yokoi |
| 6,956,917 B2 | 10/2005 | Lenosky |
| 6,957,107 B2 | 10/2005 | Rogers et al. |
| 6,958,603 B2 | 10/2005 | Kondo |
| 6,959,929 B2 | 11/2005 | Pugnet et al. |
| 6,960,617 B2 | 11/2005 | Omidian et al. |
| 6,961,601 B2 | 11/2005 | Mathews et al. |
| 6,968,153 B1 | 11/2005 | Heinonen |
| 6,977,511 B2 | 12/2005 | Patel et al. |
| 6,982,094 B2 | 1/2006 | Sowden |
| 6,987,965 B2 | 1/2006 | Ng et al. |
| 6,990,082 B1 | 1/2006 | Zehavi et al. |
| 7,002,476 B2 | 2/2006 | Rapchak |
| 7,004,395 B2 | 2/2006 | Koenck |
| 7,009,634 B2 | 3/2006 | Iddan et al. |
| 7,009,946 B1 | 3/2006 | Kardach |
| 7,013,162 B2 | 3/2006 | Gorsuch |
| 7,016,648 B2 | 3/2006 | Haller |
| 7,020,508 B2 | 3/2006 | Stivoric |
| 7,023,940 B2 | 4/2006 | Nakamura et al. |
| 7,024,248 B2 | 4/2006 | Penner et al. |
| 7,031,745 B2 | 4/2006 | Shen |
| 7,031,857 B2 | 4/2006 | Tarassenko et al. |
| 7,039,453 B2 | 5/2006 | Mullick |
| 7,044,911 B2 | 5/2006 | Drinan et al. |
| 7,046,649 B2 | 5/2006 | Awater et al. |
| 7,050,419 B2 | 5/2006 | Azenkot et al. |
| 7,061,236 B2 | 6/2006 | Britton |
| 7,062,308 B1 | 6/2006 | Jackson |
| 7,076,437 B1 | 7/2006 | Levy |
| 7,081,693 B2 | 7/2006 | Hamel et al. |
| 7,083,578 B2 | 8/2006 | Lewkowicz |
| 7,091,726 B2 | 8/2006 | Sano et al. |
| 7,116,252 B2 | 10/2006 | Teraguchi |
| 7,118,531 B2 | 10/2006 | Krill |
| 7,122,143 B2 | 10/2006 | Sowden et al. |
| 7,125,382 B2 | 10/2006 | Zhou et al. |
| 7,127,300 B2 | 10/2006 | Mazar et al. |
| 7,139,332 B2 | 11/2006 | Yu et al. |
| 7,146,228 B2 | 12/2006 | Nielsen |
| 7,146,449 B2 | 12/2006 | Do et al. |
| 7,149,581 B2 | 12/2006 | Goedeke et al. |
| 7,154,071 B2 | 12/2006 | Sattler et al. |
| 7,154,916 B2 | 12/2006 | Soloff |
| 7,155,232 B2 | 12/2006 | Godfrey et al. |
| 7,160,258 B2 | 1/2007 | Imran |
| 7,161,484 B2 | 1/2007 | Tsoukalis |
| 7,164,942 B2 | 1/2007 | Avrahami |
| 7,171,166 B2 | 1/2007 | Ng et al. |
| 7,171,177 B2 | 1/2007 | Park et al. |
| 7,171,259 B2 | 1/2007 | Rytky |
| 7,176,784 B2 | 2/2007 | Gilbert et al. |
| 7,187,960 B2 | 3/2007 | Abreu |
| 7,188,199 B2 | 3/2007 | Leung et al. |
| 7,188,767 B2 | 3/2007 | Penuela |
| 7,194,038 B1 | 3/2007 | Inkinen |
| 7,196,495 B1 | 3/2007 | Burcham |
| 7,206,630 B1 | 4/2007 | Tarler |
| 7,209,790 B2 | 4/2007 | Thompson et al. |
| 7,215,660 B2 | 5/2007 | Perlman |
| 7,215,991 B2 | 5/2007 | Besson |
| 7,218,967 B2 | 5/2007 | Bergelson |
| 7,231,451 B2 | 6/2007 | Law |
| 7,243,118 B2 | 7/2007 | Lou |
| 7,246,521 B2 | 7/2007 | Kim |
| 7,249,212 B2 | 7/2007 | Do |
| 7,252,792 B2 | 8/2007 | Perrault |
| 7,253,716 B2 | 8/2007 | Lovoi et al. |
| 7,261,690 B2 | 8/2007 | Teller |
| 7,270,633 B1 | 9/2007 | Goscha |
| 7,273,454 B2 | 9/2007 | Raymond et al. |
| 7,283,867 B2 | 10/2007 | Strother et al. |
| 7,285,090 B2 | 10/2007 | Stivoric et al. |
| 7,289,855 B2 | 10/2007 | Nghiem |
| 7,291,497 B2 | 11/2007 | Holmes |
| 7,292,139 B2 | 11/2007 | Mazar et al. |
| 7,294,105 B1 | 11/2007 | Islam |
| 7,295,877 B2 | 11/2007 | Govari |
| 7,311,665 B2 | 12/2007 | Hawthorne |
| 7,313,163 B2 | 12/2007 | Liu |
| 7,317,378 B2 | 1/2008 | Jarvis et al. |
| 7,318,808 B2 | 1/2008 | Tarassenko et al. |
| 7,336,732 B1 | 2/2008 | Wiss |
| 7,336,929 B2 | 2/2008 | Yasuda |
| 7,342,895 B2 | 3/2008 | Serpa |
| 7,346,380 B2 | 3/2008 | Axelgaard et al. |
| 7,349,722 B2 | 3/2008 | Witkowski et al. |
| 7,352,998 B2 | 4/2008 | Palin |
| 7,353,258 B2 | 4/2008 | Washburn |
| 7,357,891 B2 | 4/2008 | Yang et al. |
| 7,359,674 B2 | 4/2008 | Markki |
| 7,366,558 B2 | 4/2008 | Virtanen et al. |
| 7,366,675 B1 | 4/2008 | Walker et al. |
| 7,368,190 B2 | 5/2008 | Heller et al. |
| 7,368,191 B2 | 5/2008 | Andelman et al. |
| 7,373,196 B2 | 5/2008 | Ryu et al. |
| 7,375,739 B2 | 5/2008 | Robbins |
| 7,376,435 B2 | 5/2008 | McGowan |
| 7,382,247 B2 * | 6/2008 | Welch .................. A61B 5/0024 340/539.1 |
| 7,382,263 B2 | 6/2008 | Danowski et al. |
| 7,387,607 B2 | 6/2008 | Holt |
| 7,388,903 B2 | 6/2008 | Godfrey et al. |
| 7,389,088 B2 | 6/2008 | Kim |
| 7,392,015 B1 | 6/2008 | Farlow |
| 7,395,105 B2 | 7/2008 | Schmidt et al. |
| 7,395,106 B2 | 7/2008 | Ryu et al. |
| 7,396,330 B2 | 7/2008 | Banet |
| 7,404,968 B2 | 7/2008 | Abrams et al. |
| 7,413,544 B2 | 8/2008 | Kerr |
| 7,414,534 B1 | 8/2008 | Kroll et al. |
| 7,414,543 B2 | 8/2008 | Rye et al. |
| 7,415,242 B1 | 8/2008 | Ngan |
| 7,419,468 B2 | 9/2008 | Shimizu et al. |
| 7,424,268 B2 | 9/2008 | Diener |
| 7,424,319 B2 | 9/2008 | Muehlsteff |
| 7,427,266 B2 | 9/2008 | Ayer et al. |
| 7,433,731 B2 | 10/2008 | Matsumura et al. |
| 7,442,164 B2 | 10/2008 | Berrang et al. |
| 7,443,290 B2 | 10/2008 | Takiguchi |
| 7,458,887 B2 | 12/2008 | Kurosawa |
| 7,462,150 B1 | 12/2008 | Bharmi |
| 7,469,838 B2 | 12/2008 | Brooks et al. |
| 7,471,665 B2 | 12/2008 | Perlman |
| 7,471,992 B2 | 12/2008 | Schmidt et al. |
| 7,476,104 B2 | 1/2009 | Marmaropoulos et al. |
| 7,485,093 B2 | 2/2009 | Glukhovsky |
| 7,485,095 B2 | 2/2009 | Shusterman |
| 7,492,128 B2 | 2/2009 | Shen |
| 7,499,674 B2 | 3/2009 | Salokannel |
| 7,502,643 B2 | 3/2009 | Farringdon et al. |
| 7,505,795 B1 | 3/2009 | Lim et al. |
| 7,508,248 B2 | 3/2009 | Yoshida |
| 7,510,121 B2 | 3/2009 | Koenck |
| 7,512,448 B2 | 3/2009 | Malick |
| 7,512,860 B2 | 3/2009 | Miyazaki et al. |
| 7,515,043 B2 | 4/2009 | Welch |
| 7,519,416 B2 | 4/2009 | Sula et al. |
| 7,523,756 B2 | 4/2009 | Minai |
| 7,525,426 B2 | 4/2009 | Edelstein |
| 7,527,807 B2 | 5/2009 | Choi et al. |
| 7,537,590 B2 | 5/2009 | Santini, Jr. et al. |
| 7,539,533 B2 | 5/2009 | Tran |
| 7,542,878 B2 | 6/2009 | Nanikashvili |
| 7,547,278 B2 | 6/2009 | Miyazaki et al. |
| 7,551,590 B2 | 6/2009 | Haller |
| 7,554,452 B2 | 6/2009 | Cole |

(56) References Cited

U.S. PATENT DOCUMENTS

| | | |
|---|---|---|
| 7,558,620 B2 | 7/2009 | Ishibashi |
| 7,558,965 B2 | 7/2009 | Wheeler et al. |
| 7,575,005 B2 | 8/2009 | Mumford |
| 7,599,003 B2 | 10/2009 | Suzuki et al. |
| 7,616,111 B2 | 11/2009 | Covannon |
| 7,616,710 B2 | 11/2009 | Kim et al. |
| 7,617,001 B2 | 11/2009 | Penner et al. |
| 7,626,387 B2 | 12/2009 | Adachi |
| 7,639,473 B2 | 12/2009 | Hsu et al. |
| 7,640,802 B2 | 1/2010 | King et al. |
| 7,645,262 B2 | 1/2010 | Greenberg et al. |
| 7,647,112 B2 | 1/2010 | Tracey |
| 7,647,185 B2 | 1/2010 | Tarassenko et al. |
| 7,653,031 B2 | 1/2010 | Godfrey et al. |
| 7,668,437 B1 | 2/2010 | Yamada et al. |
| 7,672,703 B2 | 3/2010 | Yeo et al. |
| 7,672,714 B2 | 3/2010 | Kuo |
| 7,673,679 B2 | 3/2010 | Harrison et al. |
| 7,678,043 B2 | 3/2010 | Gilad |
| 7,686,839 B2 | 3/2010 | Parker |
| 7,688,204 B2 | 3/2010 | Yamanaka et al. |
| 7,689,437 B1 | 3/2010 | Teller et al. |
| 7,689,833 B2 | 3/2010 | Lange |
| 7,697,994 B2 | 4/2010 | VanDanacker et al. |
| 7,712,288 B2 | 5/2010 | Ramasubramanian et al. |
| 7,720,036 B2 | 5/2010 | Sadri |
| 7,729,776 B2 | 6/2010 | Von Arx et al. |
| 7,733,224 B2 | 6/2010 | Tran |
| 7,736,318 B2 | 6/2010 | Costentino |
| 7,747,454 B2 | 6/2010 | Bartfeld et al. |
| 7,756,587 B2 | 7/2010 | Penner et al. |
| 7,760,104 B2 | 7/2010 | Asp |
| 7,764,996 B2 | 7/2010 | Zhang et al. |
| 7,779,614 B1 | 8/2010 | McGonagle et al. |
| 7,782,991 B2 | 8/2010 | Sobchak et al. |
| 7,796,043 B2 | 9/2010 | Euliano et al. |
| 7,797,033 B2 | 9/2010 | D'Andrea et al. |
| 7,806,852 B1 | 10/2010 | Jursen |
| 7,809,399 B2 | 10/2010 | Lu |
| 7,844,341 B2 | 11/2010 | Von Arx et al. |
| 7,857,766 B2 | 12/2010 | Lasater et al. |
| 7,860,731 B2 | 12/2010 | Jackson et al. |
| 7,881,799 B2 | 2/2011 | Greenberg et al. |
| 7,899,526 B2 | 3/2011 | Benditt et al. |
| 7,904,133 B2 | 3/2011 | Gehman et al. |
| 7,940,933 B2 | 5/2011 | Corndorf |
| D639,437 S | 6/2011 | Bishay et al. |
| 7,975,587 B2 | 7/2011 | Schneider |
| 7,978,064 B2 | 7/2011 | Zdeblick et al. |
| 7,983,189 B2 | 7/2011 | Bugenhagen |
| 8,025,149 B2 | 9/2011 | Sterry et al. |
| 8,036,731 B2 | 10/2011 | Kimchy et al. |
| 8,036,748 B2 | 10/2011 | Zdeblick et al. |
| 8,054,047 B2 | 11/2011 | Chen et al. |
| 8,054,140 B2 | 11/2011 | Fleming et al. |
| 8,055,334 B2 | 11/2011 | Savage et al. |
| 8,060,249 B2 | 11/2011 | Bear et al. |
| 8,073,707 B2 | 12/2011 | Teller et al. |
| 8,082,919 B2 | 12/2011 | Brunnberg et al. |
| 8,083,128 B2 | 12/2011 | Dembo et al. |
| 8,094,807 B2 | 1/2012 | Ishibashi et al. |
| 8,114,021 B2 | 2/2012 | Robertson et al. |
| 8,119,045 B2 | 2/2012 | Schmidt et al. |
| 8,123,576 B2 | 2/2012 | Kim |
| 8,131,376 B1 | 3/2012 | Faraji et al. |
| 8,135,596 B2 | 3/2012 | Jung et al. |
| 8,140,143 B2 | 3/2012 | Picard et al. |
| 8,170,515 B2 | 5/2012 | Le Reverend et al. |
| 8,180,425 B2 | 5/2012 | Selvitelli et al. |
| 8,184,854 B2 | 5/2012 | Bartsch |
| 8,185,191 B1 | 5/2012 | Shapiro et al. |
| 8,185,646 B2* | 5/2012 | Headley .............. G06F 21/32 709/225 |
| 8,193,821 B2 | 6/2012 | Mueller |
| 8,200,320 B2 | 6/2012 | Kovacs |
| 8,207,731 B2 | 6/2012 | Moskalenko |
| 8,209,018 B2 | 6/2012 | Osorio et al. |
| 8,214,007 B2 | 7/2012 | Baker et al. |
| 8,224,596 B2 | 7/2012 | Agrawal et al. |
| 8,224,667 B1 | 7/2012 | Miller et al. |
| 8,238,998 B2 | 8/2012 | Park |
| 8,249,686 B2 | 8/2012 | Libbus et al. |
| 8,253,586 B1 | 8/2012 | Matak |
| 8,254,853 B2* | 8/2012 | Rofougaran .......... G06F 19/323 455/100 |
| 8,258,962 B2 | 9/2012 | Robertson et al. |
| 8,262,394 B2 | 9/2012 | Walker et al. |
| 8,271,106 B2 | 9/2012 | Wehba et al. |
| 8,271,146 B2 | 9/2012 | Heber et al. |
| 8,285,356 B2 | 10/2012 | Bly et al. |
| 8,290,574 B2 | 10/2012 | Feild et al. |
| 8,298,574 B2 | 10/2012 | Tsabari et al. |
| 8,301,232 B2 | 10/2012 | Albert et al. |
| 8,308,640 B2 | 11/2012 | Baldus et al. |
| 8,314,619 B2 | 11/2012 | Takiguchi |
| 8,315,687 B2 | 11/2012 | Cross et al. |
| 8,332,009 B2 | 12/2012 | McLaughlin et al. |
| 8,343,068 B2 | 1/2013 | Najafi et al. |
| 8,360,976 B2 | 1/2013 | Imran |
| 8,369,936 B2 | 2/2013 | Farringdon et al. |
| 8,374,698 B2 | 2/2013 | Ok et al. |
| 8,386,009 B2 | 2/2013 | Lindberg et al. |
| 8,389,003 B2 | 3/2013 | Mintchev et al. |
| 8,404,275 B2 | 3/2013 | Habboushe |
| 8,425,492 B2 | 4/2013 | Herbert et al. |
| 8,440,274 B2 | 5/2013 | Wang |
| 8,443,214 B2 | 5/2013 | Lee et al. |
| 8,454,528 B2* | 6/2013 | Yuen .................... A61B 5/0205 340/539.12 |
| 8,454,561 B2 | 6/2013 | Uber, III et al. |
| 8,471,960 B2 | 6/2013 | Lin et al. |
| 8,514,086 B2 | 8/2013 | Harper et al. |
| 8,514,979 B2 | 8/2013 | Laporte |
| 8,532,776 B2 | 9/2013 | Greenberg et al. |
| 8,538,544 B2 | 9/2013 | Sivard |
| 8,540,664 B2 | 9/2013 | Robertson et al. |
| 8,545,436 B2 | 10/2013 | Robertson et al. |
| 8,547,248 B2 | 10/2013 | Zdeblick et al. |
| 8,548,033 B2 | 10/2013 | Nemeth et al. |
| 8,558,563 B2 | 10/2013 | Zdeblick |
| 8,564,432 B2 | 10/2013 | Covannon et al. |
| 8,564,627 B2 | 10/2013 | Suzuki et al. |
| 8,597,186 B2 | 12/2013 | Hafezi et al. |
| 8,604,674 B2 | 12/2013 | Ganeshan |
| 8,615,290 B2 | 12/2013 | Lin et al. |
| 8,620,402 B2 | 12/2013 | Parker, III et al. |
| 8,634,838 B2 | 1/2014 | Hellwig et al. |
| 8,645,101 B2 | 2/2014 | Humphries et al. |
| 8,660,645 B2 | 2/2014 | Stevenson et al. |
| 8,668,643 B2 | 3/2014 | Kinast |
| 8,668,645 B2 | 3/2014 | Heller et al. |
| 8,685,451 B2 | 4/2014 | Toneguzzo et al. |
| 8,697,057 B2 | 4/2014 | Van Epps et al. |
| 8,698,006 B2 | 4/2014 | Bealka et al. |
| 8,718,193 B2 | 5/2014 | Arne et al. |
| 8,722,085 B2 | 5/2014 | McKinney et al. |
| 8,725,243 B2 | 5/2014 | Dilorenzo et al. |
| 8,730,031 B2 | 5/2014 | Thompson et al. |
| 8,754,799 B2 | 6/2014 | Coln et al. |
| 8,758,237 B2 | 6/2014 | Sherman et al. |
| 8,762,733 B2 | 6/2014 | Derchak et al. |
| 8,771,183 B2 | 7/2014 | Sloan |
| 8,773,258 B2 | 7/2014 | Vosch et al. |
| 8,776,198 B2 | 7/2014 | Tsitkova et al. |
| 8,784,308 B2 | 7/2014 | Duck et al. |
| 8,802,183 B2 | 8/2014 | Frank et al. |
| 8,810,260 B1 | 8/2014 | Zhou |
| 8,810,409 B2 | 8/2014 | Robertson et al. |
| 8,816,847 B2 | 8/2014 | Zdeblick et al. |
| 8,823,510 B2 | 9/2014 | Downey et al. |
| 8,836,513 B2 | 9/2014 | Hafezi et al. |
| 8,838,217 B2 | 9/2014 | Myr |
| 8,858,432 B2 | 10/2014 | Robertson |
| 8,868,453 B2 | 10/2014 | Zdeblick |

(56) References Cited

U.S. PATENT DOCUMENTS

| | | | |
|---|---|---|---|
| 8,908,943 B2 | 12/2014 | Berry et al. | |
| 8,912,908 B2 | 12/2014 | Berkman et al. | |
| 8,920,345 B2 | 12/2014 | Greenberg | |
| 8,926,509 B2 * | 1/2015 | Magar | A61B 5/0205 340/539.12 |
| 8,932,221 B2 | 1/2015 | Colliou et al. | |
| 8,945,005 B2 | 2/2015 | Hafezi et al. | |
| 8,951,234 B2 | 2/2015 | Hafezi et al. | |
| 8,956,287 B2 | 2/2015 | Zdeblick et al. | |
| 8,956,288 B2 | 2/2015 | Hafezi et al. | |
| 8,966,973 B1 | 3/2015 | Milone | |
| 8,989,837 B2 * | 3/2015 | Weinstein | A61B 5/0402 600/407 |
| 9,031,658 B2 | 5/2015 | Chiao et al. | |
| 9,047,746 B1 | 6/2015 | Euliano et al. | |
| 9,088,168 B2 | 7/2015 | Mach et al. | |
| 9,107,806 B2 | 8/2015 | Hafezi et al. | |
| 9,119,918 B2 | 9/2015 | Robertson et al. | |
| 9,125,868 B2 | 9/2015 | McKinney et al. | |
| 9,149,577 B2 | 10/2015 | Robertson et al. | |
| 9,158,890 B2 | 10/2015 | Meredith et al. | |
| 9,189,941 B2 | 11/2015 | Eschelman et al. | |
| 9,226,663 B2 | 1/2016 | Fei | |
| 9,226,679 B2 | 1/2016 | Balda | |
| 9,235,683 B2 | 1/2016 | Robertson et al. | |
| 9,258,035 B2 | 2/2016 | Robertson et al. | |
| 9,268,909 B2 | 2/2016 | Jani et al. | |
| 9,270,025 B2 * | 2/2016 | Robertson | A61B 5/0031 |
| 9,271,897 B2 | 3/2016 | Costello et al. | |
| 9,277,864 B2 | 3/2016 | Yang et al. | |
| 9,278,177 B2 | 3/2016 | Edwards et al. | |
| 9,320,455 B2 * | 4/2016 | Hafezi | A61B 5/0031 |
| 9,415,010 B2 | 8/2016 | Hafezi et al. | |
| 9,433,371 B2 | 9/2016 | Hafezi et al. | |
| 9,439,566 B2 | 9/2016 | Arne et al. | |
| 9,439,582 B2 * | 9/2016 | Berkman | A61B 5/0538 |
| 9,439,599 B2 * | 9/2016 | Thompson | A61B 5/0006 |
| 9,444,503 B2 | 9/2016 | Arne et al. | |
| 9,517,012 B2 * | 12/2016 | Lane | A61B 5/0024 |
| 9,599,679 B2 | 3/2017 | Taylor et al. | |
| 9,603,550 B2 | 3/2017 | Behzadi | |
| 9,649,066 B2 | 5/2017 | Zdeblick et al. | |
| 9,659,423 B2 | 5/2017 | Robertson et al. | |
| 9,741,975 B2 | 8/2017 | Laulicht et al. | |
| 9,883,819 B2 | 2/2018 | Jensen et al. | |
| 2001/0027331 A1 | 10/2001 | Thompson | |
| 2001/0031071 A1 | 10/2001 | Nichols et al. | |
| 2001/0039503 A1 | 11/2001 | Chan et al. | |
| 2001/0044588 A1 | 11/2001 | Mault | |
| 2001/0051766 A1 | 12/2001 | Gazdinski | |
| 2001/0056262 A1 | 12/2001 | Cabin et al. | |
| 2002/0002326 A1 | 1/2002 | Causey et al. | |
| 2002/0019586 A1 | 2/2002 | Teller et al. | |
| 2002/0026111 A1 | 2/2002 | Ackerman | |
| 2002/0032384 A1 | 3/2002 | Raymond et al. | |
| 2002/0032385 A1 | 3/2002 | Raymond et al. | |
| 2002/0040278 A1 | 4/2002 | Anuzis et al. | |
| 2002/0067270 A1 | 6/2002 | Yarin et al. | |
| 2002/0077620 A1 | 6/2002 | Sweeney et al. | |
| 2002/0132226 A1 | 9/2002 | Nair | |
| 2002/0136744 A1 | 9/2002 | McGlynn et al. | |
| 2002/0138009 A1 | 9/2002 | Brockway et al. | |
| 2002/0169696 A1 | 11/2002 | Zara | |
| 2002/0179921 A1 | 12/2002 | Cohn | |
| 2002/0184415 A1 | 12/2002 | Naghavi et al. | |
| 2002/0192159 A1 | 12/2002 | Reitberg | |
| 2002/0193669 A1 | 12/2002 | Glukhovsky | |
| 2002/0193846 A1 | 12/2002 | Pool et al. | |
| 2002/0198470 A1 | 12/2002 | Imran et al. | |
| 2003/0017826 A1 | 1/2003 | vrijens et al. | |
| 2003/0023150 A1 | 1/2003 | Yokoi et al. | |
| 2003/0028226 A1 | 2/2003 | Thompson | |
| 2003/0037063 A1 | 2/2003 | Schwartz | |
| 2003/0062551 A1 | 4/2003 | Chen et al. | |
| 2003/0063522 A1 | 4/2003 | Sagar | |
| 2003/0065536 A1 | 4/2003 | Hansen | |
| 2003/0076179 A1 | 4/2003 | Branch et al. | |
| 2003/0083559 A1 | 5/2003 | Thompson | |
| 2003/0091121 A1 | 5/2003 | Kenmochi | |
| 2003/0091625 A1 | 5/2003 | Hariharan et al. | |
| 2003/0126593 A1 | 7/2003 | Mault | |
| 2003/0130714 A1 | 7/2003 | Nielsen et al. | |
| 2003/0135128 A1 | 7/2003 | Suffin et al. | |
| 2003/0135392 A1 | 7/2003 | Vrijens et al. | |
| 2003/0152622 A1 | 8/2003 | Louie-Helm et al. | |
| 2003/0158466 A1 | 8/2003 | Lynn et al. | |
| 2003/0158756 A1 | 8/2003 | Abramson | |
| 2003/0162556 A1 | 8/2003 | Libes | |
| 2003/0164401 A1 | 9/2003 | Andreasson et al. | |
| 2003/0167000 A1 | 9/2003 | Mullick et al. | |
| 2003/0171791 A1 | 9/2003 | KenKnight | |
| 2003/0171898 A1 | 9/2003 | Tarassenko et al. | |
| 2003/0181788 A1 | 9/2003 | Yokoi et al. | |
| 2003/0181815 A1 | 9/2003 | Ebner et al. | |
| 2003/0185286 A1 | 10/2003 | Yuen | |
| 2003/0187337 A1 | 10/2003 | Tarassenko et al. | |
| 2003/0187338 A1 | 10/2003 | Say et al. | |
| 2003/0195403 A1 | 10/2003 | Berner et al. | |
| 2003/0198619 A1 | 10/2003 | Dong et al. | |
| 2003/0213495 A1 | 11/2003 | Fujita et al. | |
| 2003/0214579 A1 | 11/2003 | Iddan | |
| 2003/0216622 A1 | 11/2003 | Meron et al. | |
| 2003/0216625 A1 | 11/2003 | Phipps | |
| 2003/0216666 A1 | 11/2003 | Ericson et al. | |
| 2003/0216729 A1 | 11/2003 | Marchitto | |
| 2003/0216793 A1 | 11/2003 | Karlsson et al. | |
| 2003/0219484 A1 | 11/2003 | Sowden et al. | |
| 2003/0229382 A1 | 12/2003 | Sun et al. | |
| 2003/0232895 A1 | 12/2003 | Omidian et al. | |
| 2004/0008123 A1 | 1/2004 | Carrender et al. | |
| 2004/0018476 A1 | 1/2004 | LaDue | |
| 2004/0019172 A1 | 1/2004 | Yang et al. | |
| 2004/0034295 A1 | 2/2004 | Salganicoff | |
| 2004/0049245 A1 | 3/2004 | Gass | |
| 2004/0073095 A1 | 4/2004 | Causey et al. | |
| 2004/0073454 A1 | 4/2004 | Urquhart et al. | |
| 2004/0077995 A1 | 4/2004 | Ferek-Petric | |
| 2004/0082982 A1 | 4/2004 | Gord et al. | |
| 2004/0087839 A1 | 5/2004 | Raymond et al. | |
| 2004/0092801 A1 | 5/2004 | Drakulic | |
| 2004/0106859 A1 | 6/2004 | Say et al. | |
| 2004/0111011 A1 | 6/2004 | Uchiyama et al. | |
| 2004/0115507 A1 | 6/2004 | Potter et al. | |
| 2004/0115517 A1 | 6/2004 | Fukada et al. | |
| 2004/0121015 A1 | 6/2004 | Chidlaw et al. | |
| 2004/0122296 A1 | 6/2004 | Hatlestad | |
| 2004/0122297 A1 | 6/2004 | Stahmann et al. | |
| 2004/0138558 A1 | 7/2004 | Dunki-Jacobs et al. | |
| 2004/0147326 A1 | 7/2004 | Stiles | |
| 2004/0148140 A1 | 7/2004 | Tarassenko et al. | |
| 2004/0153007 A1 | 8/2004 | Harris | |
| 2004/0167226 A1 | 8/2004 | Serafini | |
| 2004/0167801 A1 | 8/2004 | Say et al. | |
| 2004/0171914 A1 | 9/2004 | Avni | |
| 2004/0193020 A1 | 9/2004 | Chiba | |
| 2004/0193029 A1 | 9/2004 | Gluhovsky | |
| 2004/0193446 A1 | 9/2004 | Mayer et al. | |
| 2004/0199222 A1 | 10/2004 | Sun et al. | |
| 2004/0215084 A1 | 10/2004 | Shimizu et al. | |
| 2004/0218683 A1 | 11/2004 | Batra | |
| 2004/0220643 A1 | 11/2004 | Schmidt | |
| 2004/0224644 A1 | 11/2004 | Wu | |
| 2004/0225199 A1 | 11/2004 | Evanyk | |
| 2004/0253304 A1 | 12/2004 | Gross et al. | |
| 2004/0258571 A1 | 12/2004 | Lee et al. | |
| 2004/0259899 A1 | 12/2004 | Sanghvi et al. | |
| 2004/0260154 A1 | 12/2004 | Sidelnik | |
| 2004/0267240 A1 | 12/2004 | Gross et al. | |
| 2005/0003074 A1 | 1/2005 | Brown et al. | |
| 2005/0010338 A1 | 1/2005 | Kraeling et al. | |
| 2005/0017841 A1 | 1/2005 | Doi | |
| 2005/0020887 A1 | 1/2005 | Goldberg | |
| 2005/0021103 A1 | 1/2005 | DiLorenzo | |
| 2005/0021370 A1 | 1/2005 | Riff | |

(56) References Cited

U.S. PATENT DOCUMENTS

| | | |
|---|---|---|
| 2005/0021372 A1 | 1/2005 | Mikkelsen |
| 2005/0024198 A1 | 2/2005 | Ward |
| 2005/0027175 A1 | 2/2005 | Yang |
| 2005/0027205 A1 | 2/2005 | Tarassenko et al. |
| 2005/0038321 A1 | 2/2005 | Fujita et al. |
| 2005/0038680 A1 | 2/2005 | McMahon |
| 2005/0041752 A1 | 2/2005 | Rosen |
| 2005/0043583 A1 | 2/2005 | Killman et al. |
| 2005/0043634 A1 | 2/2005 | Yokoi et al. |
| 2005/0043894 A1 | 2/2005 | Fernandez |
| 2005/0054897 A1 | 3/2005 | Hashimoto et al. |
| 2005/0055014 A1 | 3/2005 | Coppeta et al. |
| 2005/0062644 A1 | 3/2005 | Leci |
| 2005/0065407 A1 | 3/2005 | Nakamura et al. |
| 2005/0070778 A1 | 3/2005 | Lackey |
| 2005/0075145 A1 | 4/2005 | Dvorak et al. |
| 2005/0090753 A1 | 4/2005 | Goor et al. |
| 2005/0092108 A1 | 5/2005 | Andermo |
| 2005/0096514 A1 | 5/2005 | Starkebaum |
| 2005/0096562 A1 | 5/2005 | Delalic et al. |
| 2005/0101843 A1 | 5/2005 | Quinn |
| 2005/0101872 A1 | 5/2005 | Sattler |
| 2005/0115561 A1 | 6/2005 | Stahmann et al. |
| 2005/0116820 A1 | 6/2005 | Goldreich |
| 2005/0117389 A1 | 6/2005 | Worledge |
| 2005/0121322 A1 | 6/2005 | Say et al. |
| 2005/0131281 A1 | 6/2005 | Ayer et al. |
| 2005/0137480 A1 | 6/2005 | Alt et al. |
| 2005/0143623 A1 | 6/2005 | Kojima |
| 2005/0146594 A1 | 7/2005 | Nakatani et al. |
| 2005/0148883 A1 | 7/2005 | Boesen |
| 2005/0151625 A1 | 7/2005 | Lai |
| 2005/0154277 A1 | 7/2005 | Tang et al. |
| 2005/0154428 A1 | 7/2005 | Bruinsma |
| 2005/0156709 A1 | 7/2005 | Gilbert et al. |
| 2005/0159789 A1 | 7/2005 | Brockway |
| 2005/0165323 A1 | 7/2005 | Montgomery |
| 2005/0177069 A1 | 8/2005 | Takizawa |
| 2005/0182389 A1 | 8/2005 | LaPorte |
| 2005/0187789 A1 | 8/2005 | Hatlestad et al. |
| 2005/0192489 A1 | 9/2005 | Marshall |
| 2005/0197680 A1 | 9/2005 | DelMain et al. |
| 2005/0208251 A1 | 9/2005 | Aisenbrey |
| 2005/0228268 A1 | 10/2005 | Cole |
| 2005/0234307 A1 | 10/2005 | Heinonen |
| 2005/0240305 A1 | 10/2005 | Bogash et al. |
| 2005/0245794 A1 | 11/2005 | Dinsmoor |
| 2005/0245839 A1 | 11/2005 | Stivoric et al. |
| 2005/0259768 A1 | 11/2005 | Yang et al. |
| 2005/0261559 A1 | 11/2005 | Mumford |
| 2005/0267550 A1 | 12/2005 | Hess et al. |
| 2005/0267556 A1 | 12/2005 | Shuros et al. |
| 2005/0267756 A1 | 12/2005 | Schultz et al. |
| 2005/0277912 A1 | 12/2005 | John |
| 2005/0277999 A1 | 12/2005 | Strother et al. |
| 2005/0279054 A1 | 12/2005 | Mauze et al. |
| 2005/0280539 A1 | 12/2005 | Pettus |
| 2005/0285732 A1 | 12/2005 | Sengupta et al. |
| 2005/0285746 A1 | 12/2005 | Sengupta |
| 2005/0288594 A1 | 12/2005 | Lewkowicz et al. |
| 2006/0001496 A1 | 1/2006 | Abrosimov et al. |
| 2006/0028727 A1 | 2/2006 | Moon et al. |
| 2006/0036134 A1 | 2/2006 | Tarassenko et al. |
| 2006/0058602 A1 | 3/2006 | Kwiatkowski et al. |
| 2006/0061472 A1 | 3/2006 | Lovoi et al. |
| 2006/0065713 A1 | 3/2006 | Kingery |
| 2006/0068006 A1 | 3/2006 | Begleiter |
| 2006/0074283 A1 | 4/2006 | Henderson |
| 2006/0074319 A1 | 4/2006 | Barnes et al. |
| 2006/0078765 A1 | 4/2006 | Yang et al. |
| 2006/0089858 A1 | 4/2006 | Ling |
| 2006/0095091 A1 | 5/2006 | Drew |
| 2006/0095093 A1 | 5/2006 | Bettesh et al. |
| 2006/0100533 A1 | 5/2006 | Han |
| 2006/0109058 A1 | 5/2006 | Keating |
| 2006/0110962 A1 | 5/2006 | Powell |
| 2006/0122474 A1 | 6/2006 | Teller et al. |
| 2006/0122667 A1 | 6/2006 | Chavan et al. |
| 2006/0129060 A1 | 6/2006 | Lee et al. |
| 2006/0136266 A1 | 6/2006 | Tarassenko et al. |
| 2006/0136744 A1 | 6/2006 | Lange |
| 2006/0142648 A1 | 6/2006 | Banet |
| 2006/0145876 A1 | 7/2006 | Kimura |
| 2006/0148254 A1 | 7/2006 | McLean |
| 2006/0149339 A1 | 7/2006 | Burnes |
| 2006/0155174 A1 | 7/2006 | Glukhovsky et al. |
| 2006/0155183 A1 | 7/2006 | Kroecker |
| 2006/0158820 A1 | 7/2006 | Takiguchi |
| 2006/0161225 A1 | 7/2006 | Sormann et al. |
| 2006/0179949 A1 | 8/2006 | Kim |
| 2006/0183992 A1 | 8/2006 | Kawashima |
| 2006/0183993 A1 | 8/2006 | Horn |
| 2006/0184092 A1 | 8/2006 | Atanasoska et al. |
| 2006/0204738 A1 | 9/2006 | Dubrow et al. |
| 2006/0210626 A1 | 9/2006 | Spaeder |
| 2006/0216603 A1 | 9/2006 | Choi |
| 2006/0218011 A1 | 9/2006 | Walker |
| 2006/0229053 A1 | 10/2006 | Sivard |
| 2006/0235489 A1 | 10/2006 | Drew |
| 2006/0243288 A1 | 11/2006 | Kim et al. |
| 2006/0247505 A1 | 11/2006 | Siddiqui |
| 2006/0253004 A1 | 11/2006 | Frisch et al. |
| 2006/0253005 A1 | 11/2006 | Drinan |
| 2006/0255064 A1 | 11/2006 | Donaldson |
| 2006/0265246 A1 | 11/2006 | Hoag |
| 2006/0267774 A1 | 11/2006 | Feinberg et al. |
| 2006/0270346 A1 | 11/2006 | Ibrahim |
| 2006/0273882 A1 | 12/2006 | Posamentier |
| 2006/0276702 A1 | 12/2006 | McGinnis |
| 2006/0277097 A1 | 12/2006 | Shafron et al. |
| 2006/0280227 A1 | 12/2006 | Pinkney |
| 2006/0282001 A1 | 12/2006 | Noel |
| 2006/0285607 A1 | 12/2006 | Strodtbeck et al. |
| 2006/0287693 A1 | 12/2006 | Kraft et al. |
| 2006/0289640 A1 | 12/2006 | Mercure |
| 2006/0293607 A1 | 12/2006 | Alt |
| 2007/0000776 A1 | 1/2007 | Karube et al. |
| 2007/0002038 A1 | 1/2007 | Suzuki |
| 2007/0006636 A1 | 1/2007 | King et al. |
| 2007/0008113 A1 | 1/2007 | Spoonhower et al. |
| 2007/0016089 A1 | 1/2007 | Fischell et al. |
| 2007/0027386 A1 | 2/2007 | Such |
| 2007/0027388 A1 | 2/2007 | Chou |
| 2007/0038054 A1 | 2/2007 | Zhou |
| 2007/0049339 A1 | 3/2007 | Barak et al. |
| 2007/0055098 A1 | 3/2007 | Shimizu et al. |
| 2007/0060797 A1 | 3/2007 | Ball |
| 2007/0060800 A1 | 3/2007 | Drinan et al. |
| 2007/0066929 A1 | 3/2007 | Ferren et al. |
| 2007/0072156 A1 | 3/2007 | Kaufman et al. |
| 2007/0073353 A1 | 3/2007 | Rooney et al. |
| 2007/0088194 A1 | 4/2007 | Tahar |
| 2007/0096765 A1 | 5/2007 | Kagan |
| 2007/0106346 A1 | 5/2007 | Bergelson |
| 2007/0123772 A1 | 5/2007 | Euliano |
| 2007/0129622 A1 | 6/2007 | Bourget |
| 2007/0130287 A1 | 6/2007 | Kumar |
| 2007/0135691 A1 | 6/2007 | Zingelewicz et al. |
| 2007/0135803 A1 | 6/2007 | Belson |
| 2007/0142721 A1 | 6/2007 | Berner et al. |
| 2007/0156016 A1 | 7/2007 | Betesh |
| 2007/0160789 A1 | 7/2007 | Merical |
| 2007/0162089 A1 | 7/2007 | Mosesov |
| 2007/0162090 A1 | 7/2007 | Penner |
| 2007/0164752 A1 | 7/2007 | Kato |
| 2007/0167495 A1 | 7/2007 | Brown et al. |
| 2007/0167848 A1 | 7/2007 | Kuo et al. |
| 2007/0173701 A1 | 7/2007 | Al-Ali |
| 2007/0179347 A1 | 8/2007 | Tarassenko et al. |
| 2007/0179371 A1 | 8/2007 | Peyser et al. |
| 2007/0180047 A1 | 8/2007 | Dong et al. |
| 2007/0185393 A1 | 8/2007 | Zhou |
| 2007/0191002 A1 | 8/2007 | Ge |
| 2007/0196456 A1 | 8/2007 | Stevens |

(56) References Cited

U.S. PATENT DOCUMENTS

| | | |
|---|---|---|
| 2007/0207793 A1 | 9/2007 | Myer |
| 2007/0207858 A1 | 9/2007 | Breving |
| 2007/0208233 A1 | 9/2007 | Kovacs |
| 2007/0213659 A1 | 9/2007 | Trovato et al. |
| 2007/0237719 A1 | 10/2007 | Jones |
| 2007/0244370 A1 | 10/2007 | Kuo et al. |
| 2007/0244810 A1 | 10/2007 | Rudolph |
| 2007/0249946 A1 | 10/2007 | Kumar et al. |
| 2007/0255198 A1 | 11/2007 | Leong et al. |
| 2007/0255330 A1 | 11/2007 | Lee |
| 2007/0270672 A1 | 11/2007 | Hayter |
| 2007/0279217 A1 | 12/2007 | Venkatraman |
| 2007/0282174 A1 | 12/2007 | Sabatino |
| 2007/0282177 A1 | 12/2007 | Pilz |
| 2007/0291715 A1 | 12/2007 | Laroia et al. |
| 2007/0299480 A1 | 12/2007 | Hill |
| 2008/0000804 A1 | 1/2008 | Carey et al. |
| 2008/0004503 A1 | 1/2008 | Nisani et al. |
| 2008/0014866 A1 | 1/2008 | Lipowshi |
| 2008/0015421 A1 | 1/2008 | Penner |
| 2008/0015494 A1 | 1/2008 | Santini et al. |
| 2008/0015893 A1 | 1/2008 | Miller et al. |
| 2008/0020037 A1 | 1/2008 | Robertson et al. |
| 2008/0021519 A1 | 1/2008 | DeGeest |
| 2008/0021521 A1 | 1/2008 | Shah |
| 2008/0027679 A1 | 1/2008 | Shklarski |
| 2008/0033273 A1 | 2/2008 | Zhou |
| 2008/0033301 A1 | 2/2008 | Dellavecchia et al. |
| 2008/0038588 A1 | 2/2008 | Lee |
| 2008/0039700 A1 | 2/2008 | Drinan et al. |
| 2008/0045843 A1 | 2/2008 | Tsuji et al. |
| 2008/0046038 A1 | 2/2008 | Hill |
| 2008/0051647 A1 | 2/2008 | Wu et al. |
| 2008/0051667 A1 | 2/2008 | Goldreich |
| 2008/0051767 A1 | 2/2008 | Rossing et al. |
| 2008/0058614 A1 | 3/2008 | Banet |
| 2008/0062856 A1 | 3/2008 | Feher |
| 2008/0065168 A1 | 3/2008 | Bitton et al. |
| 2008/0074307 A1 | 3/2008 | Boric-Lubecke |
| 2008/0077015 A1 | 3/2008 | Botic-Lubecke |
| 2008/0077028 A1 | 3/2008 | Schaldach et al. |
| 2008/0077188 A1 | 3/2008 | Denker et al. |
| 2008/0077430 A1 | 3/2008 | Singer et al. |
| 2008/0091089 A1 | 4/2008 | Guillory et al. |
| 2008/0091114 A1 | 4/2008 | Min |
| 2008/0097549 A1 | 4/2008 | Colbaugh |
| 2008/0097917 A1 | 4/2008 | Dicks |
| 2008/0099366 A1 | 5/2008 | Niemic et al. |
| 2008/0103440 A1 | 5/2008 | Ferren et al. |
| 2008/0112885 A1 | 5/2008 | Okunev et al. |
| 2008/0114224 A1 | 5/2008 | Bandy et al. |
| 2008/0119705 A1 | 5/2008 | Patel |
| 2008/0119716 A1 | 5/2008 | Boric-Lubecke |
| 2008/0121825 A1 | 5/2008 | Trovato et al. |
| 2008/0137566 A1 | 6/2008 | Marholev |
| 2008/0139907 A1 | 6/2008 | Rao et al. |
| 2008/0140403 A1 | 6/2008 | Hughes et al. |
| 2008/0146871 A1 | 6/2008 | Arneson et al. |
| 2008/0146889 A1 | 6/2008 | Young |
| 2008/0146892 A1 | 6/2008 | LeBoeuf |
| 2008/0154104 A1 | 6/2008 | Lamego |
| 2008/0166992 A1 | 7/2008 | Ricordi |
| 2008/0175898 A1 | 7/2008 | Jones et al. |
| 2008/0183245 A1 | 7/2008 | Van Oort |
| 2008/0188763 A1 | 8/2008 | John et al. |
| 2008/0188837 A1 | 8/2008 | Belsky et al. |
| 2008/0194912 A1 | 8/2008 | Trovato et al. |
| 2008/0208009 A1 | 8/2008 | Shklarski |
| 2008/0214901 A1 | 9/2008 | Gehman |
| 2008/0214903 A1 | 9/2008 | Orbach |
| 2008/0214985 A1 | 9/2008 | Yanaki |
| 2008/0223936 A1 | 9/2008 | Mickle et al. |
| 2008/0243020 A1 | 10/2008 | Chou |
| 2008/0249360 A1 | 10/2008 | Li |
| 2008/0262320 A1 | 10/2008 | Schaefer et al. |
| 2008/0262336 A1 | 10/2008 | Ryu |
| 2008/0269664 A1 | 10/2008 | Trovato et al. |
| 2008/0275312 A1 | 11/2008 | Mosesov |
| 2008/0281636 A1 | 11/2008 | Jung et al. |
| 2008/0284599 A1 | 11/2008 | Zdeblick et al. |
| 2008/0288026 A1 | 11/2008 | Cross et al. |
| 2008/0288027 A1 | 11/2008 | Kroll |
| 2008/0294020 A1 | 11/2008 | Sapounas |
| 2008/0299197 A1 | 12/2008 | Toneguzzo et al. |
| 2008/0300572 A1 | 12/2008 | Rankers |
| 2008/0303638 A1 | 12/2008 | Nguyen |
| 2008/0303665 A1 | 12/2008 | Naik et al. |
| 2008/0306357 A1 | 12/2008 | Korman |
| 2008/0306359 A1 | 12/2008 | Zdeblick et al. |
| 2008/0306360 A1 | 12/2008 | Robertson et al. |
| 2008/0306362 A1 | 12/2008 | Davis |
| 2008/0311852 A1 | 12/2008 | Hansen |
| 2008/0312522 A1 | 12/2008 | Rowlandson |
| 2008/0316020 A1 | 12/2008 | Robertson |
| 2009/0006133 A1 | 1/2009 | Weinert |
| 2009/0009330 A1 | 1/2009 | Sakama et al. |
| 2009/0009332 A1 | 1/2009 | Nunez et al. |
| 2009/0024045 A1 | 1/2009 | Prakash |
| 2009/0024112 A1 | 1/2009 | Edwards et al. |
| 2009/0030293 A1 | 1/2009 | Cooper et al. |
| 2009/0030297 A1 | 1/2009 | Miller |
| 2009/0034209 A1 | 2/2009 | Joo |
| 2009/0043171 A1 | 2/2009 | Rule |
| 2009/0048498 A1 | 2/2009 | Riskey |
| 2009/0062634 A1 | 3/2009 | Say et al. |
| 2009/0062670 A1 | 3/2009 | Sterling |
| 2009/0062730 A1 | 3/2009 | Woo |
| 2009/0069642 A1 | 3/2009 | Gao |
| 2009/0069655 A1 | 3/2009 | Say et al. |
| 2009/0069656 A1 | 3/2009 | Say et al. |
| 2009/0069657 A1 | 3/2009 | Say et al. |
| 2009/0069658 A1 | 3/2009 | Say et al. |
| 2009/0069724 A1 | 3/2009 | Otto et al. |
| 2009/0076340 A1 | 3/2009 | Libbus et al. |
| 2009/0076343 A1 | 3/2009 | James |
| 2009/0076350 A1* | 3/2009 | Bly .............. A61B 5/0006 600/301 |
| 2009/0076397 A1 | 3/2009 | Libbus et al. |
| 2009/0082645 A1 | 3/2009 | Hafezi et al. |
| 2009/0087483 A1 | 4/2009 | Sison |
| 2009/0088618 A1 | 4/2009 | Ameson |
| 2009/0099435 A1 | 4/2009 | Say et al. |
| 2009/0105561 A1 | 4/2009 | Boydon et al. |
| 2009/0110148 A1 | 4/2009 | Zhang |
| 2009/0112626 A1 | 4/2009 | Talbot |
| 2009/0124871 A1 | 5/2009 | Arshak |
| 2009/0124965 A1 | 5/2009 | Greenberg et al. |
| 2009/0131774 A1 | 5/2009 | Sweitzer |
| 2009/0134181 A1 | 5/2009 | Wachman et al. |
| 2009/0135886 A1 | 5/2009 | Robertson et al. |
| 2009/0142853 A1 | 6/2009 | Warrington et al. |
| 2009/0149708 A1 | 6/2009 | Hyde et al. |
| 2009/0149839 A1 | 6/2009 | Hyde et al. |
| 2009/0153397 A1 | 6/2009 | Li et al. |
| 2009/0157113 A1 | 6/2009 | Marcotte |
| 2009/0157358 A1 | 6/2009 | Kim |
| 2009/0161602 A1 | 6/2009 | Matsumoto |
| 2009/0163789 A1 | 6/2009 | Say et al. |
| 2009/0171180 A1 | 7/2009 | Pering |
| 2009/0171420 A1 | 7/2009 | Brown et al. |
| 2009/0173628 A1 | 7/2009 | Say et al. |
| 2009/0177055 A1 | 7/2009 | Say et al. |
| 2009/0177056 A1 | 7/2009 | Say et al. |
| 2009/0177057 A1 | 7/2009 | Say et al. |
| 2009/0177058 A1 | 7/2009 | Say et al. |
| 2009/0177059 A1 | 7/2009 | Say et al. |
| 2009/0177060 A1 | 7/2009 | Say et al. |
| 2009/0177061 A1 | 7/2009 | Say et al. |
| 2009/0177062 A1 | 7/2009 | Say et al. |
| 2009/0177063 A1 | 7/2009 | Say et al. |
| 2009/0177064 A1 | 7/2009 | Say et al. |
| 2009/0177065 A1 | 7/2009 | Say et al. |
| 2009/0177066 A1 | 7/2009 | Say et al. |
| 2009/0182206 A1 | 7/2009 | Najafi |

(56) References Cited

U.S. PATENT DOCUMENTS

| | | |
|---|---|---|
| 2009/0182207 A1 | 7/2009 | Riskey et al. |
| 2009/0182212 A1 | 7/2009 | Say et al. |
| 2009/0182213 A1 | 7/2009 | Say et al. |
| 2009/0182214 A1 | 7/2009 | Say et al. |
| 2009/0182215 A1 | 7/2009 | Say et al. |
| 2009/0182388 A1 | 7/2009 | Von Arx |
| 2009/0187088 A1 | 7/2009 | Say et al. |
| 2009/0187089 A1 | 7/2009 | Say et al. |
| 2009/0187090 A1 | 7/2009 | Say et al. |
| 2009/0187091 A1 | 7/2009 | Say et al. |
| 2009/0187092 A1 | 7/2009 | Say et al. |
| 2009/0187093 A1 | 7/2009 | Say et al. |
| 2009/0187094 A1 | 7/2009 | Say et al. |
| 2009/0187095 A1 | 7/2009 | Say et al. |
| 2009/0187381 A1 | 7/2009 | King et al. |
| 2009/0192351 A1 | 7/2009 | Nishino |
| 2009/0192368 A1 | 7/2009 | Say et al. |
| 2009/0192369 A1 | 7/2009 | Say et al. |
| 2009/0192370 A1 | 7/2009 | Say et al. |
| 2009/0192371 A1 | 7/2009 | Say et al. |
| 2009/0192372 A1 | 7/2009 | Say et al. |
| 2009/0192373 A1 | 7/2009 | Say et al. |
| 2009/0192374 A1 | 7/2009 | Say et al. |
| 2009/0192375 A1 | 7/2009 | Say et al. |
| 2009/0192376 A1 | 7/2009 | Say et al. |
| 2009/0192377 A1 | 7/2009 | Say et al. |
| 2009/0192378 A1 | 7/2009 | Say et al. |
| 2009/0192379 A1 | 7/2009 | Say et al. |
| 2009/0198115 A1 | 8/2009 | Say et al. |
| 2009/0198116 A1 | 8/2009 | Say et al. |
| 2009/0198175 A1 | 8/2009 | Say et al. |
| 2009/0203964 A1 | 8/2009 | Shimizu et al. |
| 2009/0203971 A1 | 8/2009 | Sciarappa |
| 2009/0203972 A1 | 8/2009 | Heneghan |
| 2009/0203978 A1 | 8/2009 | Say et al. |
| 2009/0204265 A1 | 8/2009 | Hackett |
| 2009/0210164 A1 | 8/2009 | Say et al. |
| 2009/0216101 A1 | 8/2009 | Say et al. |
| 2009/0216102 A1 | 8/2009 | Say et al. |
| 2009/0227204 A1 | 9/2009 | Robertson et al. |
| 2009/0227876 A1 | 9/2009 | Tran |
| 2009/0227940 A1 | 9/2009 | Say et al. |
| 2009/0227941 A1 | 9/2009 | Say et al. |
| 2009/0227988 A1 | 9/2009 | Wood et al. |
| 2009/0228214 A1 | 9/2009 | Say et al. |
| 2009/0231125 A1 | 9/2009 | Baldus |
| 2009/0234200 A1 | 9/2009 | Husheer |
| 2009/0243833 A1 | 10/2009 | Huang |
| 2009/0247836 A1 | 10/2009 | Cole et al. |
| 2009/0253960 A1 | 10/2009 | Takenaka et al. |
| 2009/0256702 A1 | 10/2009 | Robertson |
| 2009/0260212 A1 | 10/2009 | Schmett et al. |
| 2009/0264714 A1 | 10/2009 | Chou |
| 2009/0264964 A1 | 10/2009 | Abrahamson |
| 2009/0265186 A1 | 10/2009 | Tarassenko et al. |
| 2009/0273467 A1 | 11/2009 | Elixmann |
| 2009/0277815 A1 | 11/2009 | Kohl et al. |
| 2009/0281539 A1 | 11/2009 | Selig |
| 2009/0287109 A1* | 11/2009 | Ferren ................. A61B 5/0031 600/549 |
| 2009/0292194 A1 | 11/2009 | Libbus et al. |
| 2009/0295548 A1 | 12/2009 | Ronkka |
| 2009/0296677 A1 | 12/2009 | Mahany |
| 2009/0301925 A1 | 12/2009 | Alloro et al. |
| 2009/0303920 A1 | 12/2009 | Mahany |
| 2009/0306633 A1 | 12/2009 | Trovato et al. |
| 2009/0312619 A1 | 12/2009 | Say et al. |
| 2009/0318303 A1 | 12/2009 | Delamarche et al. |
| 2009/0318761 A1 | 12/2009 | Rabinovitz |
| 2009/0318779 A1 | 12/2009 | Tran |
| 2009/0318783 A1 | 12/2009 | Rohde |
| 2009/0318793 A1 | 12/2009 | Datta |
| 2010/0001841 A1 | 1/2010 | Cardullo |
| 2010/0006585 A1 | 1/2010 | Flowers et al. |
| 2010/0010330 A1 | 1/2010 | Rankers |
| 2010/0015584 A1 | 1/2010 | Singer et al. |
| 2010/0033324 A1 | 2/2010 | Shimizu et al. |
| 2010/0036269 A1* | 2/2010 | Ferren ................. A61B 5/02007 600/504 |
| 2010/0049004 A1 | 2/2010 | Edman et al. |
| 2010/0049006 A1 | 2/2010 | Magar |
| 2010/0049012 A1 | 2/2010 | Dijksman et al. |
| 2010/0049069 A1 | 2/2010 | Tarassenko et al. |
| 2010/0049263 A1 | 2/2010 | Reeve |
| 2010/0056878 A1 | 3/2010 | Partin |
| 2010/0056891 A1 | 3/2010 | Say et al. |
| 2010/0056939 A1 | 3/2010 | Tarassenko et al. |
| 2010/0057041 A1 | 3/2010 | Hayter |
| 2010/0062709 A1 | 3/2010 | Kato |
| 2010/0063438 A1 | 3/2010 | Bengtsson |
| 2010/0063841 A1 | 3/2010 | D'Ambrosia et al. |
| 2010/0069002 A1 | 3/2010 | Rong |
| 2010/0069717 A1 | 3/2010 | Hafezi et al. |
| 2010/0082367 A1 | 4/2010 | Hains et al. |
| 2010/0099967 A1 | 4/2010 | Say et al. |
| 2010/0099968 A1 | 4/2010 | Say et al. |
| 2010/0099969 A1 | 4/2010 | Say et al. |
| 2010/0100077 A1 | 4/2010 | Rush |
| 2010/0100078 A1 | 4/2010 | Say et al. |
| 2010/0100237 A1 | 4/2010 | Ratnakar |
| 2010/0106001 A1 | 4/2010 | Say et al. |
| 2010/0118853 A1 | 5/2010 | Godfrey |
| 2010/0131434 A1 | 5/2010 | Magent et al. |
| 2010/0139672 A1 | 6/2010 | Kroll et al. |
| 2010/0160742 A1 | 6/2010 | Seidl et al. |
| 2010/0168659 A1 | 7/2010 | Say et al. |
| 2010/0179398 A1 | 7/2010 | Say et al. |
| 2010/0183199 A1 | 7/2010 | Smith et al. |
| 2010/0185055 A1 | 7/2010 | Robertson et al. |
| 2010/0191073 A1 | 7/2010 | Tarassenko et al. |
| 2010/0203394 A1 | 8/2010 | Bae et al. |
| 2010/0210299 A1 | 8/2010 | Gorbachov |
| 2010/0217100 A1 | 8/2010 | LeBoeuf et al. |
| 2010/0222652 A1 | 9/2010 | Cho |
| 2010/0228113 A1 | 9/2010 | Solosko |
| 2010/0233026 A1 | 9/2010 | Ismagliov et al. |
| 2010/0234706 A1 | 9/2010 | Gilland |
| 2010/0234715 A1 | 9/2010 | Shin |
| 2010/0234914 A1 | 9/2010 | Shen |
| 2010/0245091 A1 | 9/2010 | Singh |
| 2010/0249541 A1 | 9/2010 | Geva et al. |
| 2010/0249881 A1 | 9/2010 | Corndorf |
| 2010/0256461 A1 | 10/2010 | Mohamedali |
| 2010/0259543 A1 | 10/2010 | Tarassenko et al. |
| 2010/0268048 A1 | 10/2010 | Say et al. |
| 2010/0268049 A1 | 10/2010 | Say et al. |
| 2010/0268050 A1 | 10/2010 | Say et al. |
| 2010/0268288 A1 | 10/2010 | Hunter et al. |
| 2010/0274111 A1 | 10/2010 | Say et al. |
| 2010/0280345 A1 | 11/2010 | Say et al. |
| 2010/0280346 A1 | 11/2010 | Say et al. |
| 2010/0280366 A1* | 11/2010 | Arne ...................... A61B 5/046 600/425 |
| 2010/0295694 A1 | 11/2010 | Kauffman et al. |
| 2010/0297640 A1 | 11/2010 | Kumar et al. |
| 2010/0298650 A1 | 11/2010 | Moon et al. |
| 2010/0298668 A1 | 11/2010 | Hafezi et al. |
| 2010/0298730 A1 | 11/2010 | Tarassenko et al. |
| 2010/0299155 A1 | 11/2010 | Findlay et al. |
| 2010/0311482 A1 | 12/2010 | Lange |
| 2010/0312188 A1* | 12/2010 | Robertson ............ A61B 5/0006 604/156 |
| 2010/0312577 A1 | 12/2010 | Goodnow et al. |
| 2010/0312580 A1 | 12/2010 | Tarassenko et al. |
| 2010/0332443 A1 | 12/2010 | Gartenberg |
| 2011/0004079 A1 | 1/2011 | Al Ali et al. |
| 2011/0009715 A1 | 1/2011 | O'Reilly et al. |
| 2011/0021983 A1 | 1/2011 | Jurson |
| 2011/0029622 A1 | 2/2011 | Walker et al. |
| 2011/0040203 A1 | 2/2011 | Savage et al. |
| 2011/0050431 A1 | 3/2011 | Hood et al. |
| 2011/0054265 A1 | 3/2011 | Hafezi et al. |
| 2011/0065983 A1 | 3/2011 | Hafezi et al. |
| 2011/0077660 A1 | 3/2011 | Janik et al. |

(56) References Cited

U.S. PATENT DOCUMENTS

| | | |
|---|---|---|
| 2011/0081860 A1 | 4/2011 | Brown et al. |
| 2011/0105864 A1 | 5/2011 | Robertson et al. |
| 2011/0112686 A1 | 5/2011 | Nolan et al. |
| 2011/0124983 A1 | 5/2011 | Kroll et al. |
| 2011/0134906 A1 | 6/2011 | Garudadri et al. |
| 2011/0144470 A1 | 6/2011 | Mazar et al. |
| 2011/0160549 A1* | 6/2011 | Saroka .................. A61B 5/00 600/301 |
| 2011/0166937 A1 | 7/2011 | Bangera et al. |
| 2011/0196454 A1 | 8/2011 | Strand et al. |
| 2011/0212782 A1 | 9/2011 | Thompson et al. |
| 2011/0224912 A1 | 9/2011 | Bhavaraju et al. |
| 2011/0230732 A1 | 9/2011 | Edman et al. |
| 2011/0237924 A1 | 9/2011 | McGusty et al. |
| 2011/0270112 A1 | 11/2011 | Manera et al. |
| 2011/0270135 A1 | 11/2011 | Dooley et al. |
| 2011/0279963 A1 | 11/2011 | Kumar et al. |
| 2012/0004520 A1 | 1/2012 | Whitworth et al. |
| 2012/0011699 A1 | 1/2012 | Hafezi et al. |
| 2012/0016231 A1 | 1/2012 | Westmoreland |
| 2012/0024889 A1 | 2/2012 | Robertson et al. |
| 2012/0029307 A1 | 2/2012 | Paquet et al. |
| 2012/0029309 A1 | 2/2012 | Paquet et al. |
| 2012/0032816 A1 | 2/2012 | Cho et al. |
| 2012/0332778 | 2/2012 | Nakano et al. |
| 2012/0059257 A1 | 3/2012 | Duck et al. |
| 2012/0062371 A1 | 3/2012 | Radivojevic et al. |
| 2012/0071743 A1* | 3/2012 | Todorov .............. G06F 19/3481 600/372 |
| 2012/0083715 A1 | 4/2012 | Yuen et al. |
| 2012/0089000 A1 | 4/2012 | Bishay et al. |
| 2012/0101396 A1 | 4/2012 | Solosko et al. |
| 2012/0109112 A1 | 5/2012 | Strand et al. |
| 2012/0116184 A1 | 5/2012 | Shieh |
| 2012/0179004 A1 | 7/2012 | Roesicke et al. |
| 2012/0197144 A1 | 8/2012 | Christ et al. |
| 2012/0214140 A1 | 8/2012 | Brynelson et al. |
| 2012/0245043 A1 | 9/2012 | England |
| 2012/0265544 A1 | 10/2012 | Hwang et al. |
| 2012/0299723 A1 | 11/2012 | Hafezi et al. |
| 2012/0310070 A1 | 12/2012 | Kumar et al. |
| 2012/0316413 A1 | 12/2012 | Liu et al. |
| 2013/0002423 A1 | 1/2013 | Robertson et al. |
| 2013/0030259 A1 | 1/2013 | Thomsen et al. |
| 2013/0030366 A1 | 1/2013 | Robertson et al. |
| 2013/0057385 A1 | 3/2013 | Murakami et al. |
| 2013/0060115 A1 | 3/2013 | Gehman et al. |
| 2013/0073312 A1 | 3/2013 | Thompson et al. |
| 2013/0129869 A1 | 5/2013 | Hafezi et al. |
| 2013/0129872 A1 | 5/2013 | Kruger |
| 2013/0144132 A1 | 6/2013 | Hafezi et al. |
| 2013/0171596 A1 | 7/2013 | French |
| 2013/0172690 A1 | 7/2013 | Arne et al. |
| 2013/0185228 A1 | 7/2013 | Dresner |
| 2013/0196012 A1 | 8/2013 | Dill |
| 2013/0199662 A1 | 8/2013 | Gebbink |
| 2013/0223028 A1 | 8/2013 | Arne et al. |
| 2013/0231188 A1 | 9/2013 | Berberich et al. |
| 2013/0238647 A1 | 9/2013 | Thompson |
| 2013/0328416 A1 | 12/2013 | Whitworth et al. |
| 2013/0338452 A1 | 12/2013 | Robertson et al. |
| 2014/0004492 A1 | 1/2014 | O'Reilly et al. |
| 2014/0039445 A1 | 2/2014 | Austin et al. |
| 2014/0051965 A1 | 2/2014 | Zdeblick et al. |
| 2014/0066726 A1 | 3/2014 | Costello |
| 2014/0066734 A1 | 3/2014 | Zdeblick |
| 2014/0179221 A1 | 6/2014 | Whitworth et al. |
| 2014/0180202 A1 | 6/2014 | Zdeblick et al. |
| 2014/0203950 A1 | 7/2014 | Zdeblick et al. |
| 2014/0280125 A1 | 9/2014 | Bhardwaj et al. |
| 2014/0300490 A1 | 10/2014 | Kotz et al. |
| 2014/0308930 A1 | 10/2014 | Tran |
| 2014/0315170 A1 | 10/2014 | Ionescu et al. |
| 2014/0334575 A1 | 11/2014 | Arne et al. |
| 2014/0349256 A1 | 11/2014 | Connor |
| 2014/0374276 A1* | 12/2014 | Guthrie .............. G01N 33/48792 205/777.5 |
| 2015/0048929 A1 | 2/2015 | Robertson et al. |
| 2015/0051465 A1 | 2/2015 | Robertson et al. |
| 2015/0080677 A1 | 3/2015 | Thompson et al. |
| 2015/0080678 A1 | 3/2015 | Frank et al. |
| 2015/0080679 A1 | 3/2015 | Frank et al. |
| 2015/0080680 A1 | 3/2015 | Zdeblick et al. |
| 2015/0080681 A1 | 3/2015 | Hafezi et al. |
| 2015/0112243 A1 | 4/2015 | Hafezi et al. |
| 2015/0127738 A1 | 5/2015 | Thompson et al. |
| 2015/0131764 A1 | 5/2015 | Kushner et al. |
| 2015/0149375 A1 | 5/2015 | Thompson et al. |
| 2015/0150480 A1 | 6/2015 | Zdeblick et al. |
| 2015/0164746 A1 | 6/2015 | Costello et al. |
| 2015/0165313 A1 | 6/2015 | Thompson et al. |
| 2015/0171924 A1 | 6/2015 | Zdeblick |
| 2015/0173646 A1 | 6/2015 | Berkman et al. |
| 2015/0182170 A1 | 7/2015 | Zdeblick et al. |
| 2015/0182463 A1 | 7/2015 | Hafezi et al. |
| 2015/0193593 A1 | 7/2015 | Zdeblick et al. |
| 2015/0223751 A1 | 8/2015 | Zdeblick et al. |
| 2015/0230728 A1 | 8/2015 | Hafezi et al. |
| 2015/0230729 A1 | 8/2015 | Zdeblick et al. |
| 2015/0248833 A1 | 9/2015 | Arne et al. |
| 2015/0352343 A1 | 12/2015 | Hafezi et al. |
| 2015/0361234 A1 | 12/2015 | Hafezi et al. |
| 2016/0033667 A1 | 2/2016 | Schmidt et al. |
| 2016/0106339 A1 | 4/2016 | Behzadi et al. |
| 2016/0155316 A1 | 6/2016 | Hafezi et al. |
| 2016/0226697 A1 | 8/2016 | Kushner et al. |
| 2016/0261441 A1 | 9/2016 | Fleming et al. |
| 2016/0324442 A1 | 11/2016 | Zdeblick et al. |
| 2016/0345906 A1 | 12/2016 | Johnson et al. |
| 2017/0000179 A1 | 1/2017 | Cheng et al. |
| 2017/0000180 A1 | 1/2017 | Arne et al. |
| 2017/0014046 A1 | 1/2017 | Hafezi et al. |
| 2017/0020182 A1 | 1/2017 | Schmidt et al. |
| 2017/0215761 A1 | 8/2017 | Zdeblick |
| 2017/0216569 A1 | 8/2017 | Hafezi et al. |
| 2017/0265813 A1 | 9/2017 | Zdeblick et al. |
| 2017/0270779 A1 | 9/2017 | Zdeblick et al. |
| 2017/0274194 A1 | 9/2017 | Robertson et al. |
| 2017/0290513 A1 | 10/2017 | O'Reilly et al. |
| 2017/0296799 A1 | 10/2017 | Hafezi et al. |
| 2017/0303818 A1 | 10/2017 | Behzadi et al. |
| 2018/0026680 A1 | 1/2018 | Shirvani et al. |
| 2018/0096547 A1 | 4/2018 | Robertson et al. |
| 2018/0110441 A1 | 4/2018 | Frank et al. |

FOREIGN PATENT DOCUMENTS

| | | |
|---|---|---|
| CN | 1650844 | 8/2005 |
| CN | 2748032 | 12/2005 |
| CN | 1991868 | 7/2007 |
| CN | 101005470 | 7/2007 |
| CN | 101032396 | 9/2007 |
| CN | 201076456 | 6/2008 |
| CN | 101524267 | 9/2009 |
| CN | 101795202 | 8/2010 |
| DE | 10313005 | 10/2004 |
| EP | 0344939 | 12/1989 |
| EP | 0526166 | 2/1993 |
| EP | 0981152 | 2/2000 |
| EP | 1199670 | 4/2002 |
| EP | 1246356 | 10/2002 |
| EP | 1342447 | 9/2003 |
| EP | 1530224 | 5/2005 |
| EP | 1534054 | 5/2005 |
| EP | 1702553 | 9/2006 |
| EP | 1098591 | 1/2007 |
| EP | 1789128 | 5/2007 |
| EP | 1244308 | 12/2007 |
| EP | 2063535 | 5/2009 |
| EP | 2143369 | 1/2010 |
| GB | 827762 | 2/1960 |
| GB | 2432862 | 6/2007 |
| IL | 172917 | 6/2010 |
| JP | S6117949 | 1/1986 |

(56) References Cited

FOREIGN PATENT DOCUMENTS

| | | |
|---|---|---|
| JP | 61072712 | 4/1986 |
| JP | S62112529 | 5/1987 |
| JP | S63280393 | 11/1988 |
| JP | H01285247 | 11/1989 |
| JP | 05-228128 | 9/1993 |
| JP | H0884779 | 4/1996 |
| JP | 09-330159 | 12/1997 |
| JP | 1014898 | 1/1998 |
| JP | H11195415 | 7/1999 |
| JP | 2000506410 | 5/2000 |
| JP | 2001070267 | 3/2001 |
| JP | 2001078974 | 3/2001 |
| JP | 2001198096 | 7/2001 |
| JP | 2002224053 | 8/2002 |
| JP | 2002263185 | 9/2002 |
| JP | 2002282218 | 10/2002 |
| JP | 2002282219 | 10/2002 |
| JP | 2002291684 | 10/2002 |
| JP | 2003050867 | 2/2003 |
| JP | 2003210395 | 7/2003 |
| JP | 3454525 | 10/2003 |
| JP | 2003325440 | 11/2003 |
| JP | 20047187 | 1/2004 |
| JP | 2004007187 | 1/2004 |
| JP | 2004507188 | 3/2004 |
| JP | 2004134384 | 4/2004 |
| JP | 2004274452 | 9/2004 |
| JP | 2004313242 | 11/2004 |
| JP | 2004318534 | 11/2004 |
| JP | 2004364016 | 12/2004 |
| JP | 2005031840 | 2/2005 |
| JP | 2005073886 | 3/2005 |
| JP | 2005087552 | 4/2005 |
| JP | 2005102959 | 4/2005 |
| JP | 2005304880 | 4/2005 |
| JP | 2005124708 | 5/2005 |
| JP | 2005514966 | 5/2005 |
| JP | 2005137683 | 6/2005 |
| JP | 2005148021 | 6/2005 |
| JP | 2005152037 | 6/2005 |
| JP | 2005287691 | 10/2005 |
| JP | 2005532841 | 11/2005 |
| JP | 2005532849 | 11/2005 |
| JP | 2005343515 | 12/2005 |
| JP | 20055332328 | 12/2005 |
| JP | 2006006377 | 1/2006 |
| JP | 2006508752 | 3/2006 |
| JP | 2006509574 | 3/2006 |
| JP | 2006136405 | 6/2006 |
| JP | 2006-187611 | 7/2006 |
| JP | 2006177699 | 7/2006 |
| JP | 2006278091 | 10/2006 |
| JP | 2006346000 | 12/2006 |
| JP | 3876573 | 1/2007 |
| JP | 2007151809 | 6/2007 |
| JP | 2007159631 | 6/2007 |
| JP | 2007167448 | 7/2007 |
| JP | 2007200739 | 8/2007 |
| JP | 2007313340 | 12/2007 |
| JP | 2007330677 | 12/2007 |
| JP | 2008011865 | 1/2008 |
| JP | 2008501415 | 1/2008 |
| JP | 2008086390 | 4/2008 |
| JP | 2008176434 | 7/2008 |
| JP | 2008191110 | 8/2008 |
| JP | 2008191955 | 8/2008 |
| JP | 2008212488 | 9/2008 |
| JP | 2008289724 | 12/2008 |
| JP | 2009034345 | 2/2009 |
| JP | 2009-061236 | 3/2009 |
| JP | 2009050541 | 3/2009 |
| JP | 2009514870 | 4/2009 |
| JP | 2009528909 | 8/2009 |
| JP | 2010049490 | 3/2010 |
| JP | 2011086027 | 4/2011 |
| JP | 2011519583 | 7/2011 |
| JP | 2012212362 | 11/2012 |
| KR | 20020015907 | 3/2002 |
| KR | 20020061744 | 7/2002 |
| KR | 200600977523 | 7/2006 |
| KR | 927471 | 11/2009 |
| KR | 100927471 | 11/2009 |
| KR | 20110137001 | 12/2011 |
| KR | 10-2012-09995 | 9/2012 |
| TW | 200301864 | 7/2003 |
| TW | 553735 | 9/2003 |
| TW | 200406192 | 5/2004 |
| TW | 200724094 | 7/2007 |
| TW | 200812556 | 3/2008 |
| TW | 200916136 | 4/2009 |
| TW | 201120673 | 6/2011 |
| WO | WO1988002237 | 4/1988 |
| WO | WO1992021307 | 12/1992 |
| WO | WO1993008734 | 5/1993 |
| WO | WO1993019667 | 10/1993 |
| WO | WO1994001165 | 1/1994 |
| WO | WO1995016393 | 6/1995 |
| WO | WO1997014112 | 4/1997 |
| WO | WO1997039963 | 10/1997 |
| WO | WO1998043537 | 10/1998 |
| WO | WO1999037290 | 7/1999 |
| WO | WO1999059465 | 11/1999 |
| WO | WO2000032474 | 6/2000 |
| WO | WO2000033246 | 6/2000 |
| WO | WO2001000085 | 1/2001 |
| WO | WO2001047466 | 7/2001 |
| WO | WO2001049364 | 7/2001 |
| WO | WO2001058236 | 8/2001 |
| WO | WO2001074011 | 10/2001 |
| WO | WO2001080731 | 11/2001 |
| WO | WO2002000920 | 1/2002 |
| WO | WO0235997 | 5/2002 |
| WO | WO2002045489 | 6/2002 |
| WO | WO2002058330 | 7/2002 |
| WO | WO2002062276 | 8/2002 |
| WO | WO2002087681 | 11/2002 |
| WO | WO2002095351 | 11/2002 |
| WO | WO2003005877 | 1/2003 |
| WO | WO2003050643 | 6/2003 |
| WO | WO2003068061 | 8/2003 |
| WO | WO2004014225 | 2/2004 |
| WO | WO2004019172 | 3/2004 |
| WO | WO2004039256 | 5/2004 |
| WO | WO2004059551 | 7/2004 |
| WO | WO2004066833 | 8/2004 |
| WO | WO2004066834 | 8/2004 |
| WO | WO2004066903 | 8/2004 |
| WO | WO2004068748 | 8/2004 |
| WO | WO2004068881 | 8/2004 |
| WO | WO2004075032 | 9/2004 |
| WO | WO2004075751 | 9/2004 |
| WO | WO2004109316 | 12/2004 |
| WO | WO2004110555 | 12/2004 |
| WO | WO2005011237 | 2/2005 |
| WO | WO2005013503 | 2/2005 |
| WO | WO2005020023 | 3/2005 |
| WO | WO2005024687 | 3/2005 |
| WO | WO2005041438 | 5/2005 |
| WO | WO2005041767 | 5/2005 |
| WO | WO2005046575 | 5/2005 |
| WO | WO2005047837 | 5/2005 |
| WO | WO2005051166 | 6/2005 |
| WO | WO2005053517 | 6/2005 |
| WO | WO2005055448 | 6/2005 |
| WO | WO2005069887 | 8/2005 |
| WO | WO2005082436 | 9/2005 |
| WO | WO2005083621 | 9/2005 |
| WO | WO2005084533 | 9/2005 |
| WO | WO2005110238 | 11/2005 |
| WO | WO2005117697 | 12/2005 |
| WO | WO2005123569 | 12/2005 |
| WO | WO2006009404 | 1/2006 |
| WO | WO2006016370 | 2/2006 |
| WO | WO2006021932 | 3/2006 |

(56) References Cited

FOREIGN PATENT DOCUMENTS

| | | |
|---|---|---|
| WO | WO2006027586 | 3/2006 |
| WO | WO2006028347 | 3/2006 |
| WO | WO2006035351 | 4/2006 |
| WO | WO2006037802 | 4/2006 |
| WO | WO2006046648 | 5/2006 |
| WO | WO2006055892 | 5/2006 |
| WO | WO2006055956 | 5/2006 |
| WO | WO2006066566 | 6/2006 |
| WO | WO2006075016 | 7/2006 |
| WO | WO2006094513 | 9/2006 |
| WO | WO2006100620 | 9/2006 |
| WO | WO2006104843 | 10/2006 |
| WO | WO2006109072 | 10/2006 |
| WO | WO2006/123346 | 11/2006 |
| WO | WO2006116718 | 11/2006 |
| WO | WO2006119345 | 11/2006 |
| WO | WO2006127355 | 11/2006 |
| WO | WO2007001724 | 1/2007 |
| WO | WO2007001742 | 1/2007 |
| WO | WO2007013952 | 2/2007 |
| WO | WO2007014084 | 2/2007 |
| WO | WO2007014527 | 2/2007 |
| WO | WO2007021496 | 2/2007 |
| WO | WO2007027660 | 3/2007 |
| WO | WO2007028035 | 3/2007 |
| WO | WO2007036687 | 4/2007 |
| WO | WO2007036741 | 4/2007 |
| WO | WO2007036746 | 4/2007 |
| WO | WO2007040878 | 4/2007 |
| WO | WO2007067054 | 6/2007 |
| WO | WO2007071180 | 6/2007 |
| WO | WO2007096810 | 8/2007 |
| WO | WO2007101141 | 9/2007 |
| WO | WO2007115087 | 10/2007 |
| WO | WO2007120946 | 10/2007 |
| WO | WO2007123923 | 11/2007 |
| WO | WO2007127316 | 11/2007 |
| WO | WO2007127455 | 11/2007 |
| WO | WO2007127879 | 11/2007 |
| WO | WO2007127945 | 11/2007 |
| WO | WO2007128165 | 11/2007 |
| WO | WO2007130491 | 11/2007 |
| WO | WO2007133526 | 11/2007 |
| WO | WO2007143535 | 12/2007 |
| WO | WO2007149546 | 12/2007 |
| WO | WO2008002239 | 1/2008 |
| WO | WO2008008281 | 1/2008 |
| WO | WO2008012700 | 1/2008 |
| WO | WO2008030482 | 3/2008 |
| WO | WO2008039030 | 4/2008 |
| WO | WO2008052136 | 5/2008 |
| WO | WO2008061138 | 5/2008 |
| WO | WO2008063626 | 5/2008 |
| WO | WO2008066617 | 6/2008 |
| WO | WO2008068695 | 6/2008 |
| WO | WO2008076464 | 6/2008 |
| WO | WO2008085131 | 7/2008 |
| WO | WO2008089232 | 7/2008 |
| WO | WO2008091683 | 7/2008 |
| WO | WO2008095183 | 8/2008 |
| WO | WO2008097652 | 8/2008 |
| WO | WO2008101107 | 8/2008 |
| WO | WO2008112577 | 9/2008 |
| WO | WO2008112578 | 9/2008 |
| WO | WO2008120156 | 10/2008 |
| WO | WO2008133394 | 11/2008 |
| WO | WO2008134185 | 11/2008 |
| WO | WO2008150633 | 12/2008 |
| WO | WO2009000447 | 12/2008 |
| WO | WO2009001108 | 12/2008 |
| WO | WO2009005759 | 1/2009 |
| WO | WO2009006615 | 1/2009 |
| WO | WO2009022343 | 2/2009 |
| WO | WO2009029453 | 3/2009 |
| WO | WO2009031149 | 3/2009 |
| WO | WO2009032381 | 3/2009 |
| WO | WO2009035773 | 3/2009 |
| WO | WO2009036334 | 3/2009 |
| WO | WO2009051829 | 4/2009 |
| WO | WO2009051830 | 4/2009 |
| WO | WO2009063377 | 5/2009 |
| WO | WO2009081348 | 7/2009 |
| WO | WO2009111664 | 9/2009 |
| WO | WO2009146082 | 12/2009 |
| WO | WO2010003175 | 1/2010 |
| WO | WO2010009100 | 1/2010 |
| WO | WO2010011833 | 1/2010 |
| WO | WO2010019778 | 2/2010 |
| WO | WO2010057049 | 5/2010 |
| WO | WO2010075115 | 7/2010 |
| WO | WO2010080765 | 7/2010 |
| WO | WO2010080843 | 7/2010 |
| WO | WO2010105053 | 9/2010 |
| WO | WO2010107563 | 9/2010 |
| WO | WO2010107980 | 9/2010 |
| WO | WO2010115194 | 10/2010 |
| WO | WO2010129288 | 11/2010 |
| WO | WO2010132331 | 11/2010 |
| WO | WO2010135516 | 11/2010 |
| WO | WO2011024560 | 3/2011 |
| WO | WO2011068963 | 6/2011 |
| WO | WO2011133799 | 10/2011 |
| WO | WO2011159336 | 12/2011 |
| WO | WO2011159337 | 12/2011 |
| WO | WO2011159338 | 12/2011 |
| WO | WO2011159339 | 12/2011 |
| WO | WO2012104657 | 8/2012 |
| WO | WO2012112561 | 8/2012 |
| WO | WO2012158190 | 11/2012 |
| WO | WO2013012869 | 1/2013 |
| WO | WO2015042411 | 3/2015 |
| WO | WO2015044722 | 4/2015 |
| WO | WO2015112603 | 7/2015 |
| WO | WO2015112604 | 7/2015 |
| WO | WO2015119911 | 8/2015 |

OTHER PUBLICATIONS

Philips Respironics Products, Noninvasive Technology to Help Your Studies Succeed. 510 (k) Permanent Notification for Vital Sense. Apr. 22, 2004; http/minimitter.com/products.cfm.
Sharma, et al., "The Future is Wireless: Advances in Wireless Diagnostic and Therapeutic Technologies in Gastoenterology," Gastroenterology, Elesevier, Philadelphia, PA, vol. 137, No. 2, Aug. 1, 2009, pp. 434-439.
AADE, "AADE 37th Annual Meeting San Antonio Aug. 4-7, 2010" American Association of Diabetes Educators Aug. 2010; http://www.diabeteseducator.org/annualmeeting/2010/index.html; 2 pp.
Arshak et al., A Review and Adaptation of Methods of Object Tracking to Telemetry Capsules IC-Med; Jan. 2007 vol. 1, No. 1, Issue 1, 12pp.
"ASGE Technology Status Evaluation Report: wireless capsule endoscopy" American Soc. For Gastrointestinal Endoscopy; Apr. 2006 vol. 63, No. 4; 7 pp.
Aydin et al., "Design and implementation considerations for an advanced wireless interface in miniaturized integrated sensor Microsystems" Sch. of Eng. & Electron., Edinburgh Univ., UK; Sep. 2003; Abstract Only.
Barrie, Heidelberg pH capsule gastric analysis. Texbook of Natural Medicine, (1992), Pizzorno, Murray & Barrie.
Baskiyar, S. "A Real-time Fault Tolerant Intra-body Network" Dept. of Comp. Sci & Soft Eng; Auburn University; Proceedings of the 27th Annual IEEE Conference; 0742-1303/02 (2002) IEEE; 6 pp.
Bohidar et al., "Dielectric Behavior of Gelatin Solutions and Gels" Colloid Polym Sci (1998) 276:81-86.
Brock, "Smart Medicine: The Application of Auto-ID Technology to Healthcare" Auto-ID Labs (2002) http://www.autoidlabs.org/uploads/media/MIT-AUTOID-WH-010.pdf.
Carlson et al., "Evaluation of a non-invasive respiratory monitoring system for sleeping subjects" Physiological Measurement (1999) 20(1): 53.

(56) References Cited

OTHER PUBLICATIONS

Consolvo, Sunny et al., "Design Requirement for Technologies that Encourage Physical Activity," CHI 2006 Proceedings, Designing for Tangible Interactions, Apr. 22, 2006, Montreal, Quebec, Canada, pp. 457-466.
Coury, L. "Conductance Measurement Part 1: Theory"; Current Separations, 18:3 (1999) p. 91-96.
Description of ePatch Technology Platform for ECG and EMG, located it http://www.madebydelta.com/imported/images/DELTA_Web/documents/ME/ePatch_ECG_EMG.pdf, Dated Sep. 2, 2010.
Delvaux et al., "Capsule endoscopy: Technique and indications" Clinical Gastoenterology; Oct. 2008 vol. 22, Issue 5, 1pp. (Abstract Only).
Dhar et al., "Electroless nickel plated contacts on porous silicon" Appl. Phys. Lett. 68 (10) pp. 1392-1393 (1996).
Eldek A., "Design of double dipole antenna with enhanced usable bandwidth for wideband phased array applications" Progress in Electromagnetics Research PIER 59, 1-15 (2006).
Evanczuk, S., "PIC MCU software library uses human body for secure communications link" ; EDN Network; edn.com; Retrieved from internet Jun. 19, 2013 at http://www.edn.com/electronics-products/other/4407842/PIC-MCU-software-library-uses-human-body-for-secure-communications-link; Feb. 26, 2013; 5 pp.
Fawaz et al., "Enhanced Telemetry System using CP-QPSK Band-Pass Modulation Technique Suitable for Smart Pill Medical Application" IFIP IEEE Dubai Conference Apr. 2008; http://www.asic.fh-offenburg.de/downloads/ePille/IFIP_IEEE_Dubai_Conference.pdf.
Ferguson et al., "Dialectric Constant Studies III Aqueous Gelatin Solutions" J. Chem. Phys. 2, 94 (1934) p. 94-98.
Furse C. M., "Dipole Antennas" J. Webster (ed). Wiley Encyclopedia of Electrical and Electronics Engineering (1999) p. 575-581.
Gaglani S. "Put Your Phone, or Skin, on Vibrate" MedGadget; Mar. 2012 http://medgadget.com/2012/03/put-your-phone-or-skin-on-vibrate.html 8pp.
Gilson, D.R. "Molecular dynamics simulation of dipole interactions", Department of Physics, Hull University, Dec. 2002, p. 1-43.
Given Imaging, "Agile Patency Brochure" (2006) http://www.inclino.no/documents/AgilePatencyBrochure_Global_GMB-0118-01.pdf; 4pp.
Gonzalez-Guillaumin et al., "Ingestible capsule for impedance and pH monitoring in the esophagus" IEEE Trans Biomed Eng; Dec. 2007 54(12) 1pp. (Abstract Only).
Greene, "Edible RFID microchip monitor can tell if you take your medicine" Bloomberg Businessweek; Mar. 2010 2 pp.; http://www.businessweek.com/idg/2010-03-31/edible-rfid-microchip-monitor-can-tell-if-you-take-your-medicine.html.
Halthion Medical Technologies "Providing Ambulatory Medical Devices Which Monitor, Measure and Record" webpage. Online website: http://www.halthion.com/; downloaded May 30, 2012; 2 pp.
Heydari et al., "Analysis of the PLL jitter due to power/ground and substrate noise"; IEEE Transactions on Circuits and Systems (2004) 51(12): 2404-16.
Hoeksma, J. "New 'smart pill' to track adherence" E-Health-Insider; http://www.e-health-insider.com/news/5910/new_'smart_pill'_monitors_medicines; May 17, 2010 (2010); 1pp.
Hoover et al., "Rx for health: Engineers design pill that signals it has been swallowed" University of Florida News; Mar. 2010 2pp.; http://news.ufl.edu/2010/03/31/antenna-pill-2/.
Hotz "The Really Smart Phone" The Wall Street Journal, What They Know (2011); 6 pp.; http://online.wsj.com/article/SB10001424052748704547604576263261679848814.html?mod=djemTECH_t.
Intromedic, MicroCam Innovative Capsule Endoscope Pamphlet. (2006) 8 pp (http://www.intromedic.com/en/product/productinfo.asp).
ISFET—Ion Sensitive Field-Effect Transistor; MICROSENS S.A. pdf document, 4 pages.

Jimbo et al., "Gastric-fluid-utilized micro battery for micro medical devices" The Sixth International Workshop on Micro and Nanotechnology for Power Geneartion and Energy Conservation Applications, (2006) pp. 97-100.
Jung, S. "Dissolvable 'Transient Electronics' Will Be Good for Your Body and the Environment" MedGadget; Oct. 1, 2012; Onlne website: http://medgadget.com/2012/10/dissolvable-transient-electronics-will-be-good-for-your-body-and-the-environment.html; downloaded Oct. 24, 2012; 4 pp.
Juvenile Diabetes Research Foundation International (JDRF), "Artificial Pancreas Project" Jun. 2010; http://www.artificialpancreasproject.com/; 3 pp.
Kamada K., "Electrophoretic deposition assisted by soluble anode" Materials Letters 57 (2003) 2348-2351.
Kendle, Earl R. and Morris, Larry A., "Preliminary Studies in the Development of a Gastric Battery for Fish" (1964). Nebraska Game and Parks Commission White Papers, Conference Presentations, & Manuscripts. Paper 22. p. 1-6.
Kim et al., "A Semi-Interpenetrating Network System for a Polymer Membrane"; Eur. Polym. J. vol. 33 No. 7; pp. 1009-1014 (1997).
Li, P-Y, et al. "An electrochemical intraocular drug delivery device", Sensors and Actuators A 143; p. 41-48.; Jul. 2007.
Lifescan, "OneTouch UltraLink™" http://www.lifescan.com/products/meters/ultralink; Jul. 2010 2 pp.
Lin et al., "Do Physiological Data Relate to Traditional Usability Indexes?" Proceedings of OZCHI 2005, Canberra, Australia (2005) 10 pp.
Mackay et al., "Radio Telemetering from within the Body" Inside Information is Revealed by Tiny Transmitters that can be Swallowed or Implanted in Man or Animal Science (1991) 1196-1202; 134; American Association for the Advancement of Science, Washington D.C.
Mackay et al., "Endoradiosonde" Nature, (1957) 1239-1240, 179 Nature Publishing Group.
Mandryk et al., "A physiological approach for continuously modeling user emotion in interactive play environments" Proceedings of Measuring Behavior (2008) (Maastrichtm The Netherlands, Aug. 26-29) 2 pp.
Mandryk et al., "Objectively Evaluating Entertainment Technology" Simon Fraser University; CHI (2004) ACM 1-58113-703-6/04/0004; 2 pp.
McKenzie et al., "Validation of a new telemetric core temperature monitor" J. Therm. Biol. (2004) 29(7-8):605-11.
Medtronic, "CareLink Therapy Management Software for Diabetes" Jul. 2010; https://carelink.minimed.com/patient/entry.jsp?bhcp=1; 1 pp.
Medtronic, "Carelink™ USB" (2008) http://www.medtronicdiabetes.com/pdf/carelink_usb_factsheet.pdf 2pp.
Medtronic "The New MiniMed Paradigm® REAL-Time Revel™ System" Aug. 2010 http://www.medtronicdiabetes.com/products/index.html; 2 pp.
Medtronic, "Mini Med Paradigm® Revel™ Insulin Pump" Jul. 2010 http://www.medtronicdiabetes.com/products/insulinpumps/index.html; 2 pp.
Medtronic, Mini Med Paradigm™ Veo™ System: Factsheet (2010). http://www.medtronic-diabetes.com.au/downloads/Paradigm%20Veo%20Factsheet.pdf ; 4 pp.
Melanson, "Walkers swallow RFID pills for science" Engadget; Jul. 2008; http://www.engadget.com/2008/07/29/walkers-swallow-rfid-pills-for-science.
Minimitter Co. Inc. "Actiheart" Traditional 510(k) Summary. Sep. 27, 2005.
Minimitter Co. Inc. Noninvasive technology to help your studies succeed. Mini Mitter.com Mar. 31, 2009.
Mini Mitter Co, Inc. 510(k) Premarket Notification Mini-Logger for Diagnostic Spirometer. Sep. 21, 1999.
Mini Mitter Co, Inc. 510(k) Premarket Notification for VitalSense. Apr. 22, 2004.
Minimitter Co. Inc. VitalSense Integrated Physiological Monitoring System. Product Description. Jul. 2005.
Minimitter Co. Inc. VitalSense Wireless Vital Signs Monitoring. Temperatures.com, Mar. 31, 2009.

(56) References Cited

OTHER PUBLICATIONS

Mojaverian et al., "Estimation of gastric residence time of the Heidelberg capsule in humans: effect of varying food composition" Gastroenterology (1985) 89:(2): 392-7.
O'Brien et al., "The Production and Characterization of Chemically Reactive Porous Coatings of Zirconium Via Unbalanced Magnetron Sputtering" Surface and Coatings Technology (1996) 86-87; 200-206.
Owano, N., "Study proposes smart sutures with sensors for wounds" phys.org. Aug. 2012. http://phys.org/news/2012-08-smart-sutures-sensors-wounds.html; 2pp.
"PALO Bluetooth Baseband" PALO Bluetooth Resource Center; Retrieved from internet Dec. 12, 2012 at URL:http://palowireless.com/bluearticles/baseband.asp; 6pp.
Park, "Medtronic to Buy MiniMed for $3.7 Billion" (2001) HomeCare; http://homecaremag.com/mag/medical_medtronic_buy_minimed/; 2 pp.
Platt, D., "Modulation and Deviation" AE6EO, Foothills Amateur Radio Society; Oct. 26, 2007; 61 pp.
Radio Antennae, http://www.erikdeman.de/html/sail018h.htm; (2008) 5 pages.
"RFID "pill" monitors marchers" RFID News; Jul. 2008 http://www.rfidnews.org/2008/07/23/rfid-pill-monitors-marchers/.
Rolison et al., "Electrically conductive oxide aerogels: new materials in electrochemistry" J. Mater. Chem. (2001) 1, 963-980.
Roulstone, et al., "Studies on Polymer Latex Films: I. A study of latex film morphology" Polymer International 24 (1991) pp. 87-94.
Sanduleanu et al., "Octave tunable, highly linear, RC-ring oscillator with differential fine-coarse tuning, quadrature outputs and amplitude control for fiber optic transceivers" (2002) IEEE MTT-S International Microwave Symposium Digest 545-8.
Santini, J.T. et al, "Microchips as controlled drug delivery-devices", Agnew. Chem. Int. Ed. (2000), vol. 39, p. 2396-2407.
"SensiVida minimally invasive clinical systems" Investor Presentation Oct. 2009 28pp; http://www.sensividamedtech.com/SensiVidaGeneralOctober09.pdf.
Shawgo, R.S. et al. "BioMEMS from drug delivery", Current Opinion in Solid State and Material Science 6; May 2002, p. 329-334.
Shin et al., "A Simple Route to Metal Nanodots and Nanoporous Metal Films"; Nano Letters, vol. 2, No. 9 (2002) pp. 933-936.
Shrivas et al., "A New Platform for Bioelectronics-Electronic Pill", Cummins College, (2010).; http://www.cumminscollege.org/downloads/electronics_and_telecommunication/Newsletters/Current%20Newsletters.pdf.
"Smartlife awarded patent for knitted transducer" Innovation in Textiles News: http://www.innovationintextiles.com/articles/208.php; 2pp. Aug. 2009.
"The SmartPill Wireless Motility Capsule" Smartpill, The Measure of GI Health; May 2010 http://www.smartpillcorp.com/index.cfm?pagepath=Products/The_SmartPill_Capsule&id=17814.
Solanas et al., "RFID Technology for the Health Care Sector" Recent Patents on Electrical Engineering (2008) 1, 22-31.
Soper, S.A. et al. "Bio-Mems Technologies and Applications", Chapter 12, "MEMS for Drug Delivery", p. 325-346 (2007).
Swedberg, "University Team Sees Ingestible RFID Tag as a Boon to Clinical Trials" RFID Journal Apr. 27, 2010; http://www.rfidjournal.com/article/view/7560/1 3pp.
Tajalli et al., "Improving the power-delay performance in subthreshold source-coupled logic circuits" Integrated Circuit and System Design. Power and Timing Modeling, Optimization and Simulation, Springer Berlin Heidelberg (2008) 21-30.
Tatbul et al., "Confidence-based data management for personal area sensor networks" ACM International Conference Proceeding Series (2004) 72.
Tierney, M.J. et al "Electroreleasing Composite Membranes for Delivery of Insulin and other Biomacromolecules", J. Electrochem. Soc., vol. 137, No. 6, Jun. 1990, p. 2005-2006.

Trutag, Technologies, Inc., Spectral Microtags for Authentication and Anti-Counterfeiting; "Product Authentication and Brand Protection Solutions"; http://www.trutags.com/; downloaded Feb. 12, 2013 (2013); 1 pp.
Walkey, "MOSFET Structure and Processing"; 97.398* Physical Electronics Lecture 20.
Watson, et al., "Determination of the relationship between the pH and conductivity of gastric juice" Physiol Meas. 17 (1996) pp. 21-27.
Whipple, Fred L.; "Endoradiosonde," Nature, Jun. 1957, 1239-1240.
Winter, J. et al. "The material properties of gelatin gels"; USA Ballistic Research Laboratories, Mar. 1975, pp. 1-157.
Wongmanerod et al., "Determination of pore size distribution and surface area of thin porous silicon layers by spectroscopic ellipsometry" Applied Surface Science 172 (2001) 117-125.
Xiaoming et al., "A telemedicine system for wireless home healthcare based on bluetooth and the internet" Telemedicine Journal and e-health (2004) 10(S2): S110-6.
Yang et al., "Fast-switching frequency synthesizer with a discriminator-aided phase detector" IEEE Journal of Solid-State Circuits (2000) 35(10): 1445-52.
Yao et al., "Low Power Digital Communication in Implantable Devices Using Volume Conduction of Biological Tissues" Proceedings of the 28th IEEE, EMBS Annual International Conference, Aug. 30-Sep. 3, 2006.
Zimmerman, "Personal Area Networks: Near-field intrabody communication" IBM Systems Journal (1996) 35 (3-4):609-17.
Zworkin, "A Radio Pill" Nature, (1957) 898, 179 Nature Publishing Group.
Ferguson et al., "Wireless communication with implanted medical devices using the conductive properties of the body," Expert Rev Med Devices, Jul. 2011, 8(4): 427-433.
Aronson, J., "Meyer's Side Effects of Cardiovascular Drugs," Elsevier, Mar. 2, 2009, Medical , 840 pages. (Not Attached).
Au-Yeung, K., et al., "A Networked System for Self-Management of Drug Therapy and Wellness", Wireless Health '10, Oct. 5-7, 2010, San Diego, 9 pages.
Bergogne C., et al., "A new frequency estimator applied to burst transmission", IEEE International Conference on Acoustics, Speech and Signal Processing, Apr. 21, 1997, vol. 1, pp. 267-270.
Herbig, S.M., "Asymmetric-membrane tablet coatings for osmotic drug delivery", Journal of Controlled Release 35 (1995) 127-136.
Lee, K. B.; "Two-step activation of paper batteries for high power generation: design and fabrication of biofluid- and wateractivated paper batteries"; J. Micromech. Microeng. 16 (2006) 2312-2317.
Lee, K. B.; "Urine-activated paper batteries for Biosystems"; J. Micromech. Microeng. 15 (2005) S21 O-S214.
McDermott-Wells, P., "What is Bluetooth?", IEEE Potentials, IEEE, New York, NY, vol. 23, No. 5, Dec. 1, 2004, pp. 33-35.
Sammoura, F. et al., "Water-activated disposable and long shelf life microbatteries", Sensors and Actuators A 111 (2004) 79-86.
VonStetten, F. et al., "Biofuel cells as power generation for implantable devices", Pore. Eurosensors XX, (2006), pp. 22-225.
Wang, X. et al "Resistance to Tracking and Erosion of Silicone Rubber Material under Various Types of Precipitation", Jpn. J. Appl. Phys. vol. 38 (1999) pp. 5170-5175.
Target Innovations, Tablet Metal Detector, https ://web. arch ive.org/web/20 1 30215063351/http://www. metaldetectorindia.com/tablet -metal-detector. html, Feb. 15, 2013.
TargetPharmaceutical Metal Detector, Feb. 15, 2013 downloaded from Target Innovations, Tablet Metal Detector, Feb. 15, 2013.
Youtube video Pharmaceutical Metal Detector/Tablet Metal Detector/ Capsule Metal Detector/ Dry Fruits; https://www.youtube.com/watch?v=I0126txam_s, May 12, 2012.
Chan, Adrian D.C., et al.,; "Wavelet Distance Measure for Person Identification Using Electrocardiograms," IEEE Transactions on Instrumentation and Measurement, IEEE Service Center, Piscataway, NJ, US, vol. 57, No. 2, Feb. 1, 2008, pp. 248-253.
Zhang, Y-T. et al., "Wireless Biomedical Sensing," Wiley Encyclopedia of Biomedical Engineering, 2006, pp. 1-9.

\* cited by examiner

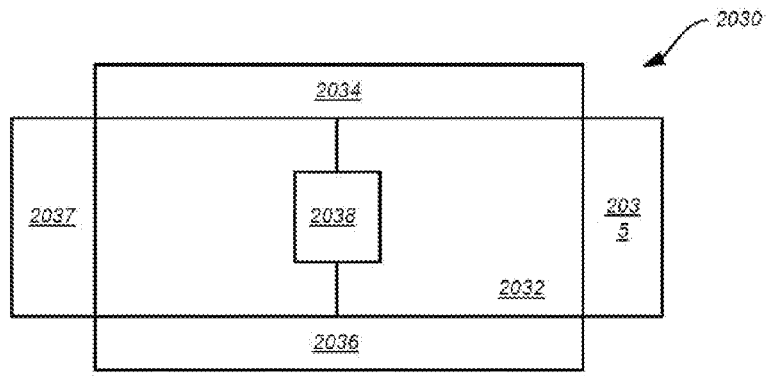
FIG. 7
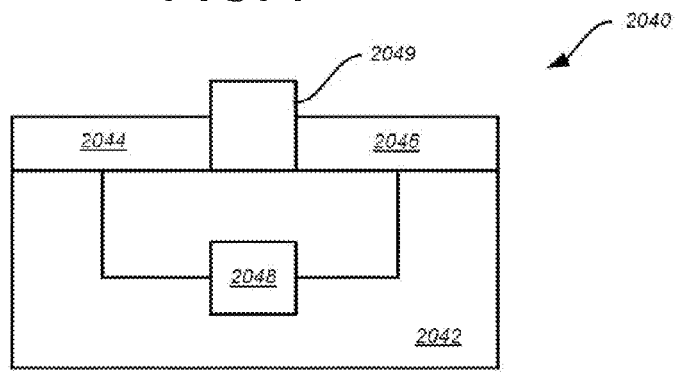
FIG. 8
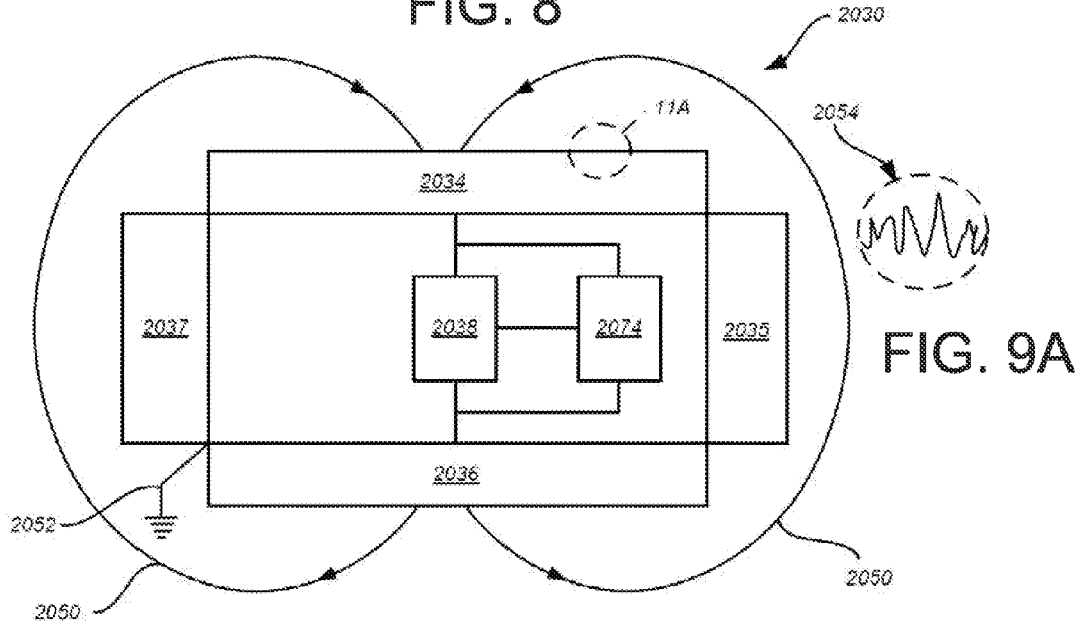
FIG. 9
FIG. 9A

SOCIAL MEDIA NETWORKING BASED ON PHYSIOLOGIC INFORMATION

CROSS-REFERENCE TO RELATED APPLICATION

This application claims the benefit of U.S. Provisional Patent Application Ser. No. 61/899,704 entitled SOCIAL MEDIA NETWORKING BASED ON PHYSIOLOGIC INFORMATION, filed on Nov. 4, 2013, which is herein entirely incorporated by reference.

INTRODUCTION

The present disclosure is related generally to social-networking system based alone or in part on physiologic information. The physiologic information is provided to the social-networking system via a personal body-associated communicator worn by a user. The personal communicator includes sensors and has the capability to detect physiologic parameters associated with the user. The body-associated personal communicator also is capable of detecting ingestion events based on ingestible event marker technology.

A social-networking system, which may include a social-networking system website, enable its users (such as persons or organizations) to interact with it and with each other. The social-networking system may, with input from a user, create and store user profiles associated with the users. A user profile may include demographic information, communication-channel information, and information on personal interests of the user. The social-networking system also may, with input from a user, create and store a record of relationships between the user and other users of the social-networking system. The social-networking system also may provide services (e.g., wall posts, photo-sharing, event organization, messaging, games, or advertisements) to facilitate social interaction between or among users.

The social-networking system may transmit over one or more networks content or messages related to its services to a mobile or other computing device associated with a user. A user also may install software applications on a mobile or other computing device of the user for accessing a user profile of the user and other data within the social-networking system. The social-networking system may generate a personalized set of content objects to display to a user, such as a newsfeed of aggregated stories of other users connected to the user.

A mobile computing device—such as a smartphone, tablet computer, or laptop computer—may include functionality for determining its location, direction, or orientation, such as a GPS receiver, compass, or gyroscope. Such a device may also include functionality for wireless communication, such as BLUETOOTH™ communication, near-field communication (NFC), or infrared (IR) communication or communication with wireless local area networks (WLANs) or cellular-telephone network. Such a device may also include one or more cameras, scanners, touchscreens, microphones, or speakers. Mobile computing devices also may execute software applications, such as games, web browsers, or social-networking applications. With social-networking applications, users may connect, communicate, and share information with other users in their social networks.

Social-media technologies take on many different forms including magazines, Internet forums, weblogs, social blogs, microblogging, wikis, social networks, podcasts, photographs or pictures, video, rating and social bookmarking. Technologies include blogging, picture-sharing, vlogs, wall-posting, music-sharing, crowdsourcing and voice over IP, to name a few. Social network aggregation can integrate many of the platforms in use.

When social media is used in combination with mobile devices it is called mobile social media. This is a group of mobile marketing applications that allow the creation and exchange of user-generated content. Due to the fact that mobile social media runs on mobile devices, it differentiates from traditional social media as it incorporates new factors such as the current location of the user (location-sensitivity) or the time delay between sending and receiving messages (time-sensitivity).

SUMMARY

In one aspect, this disclosure is directed to providing access to social-network systems based on physiologic information of individual users associated with the social-network system. In a particular embodiment, a client system receives physiologic and/or ingestion information from a physiologic sensing platform associated with the individual users as described herein. A wireless access point may receive a request from the client system to access a network through the wireless access point using the physiologic and/or ingestion information. For example, the physiologic sensing platform may acquire physiologic information associated with a user and may connect to the client system. The physiologic sensing platform may include a receiver in the form of a body-associated personal communicator configured to detect physiologic parameters associated with the user, ingestion events, and/or provided two-way wireless communication to/from the client system. The client system may include, for example, a desktop computer, in-car computer, game console, handheld game console, laptop, notebook, palmtop, tablet computer, smartphone, smartbook, and PDA (personal digital assistant), programmable calculator, among others. The client device connects to a wired and/or wireless access point and attempts to access the Internet through Wi-Fi provided by the wireless access point. The access point may send an identifier associated with the client system and/or the physiologic information and/or ingestion information associated with the user to the social-networking system. The social-networking system may include user profiles arranged in any organized manner and in one aspect, at least one social graph that stores relationships between the user profiles based on the physiologic and/or ingestion information. The social-networking system may determine whether network access (e.g., Wi-Fi) should be provided to the client system based on the identifier associated with the client system and/or physiologic information and/or ingestion information associated with the user based upon a user profile of the social-networking system. The social-networking system may then send the determination to the wireless access point. The social-networking system may provide network access to the client system in accordance with the determination by the social-networking system.

In one aspect, a method is provided for receiving physiologic information at a social-networking system from a body-associated personal communicator.

In another aspect, a social-networking system is provided. The social-networking system is configured to receive physiological information from a body-associated personal communicator.

In yet another aspect, a body-associated personal communicator is provided. The body-associated personal communicator is configured to receive physiologic information and communicate the physiologic information to a social-networking system.

FIGURES

FIG. 7 is a block diagram representation of one aspect of the event indicator system with dissimilar metals positioned on opposite ends.

FIG. 8 is a block diagram representation of another aspect of the event indicator system with dissimilar metals positioned on the same end and separated by a non-conducting material.

FIG. 9 shows ionic transfer or the current path through a conducting fluid when the event indicator system of FIG. 9 is in contact with conducting liquid and in an active state.

FIG. 9A shows an exploded view of the surface of dissimilar materials of FIG. 11.

Figure 15:
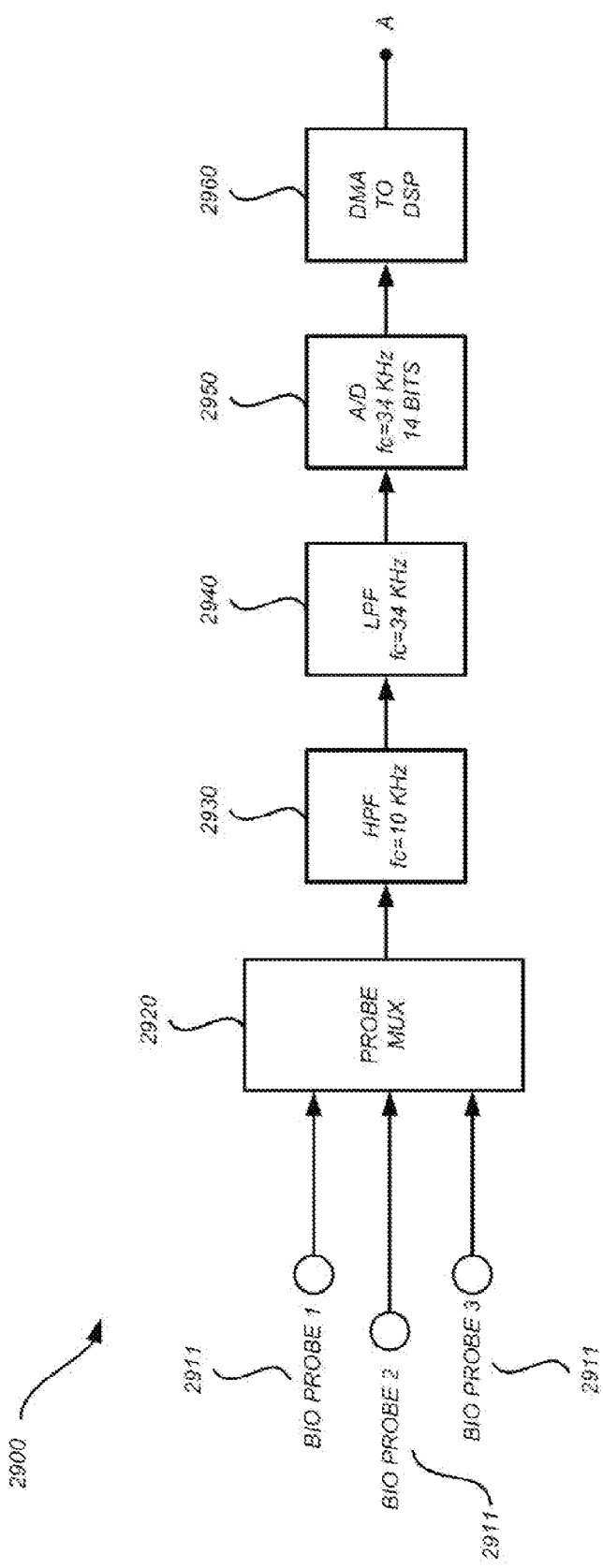

FIG. 15 provides a block diagram of a high frequency signal chain in a receiver, according to one aspect.

Figure 16:
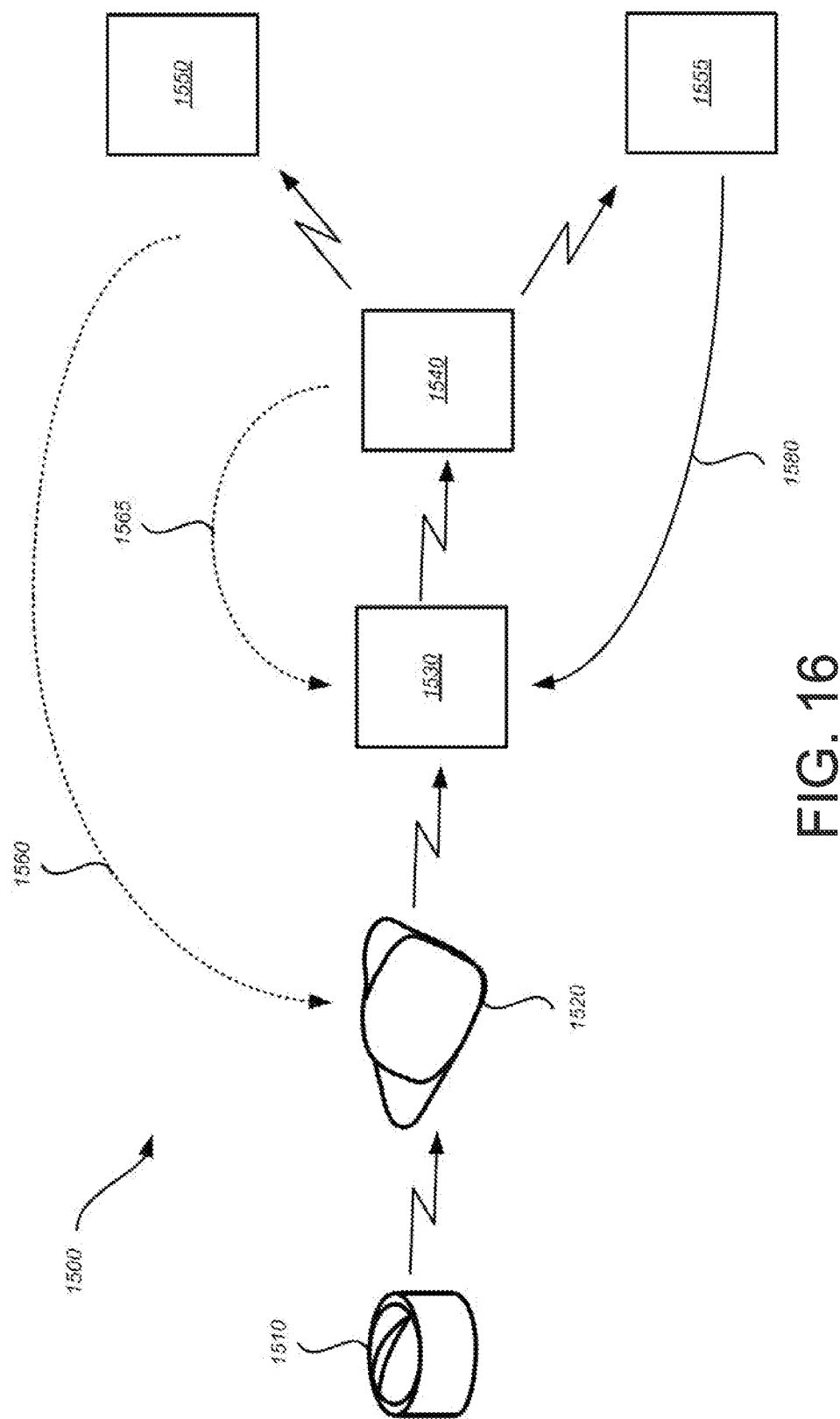

FIG. 16 provides a diagram of how a system that includes a signal receiver and an ingestible event marker may be employed, according to one aspect.

Figure 17:
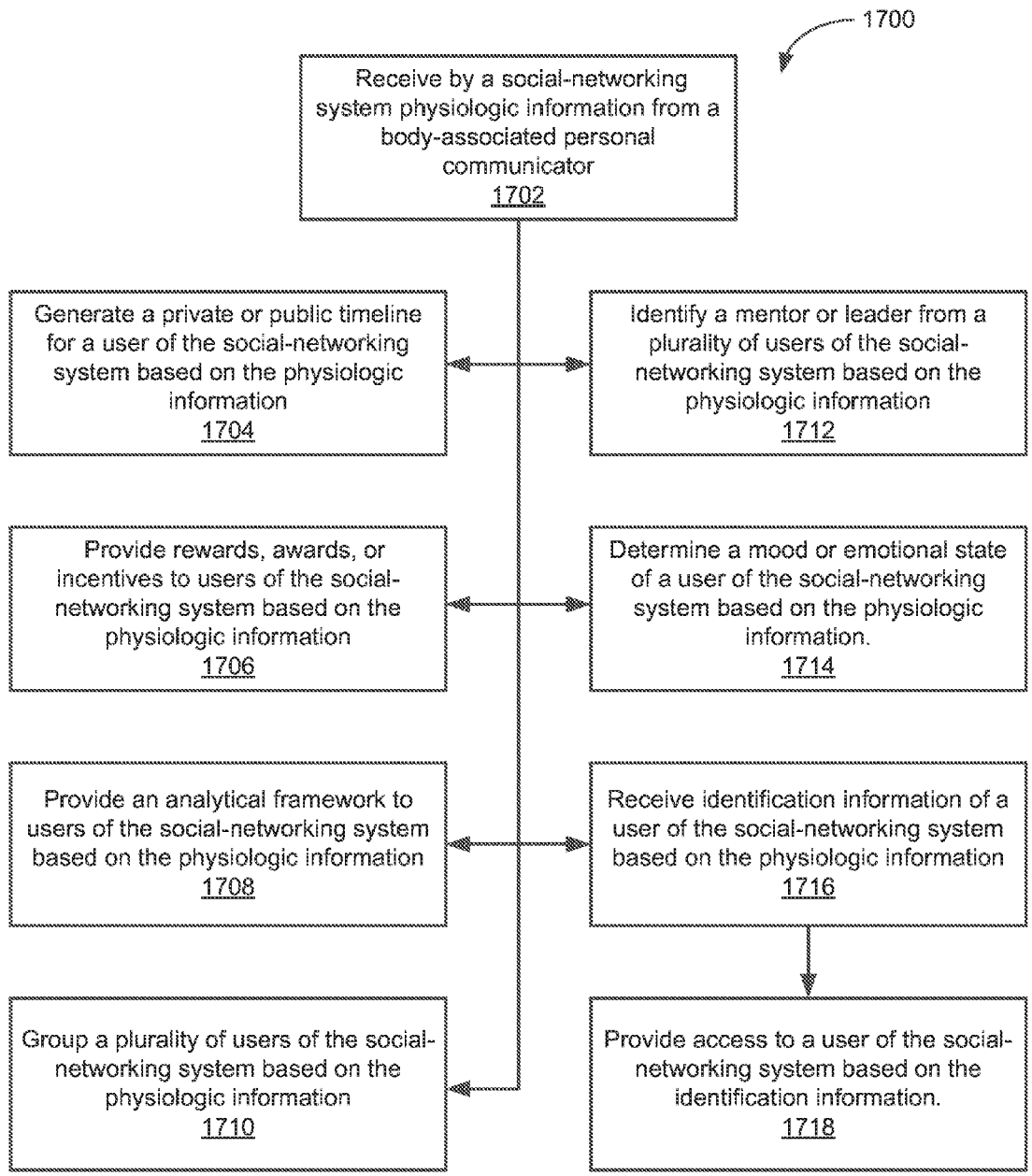

FIG. 17 is a flow diagram of a method associated with a social-networking system

DESCRIPTION

Before explaining the various aspects of a social-networking system in detail, it should be noted that the various aspects disclosed herein are not limited in their application or use to the details of construction and arrangement of parts illustrated in the accompanying drawings and description. Rather, any disclosed aspect of the social-networking system may be positioned or incorporated in other aspects, variations, and modifications thereof, and may be practiced or carried out in various ways. Accordingly, aspects of the social-networking system disclosed herein are illustrative in nature and are not meant to limit the scope or application thereof. Furthermore, unless otherwise indicated, the terms and expressions employed herein have been chosen for the purpose of describing the aspects for the convenience of the reader and are not to limit the scope thereof. In addition, it should be understood that any one or more of the disclosed aspects, expressions of aspects, and/or examples thereof, can be combined with any one or more of the other disclosed aspects, expressions of aspects, and/or examples thereof, without limitation.

In the following description, like reference characters designate like or corresponding parts throughout the several views. Also, in the following description, it is to be understood that terms such as front, back, inside, outside, top, bottom and the like are words of convenience and are not to be construed as limiting terms. Terminology used herein is not meant to be limiting insofar as devices described herein, or portions thereof, may be attached or utilized in other orientations. The various aspects will be described in more detail with reference to the drawings.

It will be appreciated that the term "medication" or "dose form" as used throughout this disclosure includes various forms of ingestible, inhalable, injectable, absorbable, or otherwise consumable medicaments and/or carriers therefor such as, for example, pills, capsules, gel caps, placebos, over capsulation carriers or vehicles, herbal, over-the-counter (OTC) substances, supplements, prescription-only medication, ingestible event markers (IEM), and the like.

In one aspect, the present specification provides a body-associated personal wearable communication devices ("body-associated personal communicator"). In one aspect, the body-associated personal communicator is in communication with a living subject. In one aspect, the body-associated personal communicator is in communication with a local node external to the body of the living subject. In one aspect, the local node is in communication with a remote node via a network and, accordingly, the living subject is able to communicate with the remote node. Information also may be communicated from the remote node and/or the local node to the living subject via the body-associated personal communicator. In various aspects, the two-way communication between the living subject and the body-associated personal communicator occurs discreetly such that the communications are non-detectable by humans. Such discreet mode of communication minimizes the intrusiveness into the living subject's sense of privacy and enhances the likelihood that the living subject will accept the personal communicator and use it in a prescribed manner.

In another aspect, the present specification provides a body-associated personal communicator that senses personal physiologic parameters of the living subject and communicates such parameters to the local node and in some aspects to the remote node. Information associated with the personal physiologic parameters also may be communicated from the remote node and/or the local node to the living subject via the body-associated personal communicator. As described above, communications between the individual and the body-associated personal communicator occurs discreetly to enhance the likelihood of acceptance of the body-associated personal communicator by the living subject.

Figure 1:
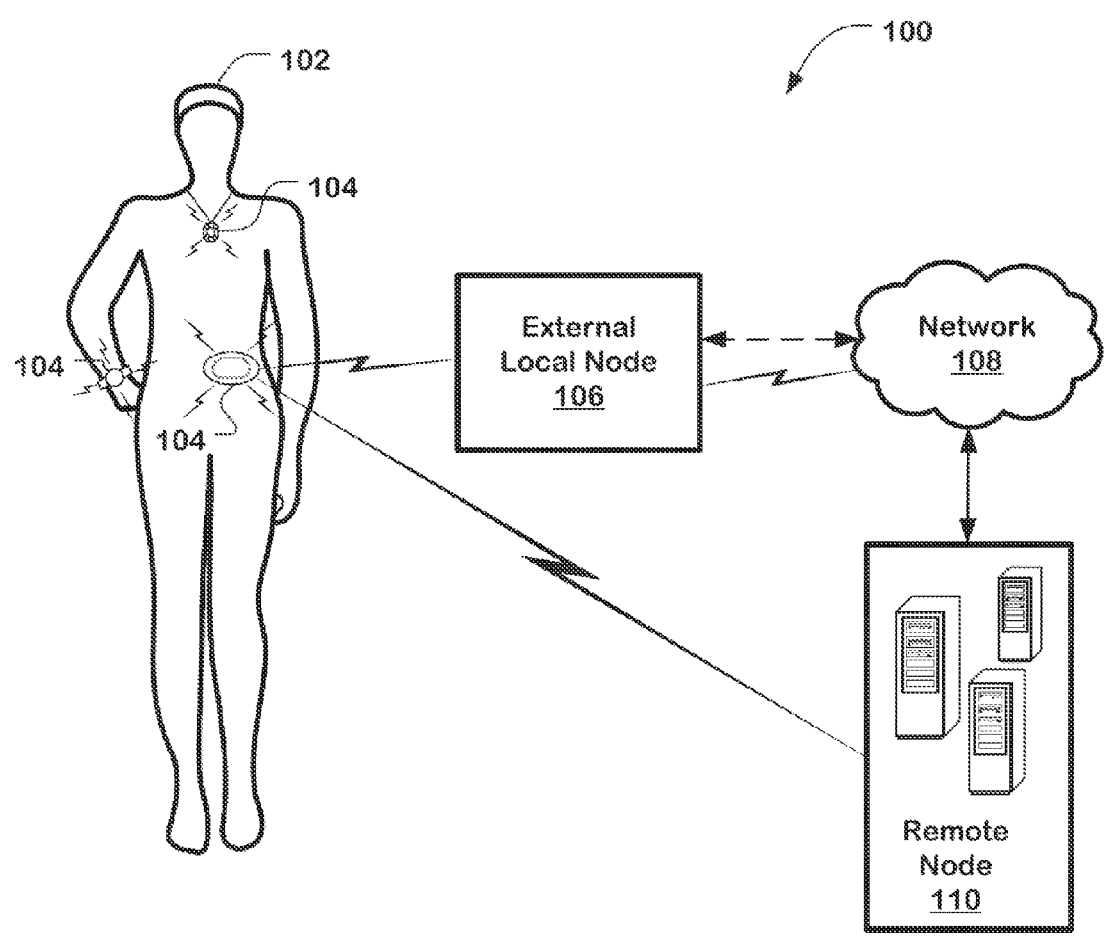
FIG. 1 illustrates one aspect of a social media personal communication system.

FIG. 1 illustrates one aspect of a social media personal communication system 100. As illustrated in FIG. 1, a receiver, otherwise referred to herein as a body-associated personal communicator 104, is positioned on a living subject 102. The living subject 102 may be a human or non-human being. In various aspects, the body-associated personal communicator 104 may be realized in many forms and configurations including sensor-enabled patches, watches, and jewelry, as shown in FIG. 1, for example, as well as a bandage with an adhesive portion, wristbands, earrings, bracelets, rings, pendants, clothing, undergarments, hats, caps, scarves, pins, accessories, belts, shoes, eyeglasses, contact lenses, hearing-aides, subcutaneous implants, and other devices that are wearable, implantable, or semi-implantable on or in the living subject 102 without limitation. The body-associated personal communicator 104 is configured to communicate with the living subject 102 and an external local node 106. The external local node 106 is configured to communicate with a remote node 110 via a network 108. In one aspect, the body-associated personal communicator 104 is configured to communicate with the remote node 110 directly. It will be appreciated that in the context of the present disclosure, communication is intended to encompass communications to and from the personal communicator 104 and the external local node 106. Likewise, communication is intended to encompass communications to and from the body-associated personal communicator 104 and the remote node 110 as well as communications to and from the external local node 106 and the remote node 110.

The body-associated personal communicator 104 may comprise any number of distinct physiologic parameter or biomarker collecting and/or sensing capabilities. The number of distinct parameters or biomarker collecting and/or sensing capabilities may vary e.g., one or more, two or more, three or more, four or more, five or more, ten or more, and so on. In certain configurations, the body-associated personal communicator 104 comprises one or more active components that are able to dynamically monitor and record individual physiologic parameters and/or biomarkers associated with the living subject 102. Such components include, without limitation, sensors, electronic recording devices, processors, memory, communication components. In one aspect, the body-associated personal communicator 104 may include an on-board battery to supply electrical power to the active components. The physiologic parameter or biomarker sensing abilities may include sensing cardio-data, including heart rate, electrocardiogram (ECG), and the like, respiration rate, temperature, pressure, chemical composition of fluid, e.g., analyte in blood, fluid state, blood flow rate, physical activity, sleep, accelerometer motion data, without limitation, for example.

In one aspect, the body-associated personal communicator 104 provides specific information about the physiologic state of the subject 102. In another aspect, some of this information may be derived from sensors embedded in the body-associated personal communicator 104. The subject 102 may obtain the body-associated personal communicator 104 with a prescription, for example, and then wear the body-associated personal communicator 104 for a prescribed period, e.g., hours, days, weeks, months, years.

In one aspect, the body-associated personal communicator 104 includes, is configured to (a) monitor and record individual physiology, e.g., physical activity, heart rate, respiration, temperature, sleep, fluidics information, etc., of the living subject 102 and (b) communicate these parameters beyond the body of the living subject 102 to other client devices, e.g., mobile phones, computers, internet servers, etc., in order to (c) enable support and collaboration for fitness, wellbeing, disease management, sport, entertainment, gaming, social goals and other applications on a social media platform. A challenge for such body-associated personal communicators 104 is creating a compelling rationale for the individual 102 to wear or use the body-associated personal communicator 104 on a continuous basis—for example, to apply an adhesive bandage-based body-associated personal communicator 104 to their skin for weeks, months and potentially years and accept the possibility of its inconveniences and limitations, such as (i) potential skin irritation, (ii) the burden of frequent application and removal, and (iii) a feeling of intrusiveness into the wearer's daily life. An opportunity for the personal communicator 104 is to exploit fundamental "intimacy" advantages they have over other sensor-enabled and communication devices that are not worn on or in the body—a body-associated personal communicator 104 interface with the individual 102 is by definition highly personal and tangible, with the ability to have private, communication between the individual and the personal communicator (leveraging physical, tactile "body language" or other signals), where the communication is substantially undetectable by others. In this manner, the body-associated personal communicator 104 may enable product and service possibilities not feasible with other approaches. The body language opportunity seeks to overcome at least some of the challenges and burdens of the body-associated personal communicator 104 to create a compelling rationale to make the body-associated personal communicator 104 as indispensable to a consumer as the mobile phone as an extension of their mind and body. In one aspect, discreet communications between the body-associated personal communicator 104 and the living subject 102 can be auditory via a small earpiece placed inside the ear canal, or visual via images projected on specialized eye glasses worn by living subject 102. In other aspects, discreet modes of communication between the living subject 102 and the personal communicator 104 include, without limitation, visual, auditory, vibratory, tactile, olfactory, and taste as described in the form of illustrative examples hereinbelow.

In one aspect, the body-associated personal communicator 104, for example a sensor patch that adheres to the skin of an individual such as the living subject 102, communicates with its wearer by sending and receiving tactile or other signals. The default settings may be modified such that the body-associated personal communicator 104 discreetly vibrates or pulses in a specific manner or pattern, e.g., time or space based, to remind the subject 102 of important events or to communicate important personalized messages to the wearer. The default settings also may be modified such that the subject 102 can transmit and record meaningful inputs and messages to the body-associated personal communicator 104 by communicating a simple language of finger taps, jiggles, scratches or other physical inputs initiated by the subject 102. Through the body-associated personal communicator 104 communications architecture, e.g., a BLUETOOTH™ or other communication links to other devices beyond the body, the composite set of sensed physiology, tactile inputs, and outputs can be transmitted to other individuals, groups, caregivers, and related products, e.g., online games, of the subject's 102 choosing via the external local node 106, network 108, and/or the remote node 110. The features of the body-associated personal communicator 104 are based on a sustained behavior change mechanism and it increases the value and potential of body-associated personal communicators 104 and the likelihood that consumers will seek out, use, and benefit from such body-associated personal communicators 104.

In-body communications include any communication of data or information via the body of the living subject 102, i.e., communication via or associated with inter-body aspects, intra-body aspects, and a combination of the same. For example, inter-body aspects include communications associated with devices designed to attach to a body surface. Intra-body aspects include communications associated with data generated from within the body, e.g., by the body itself or by a device implanted, ingested, or otherwise locatable in, or partially in, the body. For example, intra-body communications are disclosed in the U.S. Provisional Patent Application No. 61/251,088, the entire content of which is hereby incorporated by reference.

Communications include and/or may be associated with software, hardware, circuitry, various devices, and combinations thereof.

The devices include devices associated with physiologic data generation, transmission, reception, communication. The devices further include various implantable, ingestible, insertable, and/or attachable devices associated with the human body or other living organisms. The devices still further include multimedia devices such as telephones, stereos, audio players, PDAs, handheld devices, and multimedia players.

The system for incorporating physiologic data enables exchange, transmission, receipt, manipulation, management, storage, and other activities and events related to physiologic data. Such activities and events may be contained within the system for incorporating physiologic data, partially integrated with the system for incorporating physiologic data, or associated with externalities, e.g., activities, systems, components, and the like which are external to the system for incorporating physiologic data.

The physiologic data environment includes any source of information or data, including remote computer systems, local computer devices. The information or data may comprise physiologic data in whole or in part, e.g., aggregated or generated with other types of data. The physiologic data may be pure or refined, e.g., physiologic data from which inferences are drawn.

As shown in FIG. 1, the body-associated personal communicator 104, regardless of form factor or implementation is in communication with an external local node 106. In one aspect, the body-associated personal communicator 104 includes the capability of communicating, e.g., receiving, transmitting, generating, and recording data directly or indirectly from the living subject 102. Although the data may include physiologic data, it is not limited as such. Any data of a physiologic nature may be associated with the living subject 102. The physiologic data may include, for example, heart rate, heart rate variability, respiration rate, body temperature, temperature of local environment, three-axis measurement of activity and torso angle, as well as other physiologic data, metrics, inertial measurements comprising at least an accelerometer, a gyroscope, and a magnetometer, and indicators associated with one or more individuals. The physiologic data may be communicated at various times or time intervals to the external local node 106. For example, the communication may be real-time, i.e., in close temporal proximity to a time in which the physiologic data were generated, measured, ascertained, or on an historical basis, i.e., in far temporal proximity to a time in which the physiologic data was generated, measured, ascertained. In various aspects, the physiologic data may be associated with a variety of devices, e.g., cardiac device.

In one aspect, the external local node 106 may be configured as a communication hub and may include any hardware device, software, and/or communications component(s), as well as systems, subsystems, and combinations of the same which generally function to communicate physiologic and non-physiologic data between the personal communicator 104 and the external local node 106. Communication of the data includes receiving, storing, manipulating, displaying, processing, and/or transmitting the data to the remote node 110 via the network 108.

In various aspects, the external local node 106 also functions to communicate, e.g., receive and transmit, non-physiologic data. Example of non-physiologic data include gaming rules and data generated by a separate cardiac-related device such as an implanted pacemaker and communicated to the hub directly or indirectly, e.g., via the personal communicator 104.

Broad categories of external local nodes 106 include, for example, base stations, personal communication devices, handheld devices, and mobile telephones. In various aspects, the external local node 106 may be implemented as a handheld portable device, computer, mobile telephone, sometimes referred to as a smartphone, tablet personal computer (PC), kiosk, desktop computer, laptop computer, game console, or any combination thereof. Although some aspects of the external local node 106 may be described with a mobile or fixed computing device implemented as a smart phone, personal digital assistant, laptop, desktop computer by way of example, it may be appreciated that the various aspects are not limited in this context. For example, a mobile computing device may comprise, or be implemented as, any type of wireless device, mobile station, or portable computing device with a self-contained power source, e.g., battery, such as the laptop computer, ultra-laptop computer, personal digital assistant (PDA), cellular telephone, combination cellular telephone/PDA, mobile unit, subscriber station, user terminal, portable computer, handheld computer, palmtop computer, wearable computer, media player, pager, messaging device, data communication device, and so forth. A fixed computing device, for example, may be implemented as a desk top computer, workstation, client/server computer, and so forth.

The external local node 106 comprises personal communication devices including, for example, devices having communication and computer functionality and typically intended for individual use, e.g., mobile computers, sometimes referred to as "handheld devices." Base stations comprise any device or appliance capable of receiving data such as physiologic data. Examples include computers, such as desktop computers and laptop computers, and intelligent devices/appliances. Intelligent devices/appliances include consumer and home devices and appliances that are capable of receipt of data such as physiologic data. Intelligent devices/appliances may also perform other data-related functions, e.g., transmit, display, store, and/or process data. Examples of intelligent devices/appliances include refrigerators, weight scales, toilets, televisions, door frame activity monitors, bedside monitors, bed scales. Such devices and appliances may include additional functionality such as sensing or monitoring various physiologic data, e.g., weight, heart rate. Mobile telephones include telephonic communication devices associated with various mobile technologies, e.g., cellular networks.

In various aspects, the external local node 106 may provide voice and/or data communications functionality in accordance with different types of cellular radiotelephone systems. Examples of cellular radiotelephone systems may include Code Division Multiple Access (CDMA) systems, Global System for Mobile Communications (GSM) systems, North American Digital Cellular (NADC) systems, Time Division Multiple Access (TDMA) systems, Extended- TDMA (E-TDMA) systems, Narrowband Advanced Mobile Phone Service (NAMPS) systems, 3G systems such as Wide-band CDMA (WCDMA), CDMA-2000, Universal Mobile Telephone System (UMTS) systems, WiMAX (Worldwide Interoperability for Microwave Access, LTE (Long Term Evolution) and so forth.

In various embodiments, the external local node 106 may be configured to provide voice and/or data communications functionality in accordance with different types of wireless network systems or protocols. Examples of suitable wireless network systems offering data communication services may include the Institute of Electrical and Electronics Engineers (IEEE) 802.xx series of protocols, such as the IEEE 802.1a/b/g/n series of standard protocols and variants (also referred to as "WiFi"), the IEEE 802.16 series of standard protocols and variants (also referred to as "WiMAX"), the IEEE 802.20 series of standard protocols and variants, and so forth. A mobile computing device may also utilize different types of shorter range wireless systems, such as a Bluetooth system operating in accordance with the Bluetooth Special Interest Group (SIG) series of protocols, including Bluetooth Specification versions v1.0, v1.1, v1.2, v1.0, v2.0 with Enhanced Data Rate (EDR), as well as one or more Bluetooth Profiles, and so forth. Other examples may include systems using infrared techniques or near-field communication techniques and protocols, such as electromagnetic induction (EMI) techniques.

In one aspect, the external local node 106, for example, the hub, includes a software application associated with a mobile telephone of a patient. The application and mobile telephone function to receive physiologic data from a receiver, which, in turn, receives the physiologic data directly from an individual or indirectly, e.g., via a device. Examples of devices include cardiac devices and ingestible devices. The hub stores, manipulates, and/or forwards the data, alone or in combination with other data, via the network 108 to a remote node 110.

In various aspects, the external local node 106 (hub) receives, generates, communicates, and/or transmits, physiologic data, alone or in combination with other data, i.e., non-physiologic data such as ingestion information from IEMs or various sources. Communication from the external local node 106 includes any transmission means or carriers, and combinations thereof, including wireless, wired, RF, conductive, etc. as is known in the art or as may become available in the future.

In various aspects, the handheld device includes software, e.g., a software agent/application, associated with the physiologic data. In various aspects of the handheld device, the software is preconfigured, i.e., configurable by the manufacturer/retailer; configurable by the consumer, i.e., downloadable from a website; or a combination of the same.

The base station includes systems, subsystems, devices, and/or components that receive, transmit, and/or relay the physiologic data. In various aspects, the base station communicably interoperates with a receiver such as the body-associated personal communicator 104 and a communications network 108 such as the Internet. Examples of base stations are computers, e.g., servers, personal computers, desktop computers, laptop computers, intelligent devices/appliances, etc., as heretofore discussed.

In various aspects, the base station may be embodied as an integrated unit or as distributed components, e.g., a desktop computer and a mobile telephone in communication with one another and in communication with a patch receiver and the Internet.

In various aspects, the base station includes the functionality to wirelessly receive and/or wirelessly transmit data, e.g., physiologic data received from and transmitted to the body-associated personal communicator 104 and the Internet.

Further, in various aspects, the base station may incorporate and/or be associated with, e.g., communicate with, various devices. Such devices may generate, receive, and/or communicate data, e.g., physiologic data. The devices include, for example, "intelligent" devices such as gaming devices, e.g., electronic slot machines, handheld electronic games, electronic components associated with games and recreational activities.

The mobile telephone includes, for example, devices such as a short-range, portable electronic device used for mobile voice or data communication over a network of specialized cell site base stations. The mobile telephone is sometimes known as or referred to as "mobile," "wireless," "cellular phone," "cell phone," or "hand phone (HP)."

In addition to the standard voice function of a telephone, various aspects of mobile telephones may support many additional services and accessories such as short message service (SMS) for text messaging, email, packet switching for access to the Internet, Java gaming, wireless, e.g., short range data/voice communications, infrared, camera with video recorder, and multimedia messaging system (MMS) for sending and receiving photos and video. Some aspects of mobile telephones connect to a cellular network of base stations (cell sites), which is, in turn, interconnected to the public switched telephone network (PSTN) or satellite communications in the case of satellite phones. Various aspects of mobile telephones can connect to the Internet, at least a portion of which can be navigated using the mobile telephones.

In various aspects, the mobile telephone includes software, e.g., a software agent/application, associated with the physiologic data. One example is an auto refill application related to or integrated with an auto refill system to facilitate automated prescription refill functions. In various aspects of the mobile telephone, the software is preconfigured, i.e., configurable by the manufacturer/retailer; configurable by the consumer, i.e., downloadable from a website; or a combination of the same.

Further, various aspects of the hub include combinations of devices. One such combination is the body-associated personal communicator 104 in communication with the handheld device or the mobile telephone. Thus, for example, the body-associated personal communicator 104 wirelessly transmits physiologic data to the mobile telephone having a receiver and a software agent available thereon. The receiver of the mobile telephone receives the physiologic data. A software agent, e.g., an application, processes the physiologic data and displays various information related to the physiologic data via, for example, a customized graphical user interface (GUI). In various aspects, the software agent generates displays with a predetermined "look and feel," i.e., recognizable to a user as belonging to a predetermined group of software programs, GUIs, source devices, communities, gaming software, etc.

More particularly, the personal communication system 100 includes any environment having therein, or associated with, data or communication of physiologic data for a gaming or recreational purpose. Communication includes any method, act, or vehicle of communication, and/or combinations thereof. For example, communication methods include manual, wired, and wireless. Wireless technologies include radio signals, such as x-rays, ultraviolet light, the visible spectrum, infrared, microwaves, and radio waves, etc. Wireless services include voice and messaging, handheld and other Internet-enabled devices, data networking.

Vehicles of communication include the network 108. In various aspects, the network 108 comprises local area networks (LAN) as well as wide area networks (WAN) including without limitation Internet, wired channels, wireless channels, communication devices including telephones, computers, wire, radio, optical or other electromagnetic channels, and combinations thereof, including other devices and/or components capable of/associated with communicating data. For example, the communication environments include in-body communications, various devices, various modes of communications such as wireless communications, wired communications, and combinations of the same.

Wireless communication modes include any mode of communication between points that utilizes, at least in part, wireless technology including various protocols and combinations of protocols associated with wireless transmission, data, and devices. The points include, for example, wireless devices such as wireless headsets, audio and multimedia devices and equipment, such as audio players and multimedia players, telephones, including mobile telephones and cordless telephones, and computers and computer-related devices and components, such as printers.

Wired communication modes include any mode of communication between points that utilizes wired technology including various protocols and combinations of protocols associated with wired transmission, data, and devices. The points include, for example, devices such as audio and multimedia devices and equipment, such as audio players and multimedia players, telephones, including mobile telephones and cordless telephones, and computers and computer-related devices and components, such as printers.

In one aspect, the remote node 110 comprises social network systems, commercial systems, healthcare systems, pharmacy systems, university systems, financial transaction systems, web communities, physician systems, family caregiver systems, regulatory agency systems, wholesaler/retailer systems as described in U.S. patent application Ser. No. 12/522,249 titled "INGESTIBLE EVENT MARKER DATA SYSTEM," the disclosure of which is herein incorporated by reference in its entirety. In other aspects, the remote node 110 comprises state games, behavioral reflective games, psychological response games, synchronization games, actual progress games, and recreational games as described in PCT Patent Application No. PCT/US09/60713 dated Oct. 14, 2009 titled "METHOD AND SYSTEM FOR INCORPORATING PHYSIOLOGIC DATA IN A GAMING ENVIRONMENT" and published as WO 2010/045385, the disclosure of which is herein incorporated by reference in its entirety.

Figure 2:
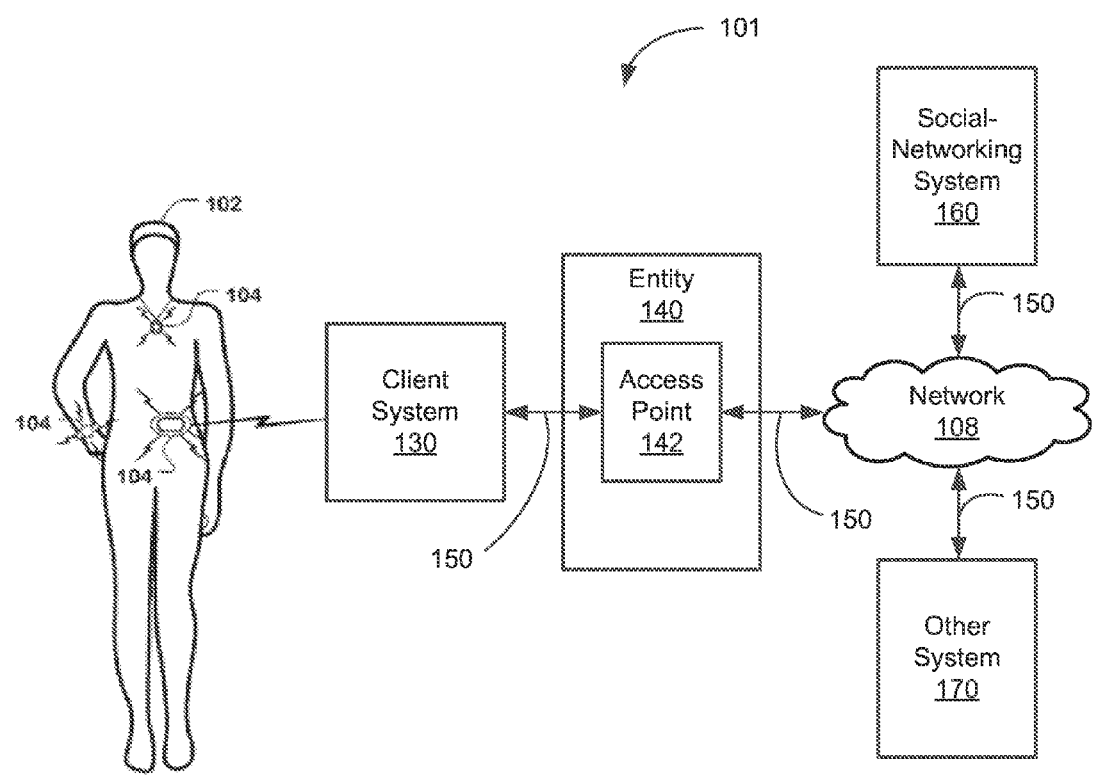
FIG. 2 illustrates an example network environment associated with a social-networking system and an access point.

FIG. 2 illustrates an example network environment 101 associated with a social-networking system 160 and a wireless access point 142. Network environment 101 includes a user 102 wearing a body-associated personal communicator 104, a client system 130, a wireless access point 142 of an entity 140, a social-networking system 160, and a third-party system 170 connected to each other by a network 108. In one aspect, the external local node 106 (FIG. 1) may be represented as client system 130 and wireless access point 142 and remote node 110 (FIG. 1) may be represented as social-networking system 160. Although FIG. 2 illustrates a particular arrangement of user 102 wearing a body-associated personal communicator 104, client system 130, wireless access point 142, social-networking system 160, third-party system 170, and network 108, this disclosure contemplates any suitable arrangement of user 101, client system 130, wireless access point 142, social-networking system 160, third-party system 170, and network 108. As an example and not by way of limitation, two or more of client system 130, wireless access point 142, social-networking system 160, and third-party system 170 may be connected to each other directly, bypassing network 108. As another example, two or more of client system 130, wireless access point 142, social-networking system 160, and third-party system 170 may be physically or logically co-located with each other in whole or in part. Moreover, although FIG. 2 illustrates a particular number of users 102 wearing a body-associated personal communicator 104, client systems 130, entities 140, wireless access points 142, social-networking systems 160, third-party systems 170, and networks 108, this disclosure contemplates any suitable number of users 102 each wearing a body-associated personal communicator 104, client systems 130, entities 140, wireless access points 142, social-networking systems 160, third-party systems 170, and networks 108. As an example and not by way of limitation, network environment 101 may include multiple users 102 each wearing a body-associated personal communicator 104, client systems 130, entities 140, wireless access points 142, social-networking systems 160, third-party systems 170, or networks 108.

In particular embodiments, user 102 wearing a body-associated personal communicator 104 may be an individual (human user) or a group of individuals each wearing a body-associated personal communicator 104 that interacts or communicates with or over other elements of network environment 101 such as devices coupled to network 108 or social-networking system 160. In particular embodiments, one or more users 102 wearing a body-associated personal communicator 104 may use one or more client systems 130 to access, send data to, and receive data from network 108, social-networking system 160, or third-party system 170. Client system 130 may access network 108, social-networking system 160, or other system for e.g., third-party system 170 directly or via a third-party system or device. As an example and not by way of limitation, client system 130 may access third-party system 170 via social-networking system 160. In particular embodiments, client system 130 may be an electronic device including hardware, software, or embedded logic components or a combination of two or more such components and capable of carrying out the appropriate functionalities implemented or supported by client system 130. As an example and not by way of limitation, a client system 130 may include a computer system such as a desktop computer, notebook or laptop computer, netbook, tablet computer, e-book reader, GPS device, camera, personal digital assistant (PDA), handheld electronic device, cellular telephone, smartphone, other suitable electronic device, or any suitable combination thereof. This disclosure contemplates any suitable client systems 130.

In particular embodiments, client system 130 may include a web browser, such as MICROSOFT INTERNET EXPLORER, GOOGLE CHROME or MOZILLA FIREFOX, and may have one or more add-ons, plug-ins, or other extensions, such as TOOLBAR or YAHOO TOOLBAR. A user at client system 130 may enter a Uniform Resource Locator (URL) or other address directing the web browser to a particular server (such as a server coupled to network 108, or a server associated with social-networking system 160 or third-party system 170), and the web browser may generate a Hyper Text Transfer Protocol (HTTP) request and communicate the HTTP request to the server. The server may accept the HTTP request and communicate to client system 130 one or more Hyper Text Markup Language (HTML) files responsive to the HTTP request. Client system 130 may render a webpage based on the HTML files from the server for presentation to the user. This disclosure contemplates any suitable webpage files. As an example and not by way of limitation, webpages may render from HTML files, Extensible Hyper Text Markup Language (XHTML) files, or Extensible Markup Language (XML) files, according to particular needs. Such pages may also execute scripts such as, for example and without limitation, those written in JAVASCRIPT, JAVA, MICROSOFT SILVERLIGHT, combinations of markup language and scripts such as AJAX (Asynchronous JAVASCRIPT and XML), and the like. Herein, reference to a webpage encompasses one or more corresponding webpage files (which a browser may use to render the webpage) and vice versa, where appropriate.

Entity 140 may represent any individual, business, or organization. Entity 140 may be associated with wireless access point 142. For example, entity 140 may own or control wireless access point 142. In particular embodiments, entity 140 is a merchant that offers free network access (e.g., to the Internet) to authorized customers via wireless access point 142. In other embodiments, entity 140 is an owner of a wireless access point 142 located at the residence or business of the owner. In particular embodiments, wireless access point 142 is operable to bridge or route data traffic between client system 130 and network 108. Wireless access point 142 may include a router, gateway, modem, a network switch, or other suitable device for providing network access to client systems 130. In particular embodiments, wireless access point 142 is capable of communicating with a plurality of client systems 130 via wired or wireless links 150. Wireless access point 142 is also capable of communicating with network 108 via link 150.

This disclosure contemplates any suitable network 108. As an example and not by way of limitation, one or more portions of network 108 may include an ad hoc network, an intranet, an extranet, a virtual private network (VPN), a local area network (LAN), a wireless LAN (WLAN), a wide area network (WAN), a wireless WAN (WWAN), a metropolitan area network (MAN), a portion of the Internet, a portion of the Public Switched Telephone Network (PSTN), a cellular telephone network, or a combination of two or more of these. Network 108 may include one or more networks 108.

Links 150 may connect client system 130, wireless access point 142, social-networking system 160, and third-party system 170 to communication network 108 or to each other. This disclosure contemplates any suitable links 150. In particular embodiments, one or more links 150 include one or more wireline (such as for example Ethernet, Digital Subscriber Line (DSL), or Data Over Cable Service Interface Specification (DOCSIS)), wireless (such as for example Wi-Fi or Worldwide Interoperability for Microwave Access (WiMAX)), or optical (such as for example Synchronous Optical Network (SONET) or Synchronous Digital Hierarchy (SDH)) links. In particular embodiments, one or more links 150 each include an ad hoc network, an intranet, an extranet, a VPN, a LAN, a WLAN, a WAN, a WWAN, a MAN, a portion of the Internet, a portion of the PSTN, a cellular technology-based network, a satellite communications technology-based network, another link 150, or a combination of two or more such links 150. Links 150 need not necessarily be the same throughout network environment 101. One or more first links 150 may differ in one or more respects from one or more second links 150.

In particular embodiments, the wireless access point 142 may communicate with social-networking system 160 to determine whether a user is authorized to use wireless access point 142. The social-networking system 160 may decide whether to allow a particular user based at least upon social-networking information associated with the user and may communicate this decision to wireless access point 142.

In particular embodiments, social-networking system 160 may be a network-addressable computing system hosting an online social network. Social-networking system 160 may generate, store, receive, and transmit social-networking data, such as, for example, user-physiologic data obtained from body-associated personal communicator 104, user-profile data, concept-profile data, social-graph information, or other suitable data related to the online social network. Social-networking system 160 may be accessed by the other components of network environment 100 either directly or via network 108.

Social-networking system 160 may provide users of the online social network the ability to communicate and interact with other users wearing a body-associated personal communicator 104. In particular embodiments, users wearing a body-associated personal communicator 104 may join the online social network via social-networking system 160 and then add connections (i.e., relationships) to a number of other users of social-networking system 160 wearing a body-associated personal communicator 104 whom they want to be connected to. Herein, the term "friend" may refer to any other user of social-networking system 160 with whom a user has formed a connection, association, or relationship via social-networking system 160. For purposes of the present disclosure, friends and relationships and groupings of friends are based at least in part on user physiologic data provided to the social-networking system 160 via body-associated personal communicator 104.

In particular embodiments, social-networking system 160 may provide users with the ability to take actions on various types of items or objects, supported by social-networking system 160. As an example and not by way of limitation, the items and objects may include groups or social networks to which users of social-networking system 160 may belong, events or calendar entries in which a user might be interested, computer-based applications that a user may use, transactions that allow users to buy or sell items via the service, interactions with advertisements that a user may perform, or other suitable items or objects. A user may interact with anything that is capable of being represented in social-networking system 160 or by an external system of third-party system 170, which is separate from social-networking system 160. In particular embodiments, social-networking system 160 may include an authorization server that allows users 102 wearing a body-associated personal communicator 104 to opt in or opt out of having their actions logged by social-networking system 160 or shared with other systems (e.g., third-party systems 170), such as, for example, by setting appropriate privacy settings.

In particular embodiments, social-networking system 160 also includes user-generated content objects, which may enhance a user's interactions with social-networking system 160. User-generated content may include anything a user can add, upload, send, or "post" to social-networking system 160. As an example and not by way of limitation, body-associated personal communicator 104 communicates posts to social-networking system 160 from a client system 130. Posts may include physiologic information associated and/or ingestion information with the user as well as status updates, other textual data, location information, photos, videos, links, music or other similar data or media. Content may also be added to social-networking system 160 by a third-party through a "communication channel," such as a newsfeed or stream.

In particular embodiments, social-networking system 160 may include one or more user-profile stores for storing user profiles based on information received from body-associated personal communicator 104. A user profile may include, for example, a user name and password, identifiers of client systems used by the user, biographic information, demographic information, behavioral information, social information, physiologic information, ingestpoin information, or other types of descriptive information, such as work experience, educational history, hobbies or preferences, interests, affinities, location, or physical activities. Interest information may include interests related to one or more categories. Categories may be general or specific. As an example and not by way of limitation, if a user "likes" an article about a brand of shoes the category may be the brand, or the general category of "shoes" or "clothing." A connection store may be used for storing connection information about users. The connection information may indicate users who have similar or common work experience, group memberships, hobbies, educational history, or are in any way related or share common attributes. The connection information may also include user-defined connections between different users and content (both internal and external). A web server may be used for linking social-networking system 160 to one or more client systems 130 or one or more third-party system 170 via network 110. The web server may include a mail server or other messaging functionality for receiving and routing messages between social-networking system 160 and one or more client systems 130. An API-request server may allow a third-party system 170 to access information from social-networking system 160 by calling one or more APIs. An action logger may be used to receive communications from a web server about a user's actions on or off social-networking system 160. In conjunction with the action log, a third-party-content-object log may be maintained of user exposures to third-party-content objects. A notification controller may provide information regarding content objects to a client system 130. Information may be pushed to a client system 130 as notifications, or information may be pulled from client system 130 responsive to a request received from client system 130. Authorization servers may be used to enforce one or more privacy settings of the users of social-networking system 160. A privacy setting of a user determines how particular information associated with a user can be shared. The authorization server may allow users to opt in or opt out of having their actions logged by social-networking system 160 or shared with other systems (e.g., third-party system 170), such as, for example, by setting appropriate privacy settings. Third-party-content-object stores may be used to store content objects received from third parties, such as a third-party system 170. Location stores may be used for storing location information received from client systems 130 associated with users. Ad-pricing modules may combine social information, the current time, location information, or other suitable information to provide relevant advertisements, in the form of notifications, to a user.

In particular embodiments, a third-party system 170 may include one or more types of servers, one or more data stores, one or more interfaces, including but not limited to APIs, one or more web services, one or more content sources, one or more networks, or any other suitable components, e.g., that servers may communicate with. A third-party system 170 may be operated by a different entity from an entity operating social-networking system 160. In particular embodiments, however, social-networking system 160 and third-party systems 170 may operate in conjunction with each other to provide social-networking services to users of social-networking system 160 or third-party systems 170. In this sense, social-networking system 160 may provide a platform, or backbone, which other systems, such as third-party systems 170, may use to provide social-networking services and functionality to users across the Internet. Third-party system 170 may be accessed by the other components of network environment 101 either directly or via network 108.

In particular embodiments, a third-party system 170 may include a third-party content object provider. A third-party content object provider may include one or more sources of content objects, which may be communicated to a client system 130. As an example and not by way of limitation, content objects may include information regarding things or activities of interest to the user, such as, for example, movie show times, movie reviews, restaurant reviews, restaurant menus, product information and reviews, or other suitable information. As another example and not by way of limitation, content objects may include incentive content objects, such as coupons, discount tickets, gift certificates, or other suitable incentive objects.

Figure 3:
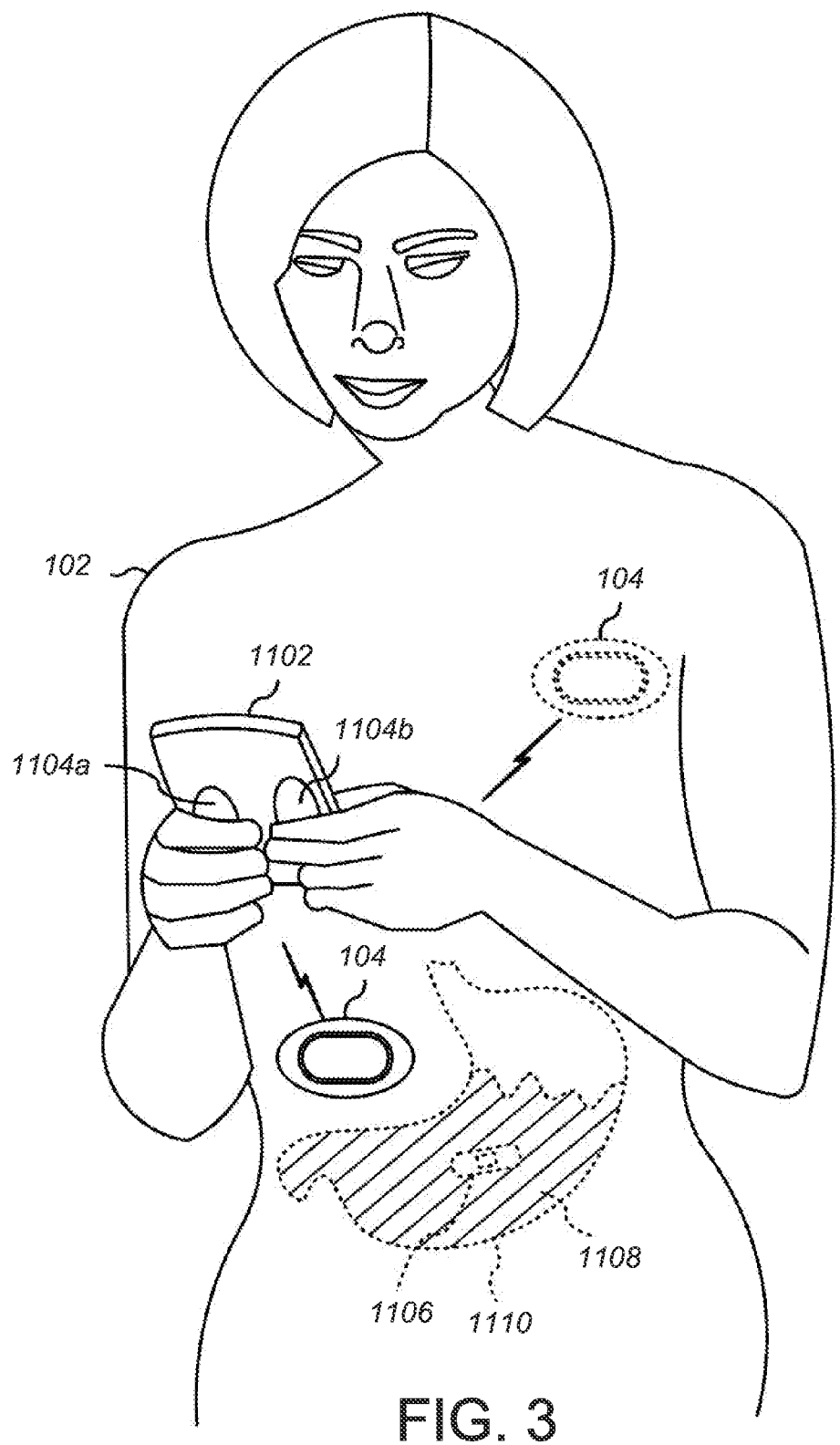
FIG. 3 illustrates a subject using a mobile device comprising electrodes for detecting personal electrical signals from the body of the subject.

FIG. 3 describes one aspect of a system employing a sensing subsystem coupled to a subject, an event indicator system, and/or a body-associated personal communicator 104 by way of at least one electrode. A subject can be person or thing that is requesting access to the social-networking system. The body-associated personal communicator 104 and the event indicator system are configured to generate a unique electrical current signal that is detectable by a detection subsystem. In addition, the detection subsystem may be configured to detect various physiologic parameters associated with a living subject.

FIG. 3 illustrates a subject 102 using a mobile device 102 comprising electrodes 1104*a*, 1104*b* for detecting personal electrical signals conducted through the body of the subject 102 where such personal electrical signals represent physiologic data associated with the subject 102. In the illustrated example, the mobile device 1102 provides access to the social-networking system 160. The mobile device 1102 comprises electrodes 1104*a*, 1104*b* integrated into the housing for detecting electrical signals coupled from the subject 102 to the electrodes 1104*a*, 1104*b*. The term personal electrical signal is used to indicate that a signal is intimately associated with the subject 102 and can be used to confirm the identity of the subject 102 for purposes of authentication and provide physiologic information and/or ingestion information to the social-networking system 160. Personal electrical signals include, without limitation, physiologic signals associated with the subject, transbody conductive signals generated by an ingestible event marker system 1106, transbody conductive signals generated by a body-associated personal communicator 104, e.g., an adhesive patch that is applied on the body of the subject 102, any object in physical contact with the subject for example watch, bracelet, necklace, ring, etc. and/or transbody conductive signals generated by an implanted body-associated device 104 that is located within the body of the subject 102. Physiologic signals include, without limitation, skin impedance, electro cardiogram signals, conductively transmitted current signal, position of wearer, temperature, heart rate, perspiration rate, humidity, altitude/pressure, global positioning system (GPS), proximity, bacteria levels, glucose level, chemical markers, blood oxygen levels, among other physiologic and physical parameters such as fingerprints of the subject 102. Transbody conductive signals include, without limitation, electrical currents that are transmitted through the body of a subject, where the body acts as the conduction medium. In one aspect, transbody conductive signals can be generated by an ingestible event marker system 1106, one example of which is described in connection with FIGS. 7 and 8. In other aspects, transbody conductive signals can be generated by electrical circuits placed in electrical contact with the surface of the skin of the subject 100 by way of a body-associated personal communicator 104. In other aspects, transbody conductive signals can be generated by electrical circuits implanted within the body of the subject 102. Additional aspects of mobile devices 1102 configured for detecting an electrical signal from an ingestible event marker system 1106, among others, are described in commonly assigned International PCT Application PCT/US/2012/047076, international publication number WO 2013/012869, which is herein incorporated by reference in its entirety.

Regardless of the source, the unique electrical signals suitable for authentication and/or social-network system 160 interfacing are coupled to the target authentication device, e.g., the mobile device 1102, through at least one of the electrodes 1104*a*, 1104*b*, which are suitable for sensing and sourcing electrical signals. In operation, the subject 102 holds the mobile device 1102, or otherwise contacts electrodes on another type of computer system, and physically contacts at least one of the electrodes 1104*a*, 1104*b*. The electrical signals are coupled from the subject 102 through at least one of the electrodes 1104*a*, 1104*b* to an authentication subsystem. The authentication subsystem can be integrated with the mobile device 1102 or may be added on.

When the ingestible event marker system 1106 is the signal source, a unique electrical current signal is generated when the ingestible event marker system 1106 contacts digestive fluids 1108 in the stomach 1110 of the subject 102. The unique electrical current signature is conducted through the body of the subject 102, is detected by at least one of the electrodes 1104*a*, 1104*b*, and is coupled to an authentication subsystem, which decodes the signal and provides a decoded signal to a processing subsystem to authenticate the subject 102.

When the body-associated personal communicator 104 is the signal source, an electrical current signal is generated by circuits in the body-associated personal communicator 104. The body-associated personal communicator 104 is electrically coupled to the body of the subject 102 by another set of electrodes. The electrical signal is conducted by the body and detected by at least one of the input electrodes 1104*a*, 1104*b* on the mobile device 1102. These and other aspects of the personal authentication techniques are discussed hereinbelow. Prior to describing such systems, however, the disclosure now turns to measurement subsystems for detecting electrical signals.

Figure 4:
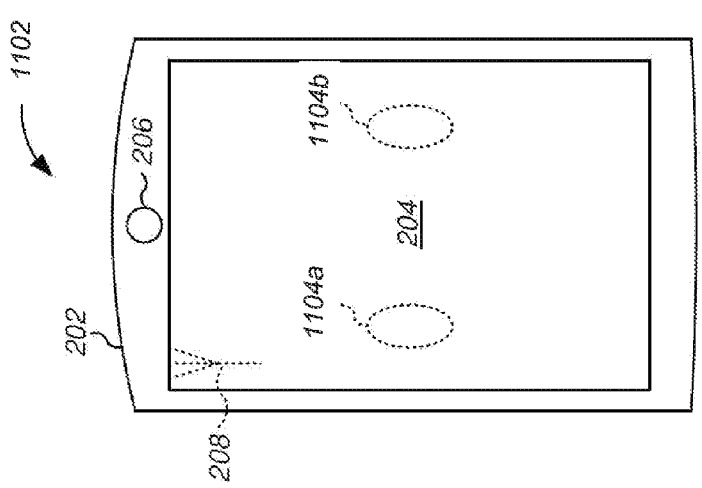
FIG. 4 illustrates one aspect of a mobile device comprising electrodes for detecting electrical signals that may be employed to authenticate the identity of the subject to enable the subject to get access to the mobile device.

FIG. 4 illustrates one aspect of a mobile device 1102 comprising electrodes 1104*a*, 1104*b* for detecting personal electrical signals suitable for authenticating the identity of the subject 102 (FIGS. 1-3) and obtaining physiologic and/or ingestion information from the subject 102. The mobile device 1102 also comprises a housing 202, a display 204, an aperture 206 for capturing digital images, and an antenna 208. The electrodes 1104*a*, 1104*b* are located on the back of the housing 202 or at any convenient location of the mobile device 1102. In one aspect, for example, the electrodes 1104*a*, 1104*b* may be located on or embedded within a skin or design cover for a mobile device 1102.

Figure 5:
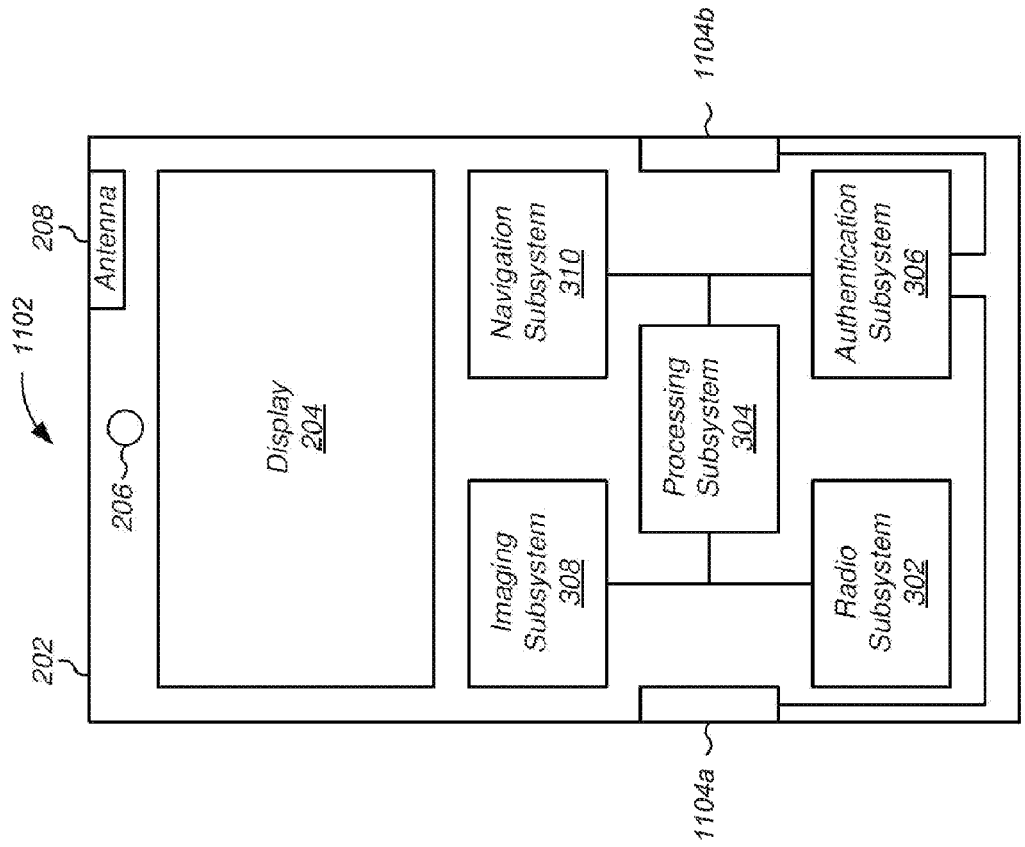
FIG. 5 is system diagram of one aspect of a mobile device configured to detect electrical signals for authenticating the identity of the subject.

FIG. 5 is a diagram of one aspect of a mobile device 1102 configured for detecting electrical signals for authenticating the identity of a subject 102 (FIGS. 1-3) and obtaining physiologic and/or ingestion information from the subject 102. The mobile device 1102 may comprise multiple elements. Although FIG. 5 shows a limited number of elements in a certain topology by way of example, it can be appreciated that additional or fewer elements in any suitable topology may be used in the mobile device 1102 as desired for a given implementation. Furthermore, any element as described herein may be implemented using hardware, software, or a combination of both, as previously described with reference to node implementations. Aspects of the mobile device 1102, however, are not limited in this context.

In various aspects, in addition to a housing 202, a display 204, an aperture 206 for capturing digital images, and an antenna 208, the mobile device 1102 comprises a radio subsystem 302 connected via a bus to a processing subsystem 304. The radio subsystem 302 may perform voice and data communications operations using wireless shared media for the mobile device 1102. The processing subsystem 304 may execute software for the mobile device 1102. A bus may comprise a USB or micro-USB bus and appropriate interfaces, as well as others.

In various aspects, an authentication and/or protection subsystem 306 is coupled to the electrodes 1104*a*, 1104*b*. The electrodes 1104*a*, 1104*b* are configured to be in physical contact with the subject 102 (FIGS. 1-3) to electrically couple the unique electrical signals to and from the authentication subsystem 306. When the subject 102 physically contacts at least one of the electrodes 1104*a*, 1104*b* the authentication subsystem 306 can receive or transmit a unique electrical current signal for authenticating the identity of the subject 102 and, once authenticated, providing access to the mobile device 1102 and/or the social-networking system 160. Also, when the authentication subsystem 306 detects physiologic signals associated with the subject 102, the authentication subsystem 306 builds a database, which over time provides an average of the physiologic signals associated with the subject 102. Authentication occurs only when the detected physiologic signals match the running average physiologic signals stored in the database.

In various aspects, the detection subsystem 306 is coupled to the processing subsystem 304. The detection subsystem 306 converts the detected electrical signals into a secret word or string of characters. A processing subsystem 304 coupled to the detection subsystem 306 uses the string of characters for user authentication to prove identity of the subject 102 (FIGS. 1-3), for access approval to gain access to the mobile device 1102, and/or for access to the social-networking system 160 (FIGS. 1-2). When the subject 102 is authenticated, the processing subsystem 304 activates the radio subsystem 304 and other functional modules of the computing device 1102, such as, for example, an imaging subsystem 308 or a navigation subsystem 310. When the subject 100 is not authenticated, the processing subsystem 304 denies access to the functional modules of the mobile device 1102 until the proper electrical signals are detected by the detection subsystem 306.

In various aspects, the display 204 may comprise any suitable display unit for displaying information appropriate for a mobile device 1102. The I/O system may comprise any suitable I/O device for entering information into the mobile device 1102. Examples for the I/O system may include an alphanumeric keyboard, a numeric keypad, a touch pad, a capacitive touch screen panel, input keys, buttons, switches, rocker switches, voice recognition device and software, and so forth. The I/O system may comprise a microphone and speaker, for example. Information also may be entered into the mobile device 1102 by way of the microphone. Such information may be digitized by a voice recognition device.

In various aspects, the radio subsystem 320 may perform voice and data communications operations using wireless shared media for the mobile device 1102. The processing subsystem 304 may execute software for the mobile device 1102. A bus may comprise a universal serial bus (USB), micro-USB bus, dataport, and appropriate interfaces, as well as others. In one aspect the radio subsystem 302 may be arranged to communicate voice information and control information over one or more assigned frequency bands of the wireless shared media.

In various aspects, the imaging subsystem 308 processes images captured through the aperture 206. A camera may be coupled (e.g., wired or wirelessly) to the processing subsystem 304 and is configured to output image data (photographic data of a person or thing, e.g., video data, digital still image data) to the processing subsystem 304 and to the display 204. In one aspect, the imaging subsystem 308 may comprise a digital camera implemented as an electronic device used to capture and store images electronically in a digital format. Additionally, in some aspects the digital camera may be capable of recording sound and/or video in addition to still images. In other implementations, the imaging subsystem may comprise a fingerprint scanner to obtain one or more fingerprints of the subject 100.

In various aspects, the imaging subsystem 308 may comprise a controller to provide control signals to components of a digital camera, including lens position component, microphone position component, and a flash control module, to provide functionality for the digital camera. In some aspects, the controller may be implemented as, for example, a host processor element of the processing subsystem 304 of the mobile device 1102. Alternatively, the imaging controller may be implemented as a separate processor from the host processor.

In various aspects, the imaging subsystem 308 may comprise memory either as an element of the processing subsystem 304 of the mobile device 1102 or as a separate element. It is worthy to note that in various aspects some portion or the entire memory may be included on the same integrated circuit as the controller. Alternatively, some portion or the entire memory may be disposed on an integrated circuit or other medium (e.g., hard disk drive) external to the integrated circuit of the controller.

In various aspects, the aperture 206 includes a lens component and a lens position component. The lens component may consist of a photographic or optical lens or arrangement of lenses made of a transparent material such as glass, plastic, acrylic or Plexiglass, for example. In one aspect, the one or more lens elements of the lens component may reproduce an image of an object and allow for zooming in or out on the object by mechanically changing the focal length of the lens elements. In various aspects, a digital zoom may be employed in the imaging subsystem 308 to zoom in or out on an image. In some aspects, the one or more lens elements may be used to focus on different portions of an image by varying the focal length of the lens elements. The desired focus can be obtained with an autofocus feature of the digital imaging subsystem 308 or by manually focusing on the desired portion of the image, for example.

In various aspects, the navigation subsystem 310 supports navigation using the mobile device 1102. In various aspects the mobile device 1102 may comprise location or position determination capabilities and may employ one or more location determination techniques including, for example, Global Positioning System (GPS) techniques, Cell Global Identity (CGI) techniques, CGI including timing advance (TA) techniques, Enhanced Forward Link Trilateration (EFLT) techniques, Time Difference of Arrival (TDOA) techniques, Angle of Arrival (AOA) techniques, Advanced Forward Link Trilateration (AFTL) techniques, Observed Time Difference of Arrival (OTDOA), Enhanced Observed Time Difference (EOTD) techniques, Assisted GPS (AGPS) techniques, hybrid techniques (e.g., GPS/CGI, AGPS/CGI, GPS/AFTL or AGPS/AFTL for CDMA networks, GPS/EOTD or AGPS/EOTD for GSM/GPRS networks, GPS/OTDOA or AGPS/OTDOA for UMTS networks), among others.

In various aspects, the mobile device 1102 may be configured to operate in one or more location determination modes including, for example, a standalone mode, a mobile station (MS) assisted mode, and/or a MS-based mode. In a standalone mode, such as a standalone GPS mode, the mobile device 1102 may be configured to determine its position without receiving wireless navigation data from the network, though it may receive certain types of position assist data, such as almanac, ephemeris, and coarse data. In a standalone mode, the mobile device 1102 may comprise a local location determination circuit such as a GPS receiver which may be integrated within the housing 202 configured to receive satellite data via the antenna 208 and to calculate a position fix. Local location determination circuit may alternatively comprise a GPS receiver in a second housing separate from the housing 202 but in the vicinity of the mobile device 102 and configured to communicate with the mobile device 1102 wirelessly (e.g., via a PAN, such as Bluetooth). When operating in an MS-assisted mode or an MS-based mode, however, the mobile device 1102 may be configured to communicate over a radio access network (e.g., UMTS radio access network) with a remote computer (e.g., a location determination entity (LDE), a location proxy server (LPS) and/or a mobile positioning center (MPC), among others).

In various aspects, the mobile device 1102 also may comprise a power management subsystem (not shown) to manage power for the mobile device 1102, including the radio subsystem 302, the processing subsystem 304, and other elements of the mobile device 1102. For example, the power management subsystem may include one or more batteries to provide direct current (DC) power, and one or more alternating current (AC) interfaces to draw power from a standard AC main power supply.

In various aspects, the radio subsystem 302 may include an antenna 208. The antenna 208 may broadcast and receive RF energy over the wireless shared media. Examples for the antenna 208 may include an internal antenna, an omni-directional antenna, a monopole antenna, a dipole antenna, an end fed antenna, a circularly polarized antenna, a microstrip antenna, a diversity antenna, a dual antenna, an antenna array, a helical antenna, and so forth. The aspects are not limited in this context.

In various aspects, the antenna 208 may be connected to a multiplexer. The multiplexer multiplexes signals from a power amplifier for delivery to the antenna 208. The multiplexer demultiplexes signals received from the antenna for delivery to an RF chipset.

In various aspects, the multiplexer may be connected to a power amplifier, where the power amplifier may be used to amplify any signals to be transmitted over the wireless shared media. The power amplifier may work in all assigned frequency bands, such as four (4) frequency bands in a quad-band system. The power amplifier also may operate in various modulation modes, such as Gaussian Minimum Shift Keying (GMSK) modulation suitable for GSM systems and 8-ary Phase Shift Keying (8-PSK) modulation suitable for EDGE systems.

In various aspects, the power amplifier may be connected to an RF chipset. The RF chipset also may be connected to the multiplexer. In one aspect, the RF chipset may comprise an RF driver and an RF transceiver. The RF chipset performs all of the modulation and direct conversion operations required for GMSK and 8-PSK signal types for quad-band E-GPRS radio. The RF chipset receives analog in-phase (I) and quadrature (Q) signals from a baseband processor, and converts the I/Q signals to an RF signal suitable for amplification by the power amplifier. Similarly, the RF chipset converts the signals received from the wireless shared media via the antenna 208 and the multiplexer to analog I/Q signals to be sent to the baseband processor. Although the RF chipset may use two chips by way of example, it may be appreciated that the RF chipset may be implemented using more or less chips and still fall within the intended scope of the aspects.

In various aspects, the RF chipset may be connected to the baseband processor, where the baseband processor may perform baseband operations for the radio subsystem 514. The baseband processor may comprise both analog and digital baseband sections. The analog baseband section includes I/Q filters, analog-to-digital converters, digital-to-analog converters, audio circuits, and other circuits. The digital baseband section may include one or more encoders, decoders, equalizers/demodulators, GMSK modulators, GPRS ciphers, transceiver controls, automatic frequency control (AFC), automatic gain control (AGC), power amplifier (PA) ramp control, and other circuits.

In various aspects, the baseband processor also may be connected to one or more memory units via a memory bus. In one aspect, for example, the baseband processor may be connected to a flash memory unit and a secure digital (SD) memory unit. The memory units may be removable or non-removable memory. In one aspect, for example, the baseband processor may use approximately 1.6 megabytes of static read-only memory (SRAM) for E-GPRS and other protocol stack needs.

In various aspects, the baseband processor also may be connected to a subscriber identity module (SIM). The baseband processor may have a SIM interface for the SIM, where the SIM may comprise a smart card that encrypts voice and data transmissions and stores data about the specific user so that the user can be identified and authenticated to the network supplying voice or data communications. The SIM also may store data such as personal phone settings specific to the user and phone numbers. The SIM can be removable or non-removable.

In various aspects, the baseband processor may further include various interfaces for communicating with a host processor of the processing subsystem 304. For example, the baseband processor may have one or more universal asynchronous receiver-transmitter (UART) interfaces, one or more control/status lines to the host processor, one or more control/data lines to the host processor, and one or more audio lines to communicate audio signals to an audio subsystem of processing subsystem 514. The aspects are not limited in this context.

In various aspects, the processing subsystem 304 may provide computing or processing operations for the mobile device 1102 and/or for the authentication subsystem 306. For example, the processing subsystem 304 may be arranged to execute various software programs for the mobile device 1102 as well as several software programs for the authentication subsystem 306. Although the processing subsystem 304 may be used to implement operations for the various aspects as software executed by a processor, it may be appreciated that the operations performed by the processing subsystem 304 also may be implemented using hardware circuits or structures, or a combination of hardware and software, as desired for a particular implementation.

In various aspects, the processing subsystem 304 may include a processor implemented using any processor or logic device, such as a complex instruction set computer (CISC) microprocessor, a reduced instruction set computing (RISC) microprocessor, a very long instruction word (VLIW) microprocessor, a processor implementing a combination of instruction sets, or other processor device. In one aspect, for example, a processor may be implemented as a general purpose processor, such as a processor made by Intel Corporation, Santa Clara, Calif. The processor also may be implemented as a dedicated processor, such as a controller, microcontroller, embedded processor, a digital signal processor (DSP), a network processor, a media processor, an input/output (I/O) processor, a media access control (MAC) processor, a radio baseband processor, a field programmable gate array (FPGA), a programmable logic device (PLD), and so forth.

In one aspect, the processing subsystem 304 may include a memory to connect to the processor. The memory may be implemented using any machine-readable or computer-readable media capable of storing data, including both volatile and non-volatile memory. For example, the memory may include ROM, RAM, DRAM, DDRAM, SDRAM, SRAM, PROM, EPROM, EEPROM, flash memory, polymer memory such as ferroelectric polymer memory, ovonic memory, phase change or ferroelectric memory, silicon-oxide-nitride-oxide-silicon (SONOS) memory, magnetic or optical cards, or any other type of media suitable for storing information. It is worthy to note that some portion or all of the memory may be included on the same integrated circuit as the processor thereby obviating the need for a memory bus. Alternatively some portion or all of the memory may be disposed on an integrated circuit or other medium, for example a hard disk drive, that is external to the integrated circuit of the processor, and the processor may access the memory via a memory bus, for example.

In various aspects, the memory may store one or more software components (e.g., application client modules). A software component may refer to one or more programs, or a portion of a program, used to implement a discrete set of operations. A collection of software components for a given device may be collectively referred to as a software architecture or application framework. A software architecture for the mobile device 102 is described in more detail below.

A software architecture suitable for use with the mobile device 102 may include a user interface (UI) module, an interface module, a data source or backend services module (data source), and a third party API module. An optional LBS module may comprise a user based permission module, a parser module (e.g., National Maritime Electronic Association or NMEA), a location information source module, and a position information source module. In some aspects, some software components may be omitted and others added. Further, operations for some programs may be separated into additional software components, or consolidated into fewer software components, as desired for a given implementation. The mobile device 102 software architecture may comprise several elements, components or modules, collectively referred to herein as a "module." A module may be implemented as a circuit, an integrated circuit, an application specific integrated circuit (ASIC), an integrated circuit array, a chipset comprising an integrated circuit or an integrated circuit array, a logic circuit, a memory, an element of an integrated circuit array or a chipset, a stacked integrated circuit array, a processor, a digital signal processor, a programmable logic device, code, firmware, software, and any combination thereof.

Having described the mobile device 1102 as one example of computer system, it will be appreciated that any of the following computer systems, without limitation, computer networks, desktop computers, laptop computers, notebook computers, tablet computers, tablet computers, mobile phones, personal digital assistants, appliances, positioning systems, media devices, automatic teller machines (ATM), kiosks, public modes of transportation (bus, train, subway, airplane, boat, rental car, . . . ), building entrances, stadiums, turnstiles, medical systems that dispense medication in any form could be equipped with at least one electrode and a detection subsystem to authenticate the user as the owner of the computer system for security purposes. For the sake of conciseness and clarity, not all of these computer systems will be discussed here.

Figure 6:
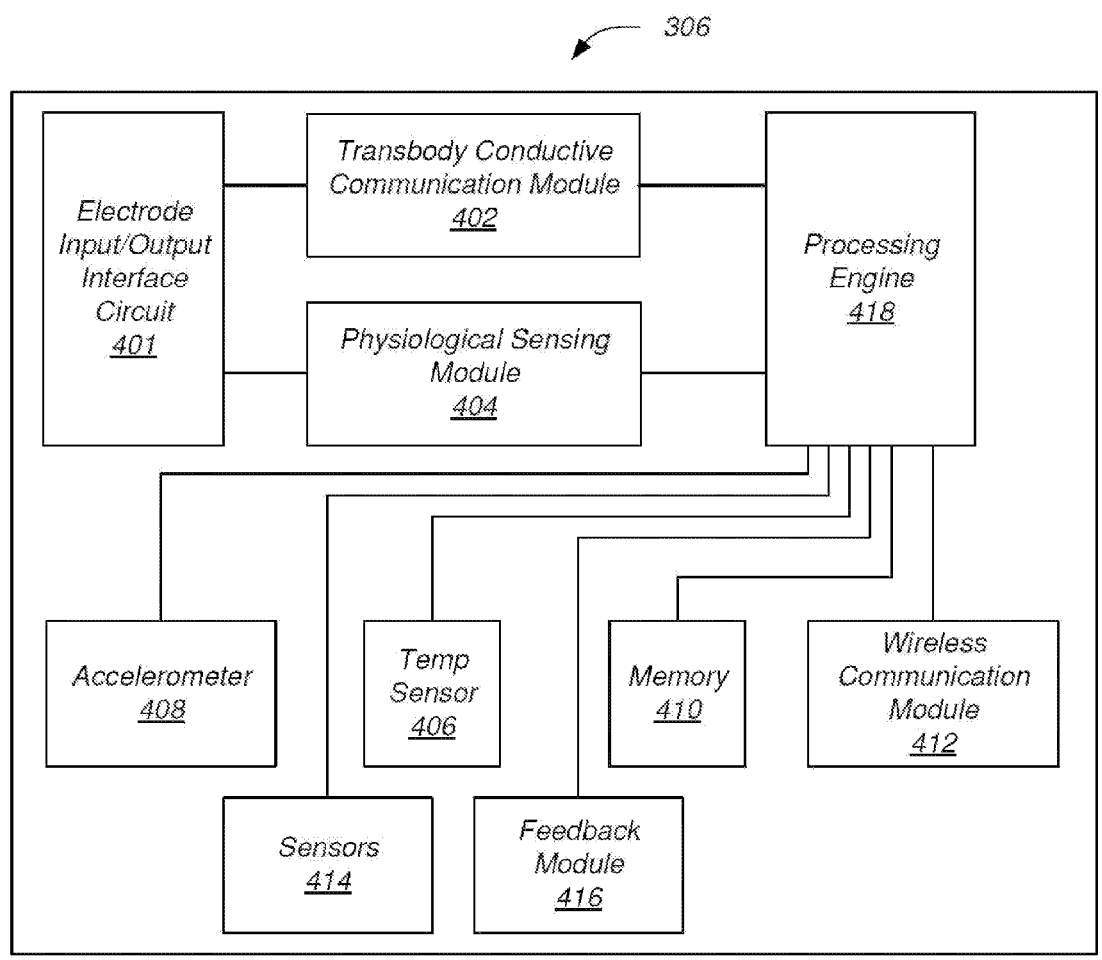
FIG. 6 is a block functional diagram of one aspect of an authentication subsystem for detecting and/or generating a transconductance signal to confirm the identity of a person.

Turning now to FIG. 6, which is a block functional diagram of one aspect of a subsystem 306 for detecting and/or generating personal electrical signals to authenticate the user and prove the identity of the subject 102 (FIGS. 1-3). The subsystem 306 comprises an electrode input/output interface circuit 401 to receive/transmit electrical signals from/to the electrodes 1104a, 1104b (FIGS. 3-5). The subsystem 306 can be configured to operate in receive mode, broadcast mode, or combinations thereof. In receive mode, the input/output interface circuit 401 receives electrical signals from the electrodes 1104a, 1104b. In broadcast mode, the input/output interface circuit 401 transmits electrical signals to the electrodes 1104a, 1104b.

A transbody conductive communication module 402 and a physiologic sensing module 404 are electrically coupled to the electrode input/output interface circuit 401. In one aspect, the transbody conductive communication module 402 is implemented as a first, e.g., high, frequency (HF) signal chain and the physiologic sensing module 404 is implemented as a second, e.g., low, frequency (LF) signal chain. Also shown are CMOS temperature sensing module 406 (for detecting ambient temperature) and a 3-axis accelerometer 408. The subsystem 306 also comprises a processing engine 418 (for example, a microcontroller and digital signal processor), a non-volatile memory 410 (for data storage), and a wireless communication module 412 to receive data from and/or transmit data to another device, for example in a data download/upload action, respectively. In various aspects, the communication module 412 may comprise one or more transmitters/receivers ("transceiver") modules. As used herein, the term "transceiver" may be used in a very general sense to include a transmitter, a receiver, or a combination of both, without limitation. In one aspect, the transbody conductive communication module 402 is configured to communicate with an ingestible event marker system 1106 (FIG. 3). In receive mode, the transbody conductive communication module 402 is configured to receive a transconduction current signal from the subject 102 (FIGS. 1-3) via at least one of the electrodes 1104a, 1104b (FIGS. 3-5). In broadcast mode, the transbody conductive communication module 402 is configured to transmit a transconduction current signal to the subject 100 via at least one of the electrodes 1104a, 1104b. In one aspect, the transbody conductive communication module 402 is configured as a skin or design cover for a mobile device.

The sensors 414 typically contact the subject 102 (FIGS. 1-3), e.g., are removably attachable to the torso. In various aspects, the sensors 414 may be removably or permanently attached to the authentication subsystem 306. For example, the sensors 414 may be removably connected to another device by snapping metal studs. The sensors 414 may comprise, for example, various devices capable of sensing or receiving the physiologic data. The types of sensors 414 include, for example, electrodes such as biocompatible electrodes. The sensors 414 may be configured, for example, as a pressure sensor, a motion sensor, an accelerometer, an electromyography (EMG) sensor, an event marker system, a biopotential sensor, an electrocardiogram sensor, a temperature sensor, a tactile event marker sensor, and an impedance sensor.

The feedback module 416 may be implemented with software, hardware, circuitry, various devices, and combinations thereof. The function of the feedback module 416 is to provide communication with the subject 102 (FIGS. 1-3) in a discreet, tactful, circumspect manner as described above. In various aspects the feedback module 416 may be implemented to communicate with the subject 102 using techniques that employ visual, audio, vibratory/tactile, olfactory, and taste.

With reference to FIG. 7, there is shown one aspect of an ingestible device event indicator system (e.g., IEM) with dissimilar metals positioned on opposite ends as system 2030. The system 2030 can be used in association with any pharmaceutical product, as mentioned above, to determine when a patient takes the pharmaceutical product. As indicated above, the scope of the present invention is not limited by the environment and the product that is used with the system 2030. For example, the system 2030 may be placed within a capsule and the capsule is placed within the conducting liquid. The capsule would then dissolve over a period of time and release the system 2030 into the conducting liquid. Thus, in one aspect, the capsule would contain the system 2030 and no product. Such a capsule may then be used in any environment where a conducting liquid is present and with any product. For example, the capsule may be dropped into a container filled with jet fuel, salt water, tomato sauce, motor oil, or any similar product. Additionally, the capsule containing the system 2030 may be ingested at the same time that any pharmaceutical product is ingested in order to record the occurrence of the event, such as when the product was taken.

In the specific example of the system 2030 combined with the pharmaceutical product, as the product or pill is ingested, the system 2030 is activated. The system 2030 controls conductance to produce a unique current signature that is detected, thereby signifying that the pharmaceutical product has been taken. The system 2030 includes a framework 2032. The framework 2032 is a chassis for the system 2030 and multiple components are attached to, deposited upon, or secured to the framework 2032. In this aspect of the system 2030, a digestible material 2034 is physically associated with the framework 2032. The material 2034 may be chemically deposited on, evaporated onto, secured to, or built-up on the framework all of which may be referred to herein as "deposit" with respect to the framework 2032. The material 2034 is deposited on one side of the framework 2032. The materials of interest that can be used as material 2034 include, but are not limited to: Cu or CuI. The material 2034 is deposited by physical vapor deposition, electrodeposition, or plasma deposition, among other protocols. The material 2034 may be from about 0.05 to about 500 .mu.m thick, such as from about 5 to about 100 .mu.m thick. The shape is controlled by shadow mask deposition, or photolithography and etching. Additionally, even though only one region is shown for depositing the material, each system 2030 may contain two or more electrically unique regions where the material 2034 may be deposited, as desired.

At a different side, which is the opposite side as shown in FIG. 7, another digestible material 2036 is deposited, such that materials 2034 and 2036 are dissimilar. Although not shown, the different side selected may be the side next to the side selected for the material 2034. The scope of the present invention is not limited by the side selected and the term "different side" can mean any of the multiple sides that are different from the first selected side. Furthermore, even though the shape of the system is shown as a square, the shape maybe any geometrically suitable shape. Material 2034 and 2036 are selected such that they produce a voltage potential difference when the system 2030 is in contact with conducting liquid, such as body fluids. The materials of interest for material 2036 include, but are not limited to: Mg, Zn, or other electronegative metals. As indicated above with respect to the material 2034, the material 2036 may be chemically deposited on, evaporated onto, secured to, or built-up on the framework. Also, an adhesion layer may be necessary to help the material 2036 (as well as material 2034 when needed) to adhere to the framework 2032. Typical adhesion layers for the material 2036 are Ti, TiW, Cr or similar material. Anode material and the adhesion layer may be deposited by physical vapor deposition, electrodeposition or plasma deposition. The material 2036 may be from about 0.05 to about 500 µm thick, such as from about 5 to about 100 µm thick. However, the scope of the present invention is not limited by the thickness of any of the materials nor by the type of process used to deposit or secure the materials to the framework 2032.

Thus, when the system 2030 is in contact with the conducting liquid, a current path, an example is shown in FIG. 7, is formed through the conducting liquid between material 2034 and 2036. A control device 2038 is secured to the framework 2032 and electrically coupled to the materials 2034 and 2036. The control device 2038 includes electronic circuitry, for example control logic that is capable of controlling and altering the conductance between the materials 2034 and 2036.

The voltage potential created between the materials 2034 and 2036 provides the power for operating the system as well as produces the current flow through the conducting fluid and the system. In one aspect, the system operates in direct current mode. In an alternative aspect, the system controls the direction of the current so that the direction of current is reversed in a cyclic manner, similar to alternating current. As the system reaches the conducting fluid or the electrolyte, where the fluid or electrolyte component is provided by a physiologic fluid, e.g., stomach acid, the path for current flow between the materials 2034 and 2036 is completed external to the system 2030; the current path through the system 2030 is controlled by the control device 2038. Completion of the current path allows for the current to flow and in turn a receiver, not shown, can detect the presence of the current and recognize that the system 2030 has been activate and the desired event is occurring or has occurred.

In one aspect, the two materials 2034 and 2036 are similar in function to the two electrodes needed for a direct current power source, such as a battery. The conducting liquid acts as the electrolyte needed to complete the power source. The completed power source described is defined by the physical chemical reaction between the materials 2034 and 2036 of the system 2030 and the surrounding fluids of the body. The completed power source may be viewed as a power source that exploits reverse electrolysis in an ionic or a conductive solution such as gastric fluid, blood, or other bodily fluids and some tissues. Additionally, the environment may be something other than a body and the liquid may be any conducting liquid. For example, the conducting fluid may be salt water or a metallic based paint.

In certain aspects, these two materials are shielded from the surrounding environment by an additional layer of material. Accordingly, when the shield is dissolved and the two dissimilar materials are exposed to the target site, a voltage potential is generated.

Referring again to FIG. 7, the materials 2034 and 2036 provide the voltage potential to activate the control device 2038. Once the control device 2038 is activated or powered up, the control device 2038 can alter conductance between the materials 2034 and 2036 in a unique manner. By altering the conductance between materials 2034 and 2036, the control device 2038 is capable of controlling the magnitude of the current through the conducting liquid that surrounds the system 2030. This produces a unique current signature that can be detected and measured by a receiver (not shown), which can be positioned internal or external to the body. In addition to controlling the magnitude of the current path between the materials, non-conducting materials, membrane, or "skirt" are used to increase the "length" of the current path and, hence, act to boost the conductance path, as disclosed in the U.S. patent application Ser. No. 12/238,345 entitled, "In-Body Device with Virtual Dipole Signal Amplification" filed Sep. 25, 2008, the entire content of which is incorporated herein by reference. Alternatively, throughout the disclosure herein, the terms "non-conducting material", "membrane", and "skirt" are interchangeably with the term "current path extender" without impacting the scope or the present aspects and the claims herein. The skirt, shown in portion at 2035 and 2037, respectively, may be associated with, e.g., secured to, the framework 2032. Various shapes and configurations for the skirt are contemplated as within the scope of the present invention. For example, the system 2030 may be surrounded entirely or partially by the skirt and the skirt maybe positioned along a central axis of the system 2030 or off-center relative to a central axis. Thus, the scope of the present invention as claimed herein is not limited by the shape or size of the skirt. Furthermore, in other aspects, the materials 2034 and 2036 may be separated by one skirt that is positioned in any defined region between the materials 2034 and 2036.

Referring now to FIG. 8, in another aspect of an ingestible device is shown in more detail as system 2040. The system 2040 includes a framework 2042. The framework 2042 is similar to the framework 2032 of FIG. 7. In this aspect of the system 2040, a digestible or dissolvable material 2044 is deposited on a portion of one side of the framework 2042. At a different portion of the same side of the framework 2042, another digestible material 2046 is deposited, such that materials 2044 and 2046 are dissimilar. More specifically, material 2044 and 2046 are selected such that they form a voltage potential difference when in contact with a conducting liquid, such as body fluids. Thus, when the system 2040 is in contact with and/or partially in contact with the conducting liquid, then a current path, an example is shown in FIG. 9, is formed through the conducting liquid between material 2044 and 2046. A control device 2048 is secured to the framework 2042 and electrically coupled to the materials 2044 and 2046. The control device 2048 includes electronic circuitry that is capable of controlling part of the conductance path between the materials 2044 and 2046. The materials 2044 and 2046 are separated by a non-conducting skirt 2049. Various examples of the skirt 2049 are disclosed in U.S. Provisional Application No. 61/173,511 filed on Apr. 28, 2009 and entitled "HIGHLY RELIABLE INGESTIBLE EVENT MARKERS AND METHODS OF USING SAME" and U.S. Provisional Application No. 61/173,564 filed on Apr. 28, 2009 and entitled "INGESTIBLE EVENT MARKERS HAVING SIGNAL AMPLIFIERS THAT COMPRISE AN ACTIVE AGENT"; as well as U.S. application Ser. No. 12/238,345 filed Sep. 25, 2008 and published as 2009-0082645, entitled "IN-BODY DEVICE WITH VIRTUAL DIPOLE SIGNAL AMPLIFICATION"; the entire disclosure of each is incorporated herein by reference.

Once the control device 2048 is activated or powered up, the control device 2048 can alter conductance between the materials 2044 and 2046. Thus, the control device 2048 is capable of controlling the magnitude of the current through the conducting liquid that surrounds the system 2040. As indicated above with respect to system 2030, a unique current signature that is associated with the system 2040 can be detected by a receiver (not shown) to mark the activation of the system 2040. In order to increase the "length" of the current path the size of the skirt 2049 is altered. The longer the current path, the easier it may be for the receiver to detect the current.

Referring now to FIG. 9, the system 2030 of FIG. 7 is shown in an activated state and in contact with conducting liquid. The system 2030 is grounded through ground contact 2052. The system 2030 also includes a sensor module 2074, which is described in greater detail with respect to FIG. 9 ion or current paths 2050 form between material 2034 to material 2036 through the conducting fluid in contact with the system 2030. The voltage potential created between the material 2034 and 2036 is created through chemical reactions between materials 2034/2036 and the conducting fluid.

FIG. 9A shows an exploded view of the surface of the material 2034. The surface of the material 2034 is not planar, but rather an irregular surface 2054 as shown. The irregular surface 2054 increases the surface area of the material and, hence, the area that comes in contact with the conducting fluid.

In one aspect, at the surface of the material 2034, there is chemical reaction between the material 2034 and the surrounding conducting fluid such that mass is released into the conducting fluid. The term "mass" as used herein refers to protons and neutrons that form a substance. One example includes the instant where the material is CuCl and when in contact with the conducting fluid, CuCl becomes Cu (solid) and Cl.sup.—in solution. The flow of ions into the conduction fluid is depicted by the ion paths 2050. In a similar manner, there is a chemical reaction between the material 2036 and the surrounding conducting fluid and ions are captured by the material 2036. The release of ions at the material 2034 and capture of ion by the material 2036 is collectively referred to as the ionic exchange. The rate of ionic exchange and, hence the ionic emission rate or flow, is controlled by the control device 2038. The control device 2038 can increase or decrease the rate of ion flow by altering the conductance, which alters the impedance, between the materials 2034 and 2036. Through controlling the ion exchange, the system 2030 can encode information in the ionic exchange process. Thus, the system 2030 uses ionic emission to encode information in the ionic exchange.

The control device 2038 can vary the duration of a fixed ionic exchange rate or current flow magnitude while keeping the rate or magnitude near constant, similar to when the frequency is modulated and the amplitude is constant. Also, the control device 2038 can vary the level of the ionic exchange rate or the magnitude of the current flow while keeping the duration near constant. Thus, using various combinations of changes in duration and altering the rate or magnitude, the control device 2038 encodes information in the current flow or the ionic exchange. For example, the control device 2038 may use, but is not limited to any of the following techniques namely, Binary Phase-Shift Keying (PSK), Frequency modulation, Amplitude modulation, on-off keying, and PSK with on-off keying.

As indicated above, the various aspects disclosed herein, such as systems 2030 and 2040 of FIGS. 7 and 8, respectively, include electronic components as part of the control device 2038 or the control device 2048. Components that may be present include but are not limited to: logic and/or memory elements, an integrated circuit, an inductor, a resistor, and sensors for measuring various parameters. Each component may be secured to the framework and/or to another component. The components on the surface of the support may be laid out in any convenient configuration. Where two or more components are present on the surface of the solid support, interconnects may be provided.

As indicated above, the system, such as system 2030 and 2040, control the conductance between the dissimilar materials and, hence, the rate of ionic exchange or the current flow. Through altering the conductance in a specific manner the system is capable of encoding information in the ionic exchange and the current signature. The ionic exchange or the current signature is used to uniquely identify the specific system. Additionally, the systems 2030 and 2040 are capable of producing various different unique exchanges or signatures and, thus, provide additional information. For example, a second current signature based on a second conductance alteration pattern may be used to provide additional information, which information may be related to the physical environment. To further illustrate, a first current signature may be a very low current state that maintains an oscillator on the chip and a second current signature may be a current state at least a factor of ten higher than the current state associated with the first current signature.

Figure 9B:
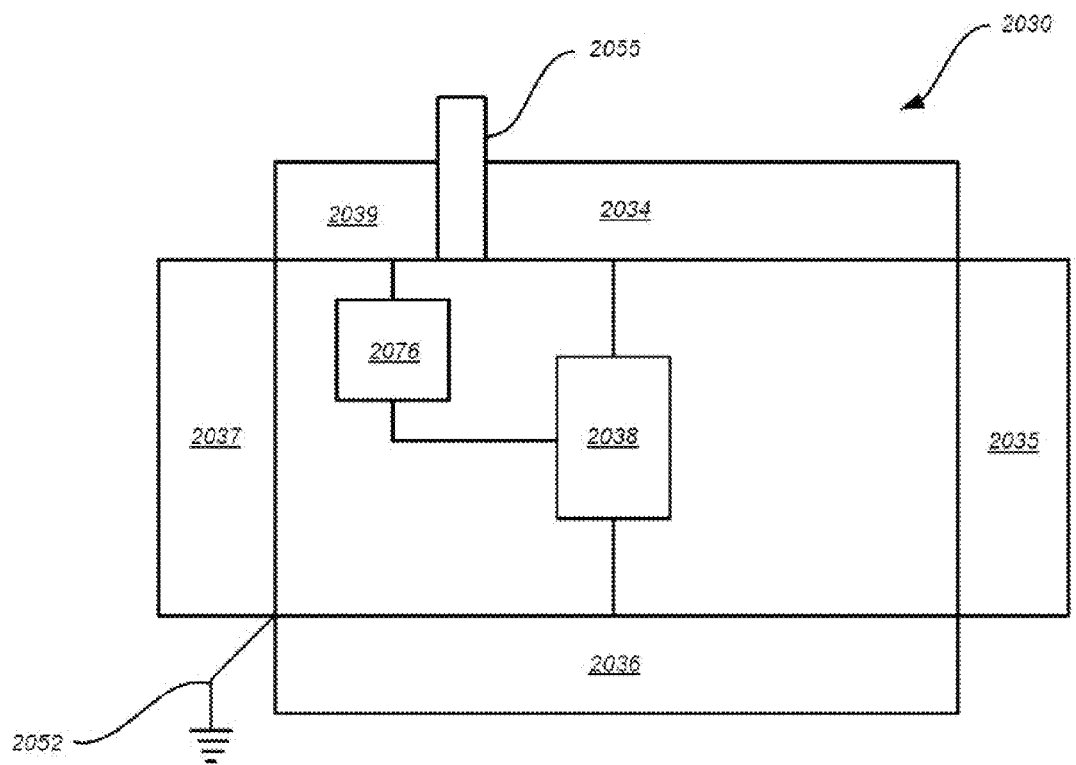
FIG. 9B shows the event indicator system of FIG. 11 with a pH sensor unit.
Figure 10:
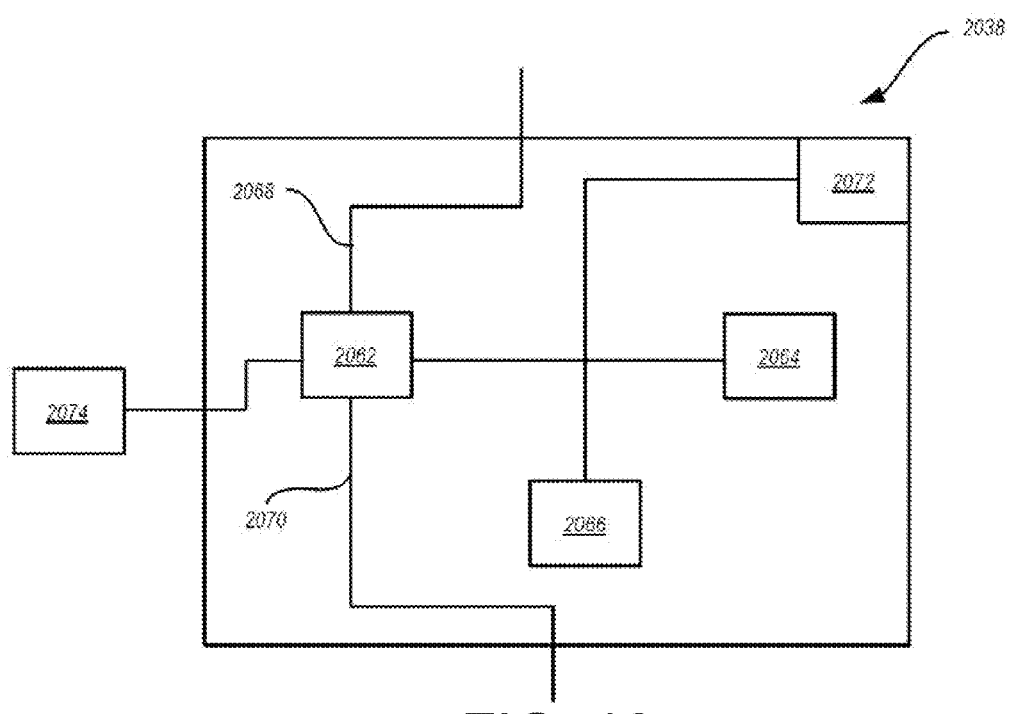
FIG. 10 is a block diagram illustration of one aspect of the control device used in the system of FIGS. 7 and 8.

Referring now to FIG. 10, a block diagram representation of the control device 2038 is shown. The device 2030 includes a control module 2062, a counter or clock 2064, and a memory 2066. Additionally, the device 2038 is shown to include a sensor module 2072 as well as the sensor module 2074, which was referenced in FIG. 9. The control module 2062 has an input 2068 electrically coupled to the material 2034 and an output 2070 electrically coupled to the material 2036. The control module 2062, the clock 2064, the memory 2066, and the sensor modules 2072/2074 also have power inputs (some not shown). The power for each of these components is supplied by the voltage potential produced by the chemical reaction between materials 2034 and 2036 and the conducting fluid, when the system 2030 is in contact with the conducting fluid. The control module 2062 controls the conductance through logic that alters the overall impedance of the system 2030. The control module 2062 is electrically coupled to the clock 2064. The clock 2064 provides a clock cycle to the control module 2062. Based upon the programmed characteristics of the control module 2062, when a set number of clock cycles have passed, the control module 2062 alters the conductance characteristics between materials 2034 and 2036. This cycle is repeated and thereby the control device 2038 produces a unique current signature characteristic. The control module 2062 is also electrically coupled to the memory 2066. Both the clock 2064 and the memory 2066 are powered by the voltage potential created between the materials 2034 and 2036.

The control module 2062 is also electrically coupled to and in communication with the sensor modules 2072 and 2074. In the aspect shown, the sensor module 2072 is part of the control device 2038 and the sensor module 2074 is a separate component. In alternative aspects, either one of the sensor modules 2072 and 2074 can be used without the other and the scope of the present invention is not limited by the structural or functional location of the sensor modules 2072 or 2074. Additionally, any component of the system 2030 may be functionally or structurally moved, combined, or repositioned without limiting the scope of the present invention as claimed. Thus, it is possible to have one single structure, for example a processor, which is designed to perform the functions of all of the following modules: the control module 2062, the clock 2064, the memory 2066, and the sensor module 2072 or 2074. On the other hand, it is also within the scope of the present invention to have each of these functional components located in independent structures that are linked electrically and able to communicate.

Referring again to FIG. 10, the sensor modules 2072 or 2074 can include any of the following sensors: temperature, pressure, pH level, and conductivity. In one aspect, the sensor modules 2072 or 2074 gather information from the environment and communicate the analog information to the control module 2062. The control module then converts the analog information to digital information and the digital information is encoded in the current flow or the rate of the transfer of mass that produces the ionic flow. In another aspect, the sensor modules 2072 or 2074 gather information from the environment and convert the analog information to digital information and then communicate the digital information to control module 2062. In the aspect shown in FIG. 9, the sensor modules 2074 is shown as being electrically coupled to the material 2034 and 2036 as well as the control device 2038. In another aspect, as shown in FIG. 10, the sensor module 2074 is electrically coupled to the control device 2038 at connection 2078. The connection 2078 acts as both a source for power supply to the sensor module 2074 and a communication channel between the sensor module 2074 and the control device 2038.

Referring now to FIG. 9B, the system 2030 includes a pH sensor module 2076 connected to a material 2039, which is selected in accordance with the specific type of sensing function being performed. The pH sensor module 2076 is also connected to the control device 2038. The material 2039 is electrically isolated from the material 2034 by a non-conductive barrier 2055. In one aspect, the material 2039 is platinum. In operation, the pH sensor module 2076 uses the voltage potential difference between the materials 2034/2036. The pH sensor module 2076 measures the voltage potential difference between the material 2034 and the material 2039 and records that value for later comparison. The pH sensor module 2076 also measures the voltage potential difference between the material 2039 and the material 2036 and records that value for later comparison. The pH sensor module 2076 calculates the pH level of the surrounding environment using the voltage potential values. The pH sensor module 2076 provides that information to the control device 2038. The control device 2038 varies the rate of the transfer of mass that produces the ionic transfer and the current flow to encode the information relevant to the pH level in the ionic transfer, which can be detected by a receiver (not shown). Thus, the system 2030 can determine and provide the information related to the pH level to a source external to the environment.

As indicated above, the control device 2038 can be programmed in advance to output a pre-defined current signature. In another aspect, the system can include a receiver system that can receive programming information when the system is activated. In another aspect, not shown, the switch 2064 and the memory 2066 can be combined into one device.

In addition to the above components, the system 2030 may also include one or other electronic components. Electrical components of interest include, but are not limited to: additional logic and/or memory elements, e.g., in the form of an integrated circuit; a power regulation device, e.g., battery, fuel cell or capacitor; a sensor, a stimulator, etc.; a signal transmission element, e.g., in the form of an antenna, electrode, coil, etc.; a passive element, e.g., an inductor, resistor, etc.

Figure 11:
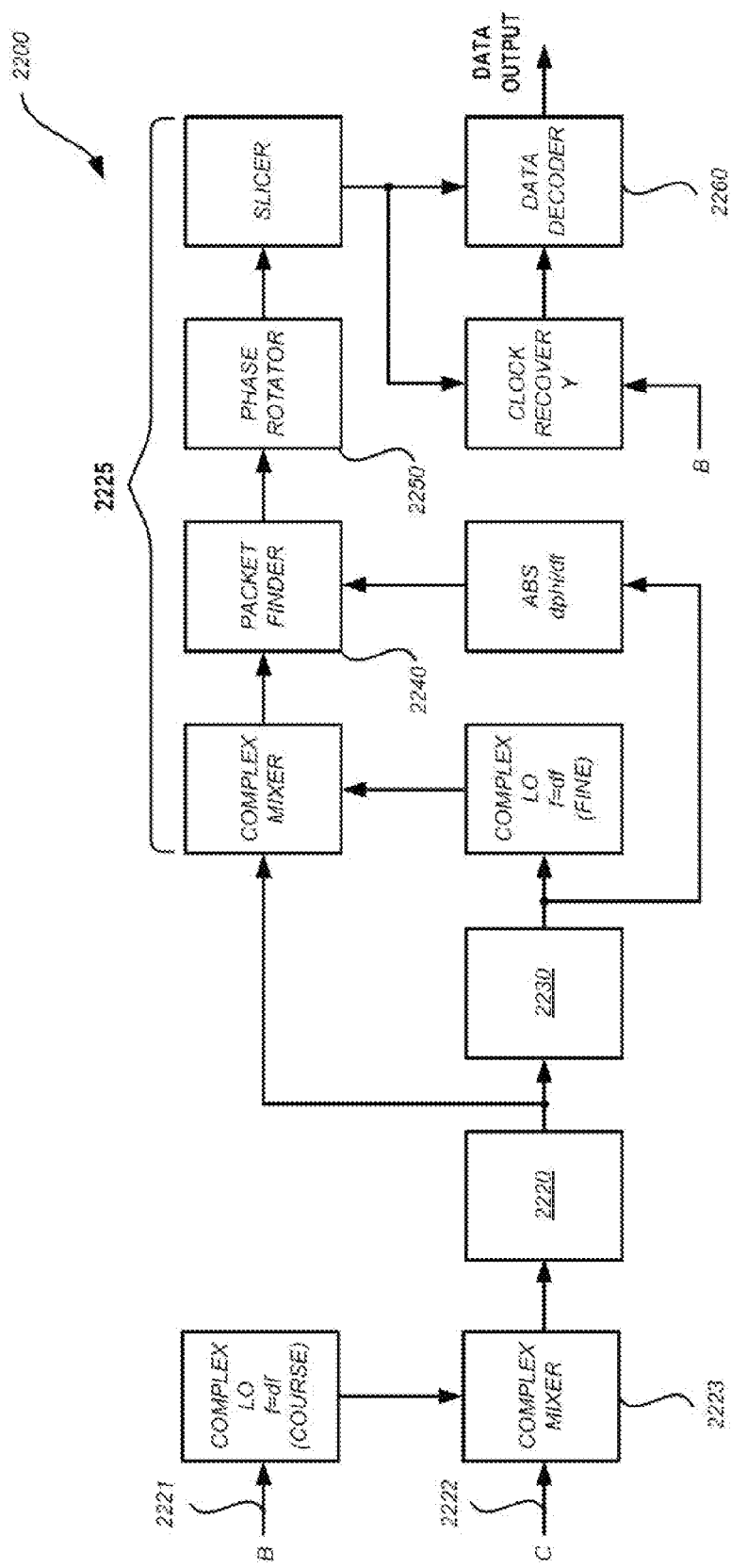
FIG. 11 is a functional block diagram of a demodulation circuit that performs coherent demodulation that may be present in a receiver, according to one aspect.

FIG. 11 provides a functional block diagram 2200 of how a receiver (e.g., body-associated personal communicator 104) may implement a coherent demodulation protocol, according to one aspect of the invention. It should be noted that only a portion of the receiver is shown in FIG. 11. FIG. 11 illustrates the process of mixing the signal down to baseband once the carrier frequency (and carrier signal mixed down to carrier offset) is determined. A carrier signal 2221 is mixed with a second carrier signal 2222 at mixer 2223. A narrow low-pass filter 2220 is applied of appropriate bandwidth to reduce the effect of out-of-bound noise. Demodulation occurs at functional blocks 2225 in accordance with the coherent demodulation scheme of the present invention. The unwrapped phase 2230 of the complex signal is determined. An optional third mixer stage, in which the phase evolution is used to estimate the frequency differential between the calculated and real carrier frequency can be applied. The structure of the packet is then leveraged to determine the beginning of the coding region of the BPSK signal at block 2240. Mainly, the presence of the sync header, which appears as an FM porch in the amplitude signal of the complex demodulated signal is used to determine the starting bounds of the packet. Once the starting point of the packet is determined the signal is rotated at block 2250 on the IQ plane and standard bit identification and eventually decoded at block 2260.

In addition to demodulation, the transbody communication module may include a forward error correction module, which module provides additional gain to combat interference from other unwanted signals and noise. Forward error correction functional modules of interest include those described in PCT Application Serial No. PCT/US2007/024225; the disclosure of which is herein incorporated by reference. In some instances, the forward error correction module may employ any convenient protocol, such as Reed-Solomon, Golay, Hamming, BCH, and Turbo protocols to identify and correct (within bounds) decoding errors.

Receivers of the invention, such as the body-associated personal communicator 104, may further employ a beacon functionality module. In various aspects, the beacon switching module may employ one or more of the following: a beacon wakeup module, a beacon signal module, a wave/frequency module, a multiple frequency module, and a modulated signal module.

The beacon switching module may be associated with beacon communications, e.g., a beacon communication channel, a beacon protocol, etc. For the purpose of the present disclosure, beacons are typically signals sent either as part of a message or to augment a message (sometimes referred to herein as "beacon signals"). The beacons may have well-defined characteristics, such as frequency. Beacons may be detected readily in noisy environments and may be used for a trigger to a sniff circuit, such as described below. In one aspect, the beacon switching module may comprise the beacon wakeup module, having wakeup functionality. Wakeup functionality generally comprises the functionality to operate in high power modes only during specific times, e.g., short periods for specific purposes, to receive a signal, etc. An important consideration on a receiver portion of a system is that it be of low power. This feature may be advantageous in an implanted receiver, to provide for both small size and to preserve a long-functioning electrical supply from a battery. The beacon switching module enables these advantages by having the receiver operate in a high power mode for very limited periods of time. Short duty cycles of this kind can provide optimal system size and energy draw features.

In practice, the receiver may "wake up" periodically, and at low energy consumption, to perform a "sniff function" via, for example, a sniff circuit. For the purpose of the present application, the term "sniff function" generally refers to a short, low-power function to determine if a transmitter is present. If a transmitter signal is detected by the sniff function, the device may transition to a higher power communication decode mode. If a transmitter signal is not present, the receiver may return, e.g., immediately return, to sleep mode. In this manner, energy is conserved during relatively long periods when a transmitter signal is not present, while high-power capabilities remain available for efficient decode mode operations during the relatively few periods when a transmit signal is present. Several modes, and combination thereof, may be available for operating the sniff circuit. By matching the needs of a particular system to the sniff circuit configuration, an optimized system may be achieved.

Figure 12:
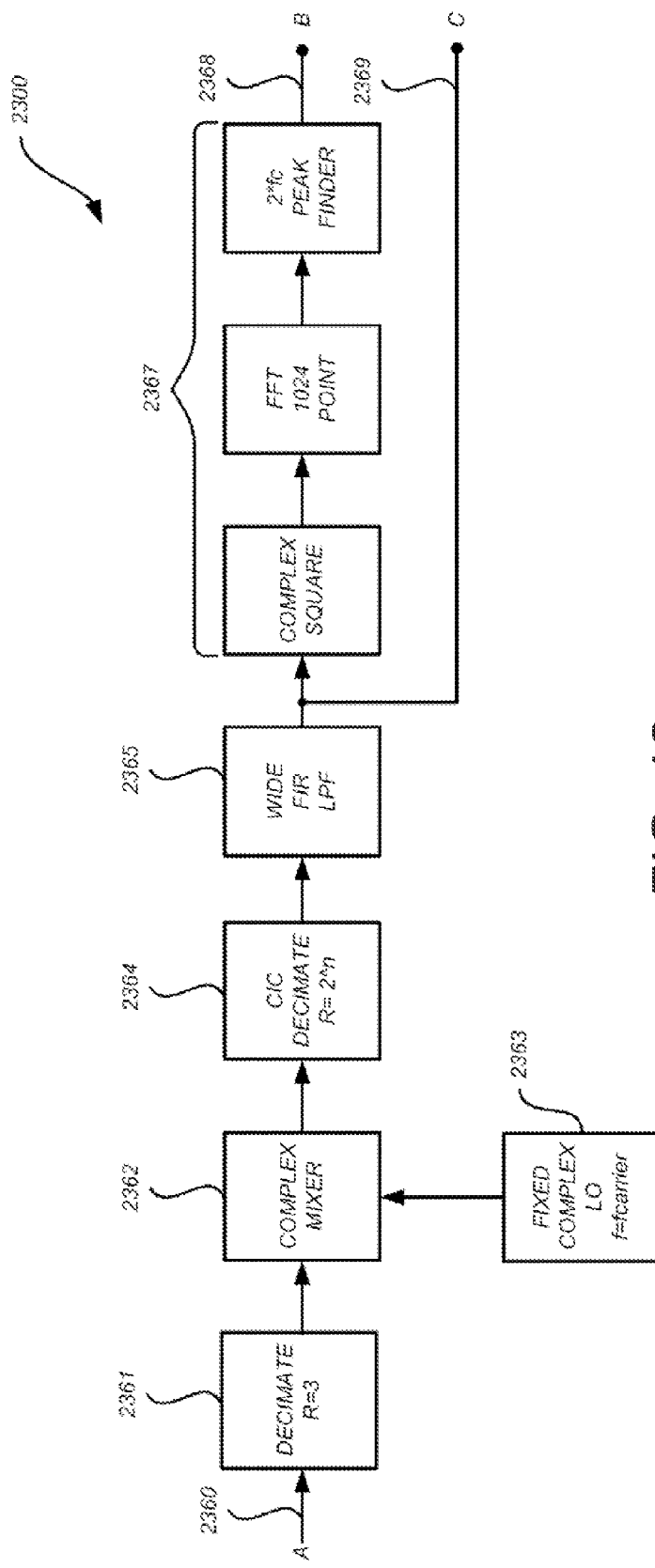
FIG. 12 illustrates a functional block diagram for a beacon module within a receiver, according to one aspect.

Another view of a beacon module is provided in the functional block diagram shown in FIG. 12. The scheme outlined in FIG. 12 outlines one technique for identifying a valid beacon. The incoming signal 2360 represents the signals received by electrodes, bandpass filtered (such as from 10 KHz to 34 KHz) by a high frequency signaling chain (which encompasses the carrier frequency), and converted from analog to digital. The signal 2360 is then decimated at block 2361 and mixed at the nominal drive frequency (such as, 12.5 KHz, 20 KHz, etc.) at mixer 2362. The resulting signal is decimated at block 2364 and low-pass filtered (such as 5 KHz BW) at block 2365 to produce the carrier signal mixed down to carrier offset—signal 2369. Signal 2369 is further processed by blocks 2367 (fast Fourier transform and then detection of two strongest peaks) to provide the true carrier frequency signal 2368. This protocol allows for accurate determination of the carrier frequency of the transmitted beacon.

Figure 13:
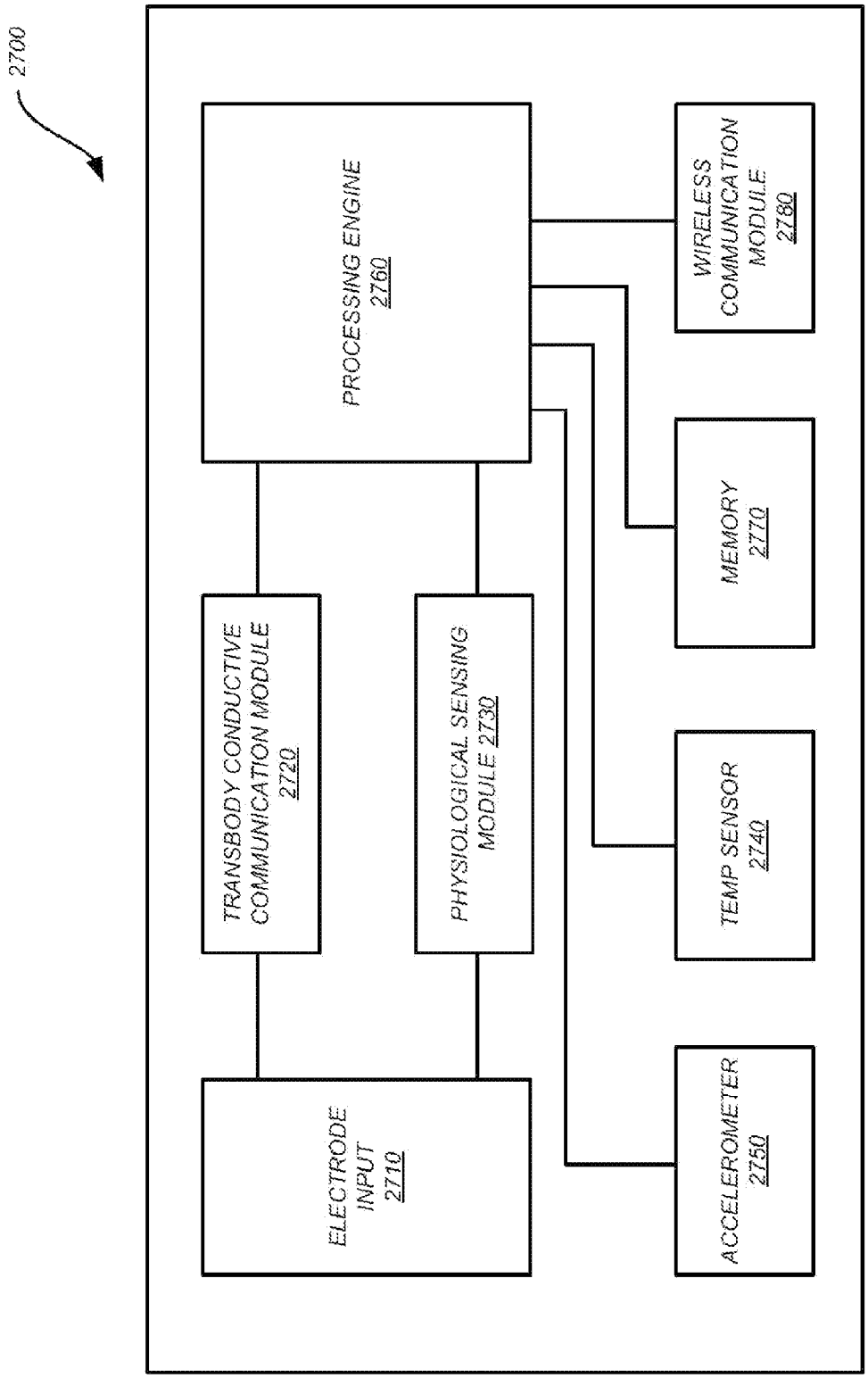
FIG. 13 is a block diagram of the different functional modules that may be present in a receiver, according to one aspect.

FIG. 13 provides a block functional diagram of an integrated circuit component of a signal receiver (e.g., body-associated personal communicator 104) according to an aspect of the invention. In FIG. 13, receiver 2700 includes electrode input 2710. Electrically coupled to the electrode input 2710 are transbody conductive communication module 2720 and physiologic sensing module 2730. In one aspect, transbody conductive communication module 2720 is implemented as a high frequency (HF) signal chain and physiologic sensing module 2730 is implemented as a low frequency (LF) signal chain. Also shown are CMOS temperature sensing module 2740 (for detecting ambient temperature) and a 3-axis accelerometer 2750. Receiver 2700 also includes a processing engine 2760 (for example, a microcontroller and digital signal processor), non-volatile memory 2770 (for data storage) and wireless communication module 2780 (for data transmission to another device, for example in a data upload action).

Figure 14:
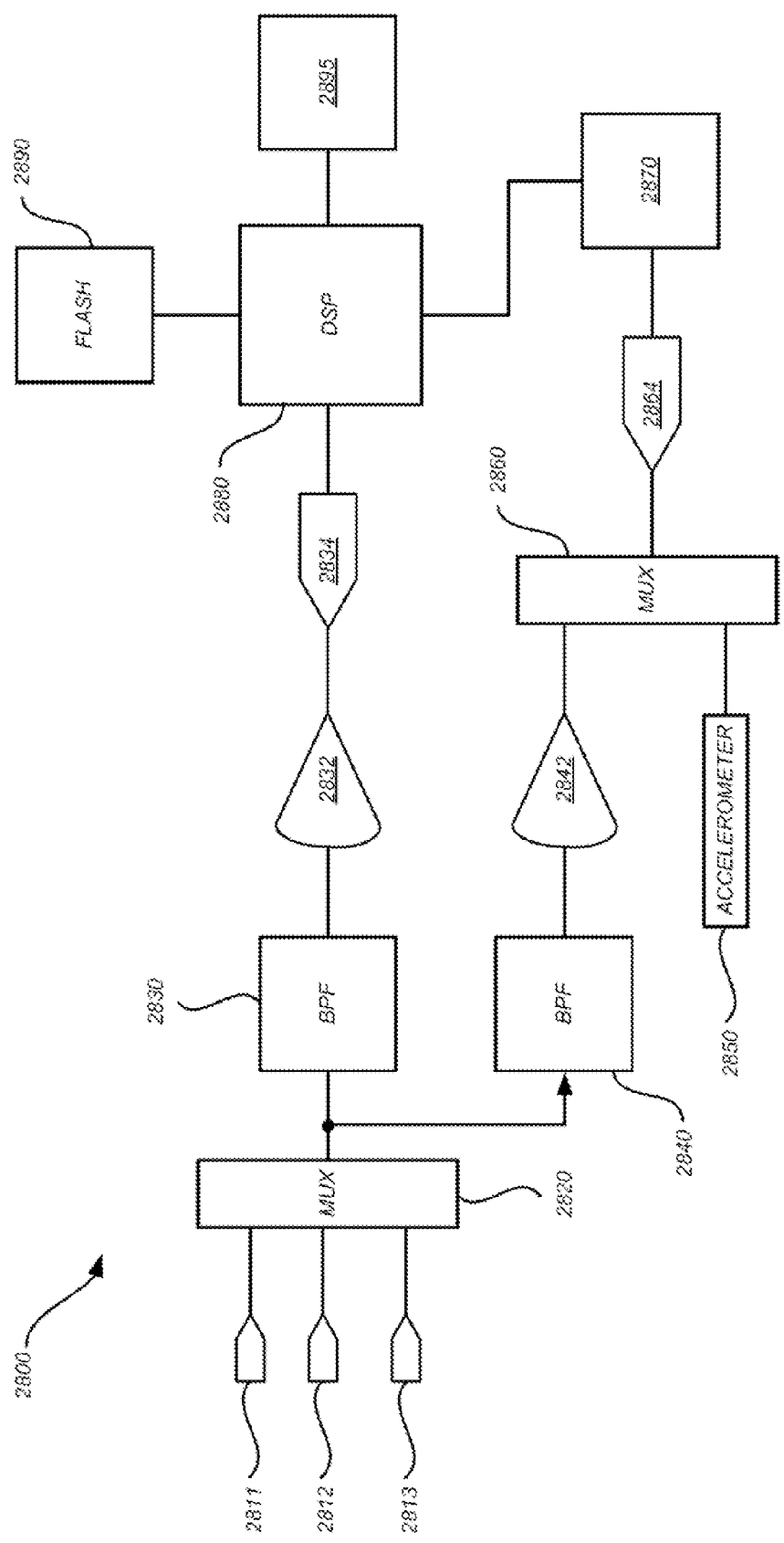
FIG. 14 is a block diagram of a receiver, according to one aspect.

FIG. 14 provides a more detailed block diagram of a circuit configured to implement the block functional diagram of the receiver (e.g., body-associated personal communicator 104) depicted in FIG. 14, according to one aspect of the invention. In FIG. 14, receiver 800 (e.g., body-associated personal communicator 104) includes electrodes e1, e2 and e3 (2811, 2812 and 2813) which, for example, receive the conductively transmitted signals by an IEM and/or sense physiologic parameters or biomarkers of interest. The signals received by the electrodes 2811, 2812, and 2813 are multiplexed by multiplexer 820 which is electrically coupled to the electrodes.

Multiplexer 2820 is electrically coupled to both high band pass filter 2830 and low band pass filter 2840. The high and low frequency signal chains provide for programmable gain to cover the desired level or range. In this specific aspect, high band pass filter 2830 passes frequencies in the 10 KHz to 34 KHz band while filtering out noise from out-of-band frequencies. This high frequency band may vary, and may include, for example, a range of 3 KHz to 300 KHz. The passing frequencies are then amplified by amplifier 2832 before being converted into a digital signal by converter 2834 for input into high power processor 2880 (shown as a DSP) which is electrically coupled to the high frequency signal chain.

Low band pass filter 2840 is shown passing lower frequencies in the range of 0.5 Hz to 150 Hz while filtering out out-of-band frequencies. The frequency band may vary, and may include, for example, frequencies less than 300 Hz, such as less than 200 Hz, including less than 150 Hz. The passing frequency signals are amplified by amplifier 842. Also shown is accelerometer 850 electrically coupled to second multiplexer 2860. Multiplexer 2860 multiplexes the signals from the accelerometer with the amplified signals from amplifier 2842. The multiplexed signals are then converted to digital signals by converter 864 which is also electrically coupled to low power processor 2870.

In one aspect, a digital accelerometer (such as one manufactured by Analog Devices), may be implemented in place of accelerometer 2850. Various advantages may be achieved by using a digital accelerometer. For example, because the signals the digital accelerometer would produce signals already in digital format, the digital accelerometer could bypass converter 2864 and electrically couple to the low power microcontroller 2870—in which case multiplexer 2860 would no longer be required. Also, the digital signal may be configured to turn itself on when detecting motion, further conserving power. In addition, continuous step counting may be implemented. The digital accelerometer may include a FIFO buffer to help control the flow of data sent to the low power processor 2870. For instance, data may be buffered in the FIFO until full, at which time the processor may be triggered to turn awaken from an idle state and receive the data.

Low power processor 2870 may be, for example, an MSP430 microcontroller from Texas Instruments. Low power processor 2870 of receiver 2800 maintains the idle state, which as stated earlier, requires minimal current draw—e.g., 10 µA or less, or 1 µA or less.

High power processor 2880 may be, for example, a VC5509 digital signal process from Texas Instruments. The high power processor 2880 performs the signal processing actions during the active state. These actions, as stated earlier, require larger amounts of current than the idle state—e.g., currents of 30 µA or more, such as 50 µA or more—and may include, for example, actions such as scanning for conductively transmitted signals, processing conductively transmitted signals when received, obtaining and/or processing physiologic data, etc.

The receiver (e.g., body-associated personal communicator 104) may include a hardware accelerator module to process data signals. The hardware accelerator module may be implemented instead of, for example, a DSP. Being a more specialized computation unit, it performs aspects of the signal processing algorithm with fewer transistors (less cost and power) compared to the more general purpose DSP. The blocks of hardware may be used to "accelerate" the performance of important specific function(s). Some architectures for hardware accelerators may be "programmable" via microcode or VLIW assembly. In the course of use, their functions may be accessed by calls to function libraries.

The hardware accelerator (HWA) module comprises an HWA input block to receive an input signal that is to be processed and instructions for processing the input signal; and, an HWA processing block to process the input signal according to the received instructions and to generate a resulting output signal. The resulting output signal may be transmitted as needed by an HWA output block.

Also shown in FIG. 14 is flash memory 2890 electrically coupled to high power processor 2880. In one aspect, flash memory 2890 may be electrically coupled to low power processor 2870, which may provide for better power efficiency.

Wireless communication element 2895 is shown electrically coupled to high power processor 2880 and may include, for example, a BLUETOOTH™ wireless communication transceiver. In one aspect, wireless communication element 2895 is electrically coupled to high power processor 2880. In another aspect, wireless communication element 2895 is electrically coupled to high power processor 2880 and low power processor 2870. Furthermore, wireless communication element 2895 may be implemented to have its own power supply so that it may be turned on and off independently from other components of the receiver—e.g., by a microprocessor.

FIG. 15 provides a view of a block diagram of hardware in a receiver (e.g., body-associated personal communicator 104) according to an aspect of the invention related to the high frequency signal chain. In FIG. 15, receiver 2900 includes receiver probes (for example in the form of electrodes 2911, 2912 and 2913) electrically coupled to multiplexer 2920. Also shown are high pass filter 2930 and low pass filter 2940 to provide for a band pass filter which eliminates any out-of-band frequencies. In the aspect shown, a band pass of 10 KHz to 34 KHz is provided to pass carrier signals falling within the frequency band. Example carrier frequencies may include, but are not limited to, 12.5 KHz and 20 KHz. One or more carriers may be present. In addition, receiver 2900 includes analog to digital converter 2950—for example, sampling at 500 KHz. The digital signal can thereafter be processed by the DSP. Shown in this aspect is DMA to DSP unit 960 which sends the digital signal to dedicated memory for the DSP. The direct memory access provides the benefit of allowing the rest of the DSP to remain in a low power mode.

Example Configurations for Various States

As stated earlier, for each receiver state, the high power functional block may be cycled between active and inactive states accordingly. Also, for each receiver state, various receiver elements (such as circuit blocks, power domains within processor, etc.) of a receiver may be configured to independently cycle from on and off by the power supply module. Therefore, the receiver may have different configurations for each state to achieve power efficiency.

In certain aspects, the receivers are part of a body-associated system or network of devices, such as sensors, signal receivers, and optionally other devices, which may be internal and/or external, which provide a variety of different types of information that is ultimately collected and processed by a processor, such as an external processor, which then can provide contextual data about a living subject, such as a patient, as output. For example, the receiver may be a member of an in-body network of devices which can provide an output that includes data about IEM ingestion, one or more physiologic sensed parameters, implantable device operation, etc., to an external collector of the data. The external collector, e.g., in the form of a health care network server, etc., of the data then combines this receiver provided data with additional relevant data about the patient, e.g., weight, weather, medical record data, etc., and may process this disparate data to provide highly specific and contextual patient specific data.

Systems of the invention include, in certain aspects, a signal receiver aspect of a receiver and one or more IEMs. IEMs of interest include those described in PCT application serial no. PCT/US2006/016370 published as WO/2006/116718; PCT application serial no. PCT/US2007/082563 published as WO/2008/052136; PCT application serial no. PCT/US2007/024225 published as WO/2008/063626; PCT application serial no. PCT/US2007/022257 published as WO/2008/066617; PCT application serial no. PCT/US2008/052845 published as WO/2008/095183; PCT application serial no. PCT/US2008/053999 published as WO/2008/101107; PCT application serial no. PCT/US2008/056296 published as WO/2008/112577; PCT application serial no. PCT/US2008/056299 published as WO/2008/112578; and PCT application serial no. PCT/US2008/077753 published as WO 2009/042812; the disclosures of which applications are herein incorporated by reference.

In certain aspects the systems include an external device which is distinct from the receiver (which may be implanted or topically applied in certain aspects), where this external device provides a number of functionalities. Such an external device can include the capacity to provide feedback and appropriate clinical regulation to the patient. Such a device can take any of a number of forms. For example, the device can be configured to sit on the bed next to the patient, e.g., a bedside monitor. Other formats include, but are not limited to, PDAs, smart phones, home computers, etc.

An example of a system of the invention is shown in FIG. 16. In FIG. 16, system 1500 includes a pharmaceutical composition 1510 that comprises an IEM. Also present in system 1500 is signal receiver 1520, such as the signal receiver illustrated in FIG. 11. Signal receiver 1520 is configured to detect a signal emitted from the identifier of the IEM 1510. Signal receiver 1520 also includes physiologic sensing capability, such as ECG and movement sensing capability. Signal receiver 1520 is configured to transmit data to a patient's an external device or PDA 1530 (such as a smart phone or other wireless communication enabled device), which in turn transmits the data to a server 1540. Server 1540 may be configured as desired, e.g., to provide for patient directed permissions. For example, server 1540 may be configured to allow a family caregiver 1550 to participate in the patient's therapeutic regimen, e.g., via an interface (such as a web interface) that allows the family caregiver 1550 to monitor alerts and trends generated by the server 1540, and provide support back to the patient, as indicated by arrow 1560. The server 1540 may also be configured to provide responses directly to the patient, e.g., in the form of patient alerts, patient incentives, etc., as indicated by arrow 1565 which are relayed to the patient via PDA 1530. Server 1540 may also interact with a health care professional (e.g., RN, physician) 1555, which can use data processing algorithms to obtain measures of patient health and compliance, e.g., wellness index summaries, alerts, cross-patient benchmarks, etc., and provide informed clinical communication and support back to the patient, as indicated by arrow 1580. In other embodiments, server 1540 is a social-networking system.

Having described social-network environment associated in which information can be provided to a social-networking system 160 by a body-associated personal communicator 104, the description now turns to various social media applications of social-networking system 160 employing physiologic information received from body-associated personal communicator 104. Various aspects include by way of example and not limitation, timelines, awards/incentives, analytics, grouping, mentoring, mood, emotion, access, identification, among others. Physical networks may be captured by the social-networking system 160 via passive searching of information from body-associated personal communicators 104.

FIG. 17 is a flow diagram 1700 of a method associated with a social-networking system. In accordance with the method, a social-networking system 160 (FIG. 2) receives 1702 physiologic information from a body-associated personal communicator 104 (FIGS. 1-3). Once the physiologic information is received 1702 by the social-networking system 160, the social-networking system 160 may perform any one of the following. In one aspect, the social-networking system 160 may generate 1704 a private or public timeline for a user of the social-networking system 160 based on the physiologic information. In another aspect, the social-networking system 160 may provide 1706 rewards, awards, or incentives to users of the social-networking system 160 based on the physiologic information. In another aspect, the social-networking system 160 may provide 1708 an analytical framework to users of the social-networking system based on the physiologic information. In another aspect, the social-networking system 160 may group 1710 a plurality of users of the social-networking system 160 based on the physiologic information. In another aspect, the social-networking system 160 identifies 1712 a mentor or leader from a plurality of users of the social-networking system 160 based on the physiologic information. In another aspect, the social-networking system 160 determines 1714 a mood or emotional state of a user of the social-networking system 160 based on the physiologic information. In another aspect, the social-networking system 160 receives 1716 identification information of a user of the social-networking system 160 based on the physiologic information. In a further aspect, the social-networking system 160 provides 1718 access to a user of the social-networking system 160 based on the identification information. These and other aspects of the present social-networking system base don physiologic information are described hereinbelow.

Timelines

Accordingly, in one aspect, the social-networking system 160 provides a social media platform to enable users to create and maintain public and private timelines. In one aspect, a public timeline located in a public profile page of the user may be pulled into a private timeline located in a private profile page of the user and private information may be added either manually or automatically to the private timeline. Present solutions and postings on social-networking systems include only a user's "best" information. Postings on the social-networking system 160 in accordance with the present disclosure enables a user to add private information, wellness information, physiologic information, and ingestion information and to mix and match public information with private information on the private timeline. Timeline changes may be based on food, activities, algorithms, private or shared information with the public, among others. A private timeline is a timeline that is only visible to the user where the user can record and review his/her own timeline. A user can add personal details and things that are important to the user such as health information provided to the social-networking system 160 by the body-associated personal communicator 104. The personal public or private timelines may provide personal insights into the user. In one example, the private timeline may include a health and wellness timeline. Private health timelines can be based on events, mood, food, activity, behavior adherence, among others.

Rewards/Awards/Incentives

In another aspect, the social-networking system 160 provides a social media platform to issue rewards/awards/incentives to enable users to rank and compete with other. Ranking and competition using personal or team metrics and goals may be employed to encourage manual or automatic data entry. Team metrics can be used to allocate points to track rankings and competition. Team versus team data displays which team has the best individual aggregated statistics. Ranking and/or competition may be based on the amount of information provided to the social-networking system 160, whether the information is provided automatically, through the body-associated personal communicator 104, or manually. Awards may be given based on product specific criteria. Rewards such as "likes" are powerful motivators for users. A large motivating number of "likes" for a goal can translate into positive incentives for the user. In other aspects, caregivers may be incentivized for intervention and/or outreach. In summary, ranking and competition encourages users to enter information.

Other rewards may be based on IQ, which quantifies our logical Intelligence, EQ, which quantifies emotional intelligence, and/or BQ, which quantifies body intelligence. It will be appreciated that BQ information can be provided to the social-networking system 160 by the body-associated personal communicator 104, either manually or automatically. BQ information also may be supplemented with medication ingestion information provided by an ingestible event marker (IEM).

Likes for a goal set by a user can trigger other incentives, offers of help, people with similar goals, etc. In other aspects, community feedback is a reward for taking medications, which is confirmed by the body-associated personal communicator 104. In another aspect, the body-associated personal communicator 104 may provide physiologic information to the social-networking system 160 in the form of body temperature measurements, which can be displayed as a heat map to indicate exercise levels of several users within the group. This may be relative to the group and key to award (motivation to group awards-personal tie in). Other rewards may be based on a user's resume rather than job title. Rewards may be based on group health behavior. For example, Cleveland clinic cheek swab or the idea that one cannot be employed if one is a smoker. Other rewards may be base don posting images of healthy foods. Still other rewards may be based on the insurance marketplace where the insurance benefit rewards for positive behavior. Physiologic and ingestion information from the body-associated personal communicator 104 may be utilized to prove that the user is taking care of him/herself to obtain benefit reduction. In other insurance related aspects, the physiologic and ingestion information provided to the social-networking system 160 by the body-associated personal communicator 104 may be utilized in a health insurance auction where the insurance company is bidding for healthy users.

Analytics

In another aspect, the social-networking system 160 provides social media platform that employs analytics to measure performance and enable the social-networking system 160 to rank users and/or activities. Use metrics may include a Nielson-type ratings methodology where advertisement revenue is based on viewership. Other techniques include look-a-like analysis where health outcomes are based on clustering and predictive analytics.

Grouping

In another aspect, the social-networking system 160 provides a social media platform for grouping users. In various aspects, groupings may be made automatically based on association metrics, data, or sensor related data provided by the body-associated personal communicator 104. In other aspects, groupings may be based on social support networks to provide users with support based on unexpected events in nature, health, fitness, and community building activities. Examples include social support networks for users with similar issues or interests including, for example, groupings based on recovering alcoholics, community building based on interaction, physical proximity, interest factors such as hiking, timing of hike, running, difficulty of run/hiking trail/elevation, decisions, caregiver communities. Automatic grouping may be based on location or forming communities, for example, a social network operator may suggest that a user be a team leader or mentor for a particular group (catalyst). Other grouping features may include understanding support networks and advanced use of search to find people. Support networks can be provided to achieve a goal (e.g., Yoga expert that travels too much) and for group alignment. A virtual walk to support a particular cause or charity may be conducted in real time on the social-networking system 160 utilizing physiologic information and/or ingestion information received from the body-associated personal communicator 104. A support network may include collective live display of physiologic information such the number of steps taken either for a cause or to make a statement or ingestion information.

Groupings allow users to find people that are engaged in similar activities with similar abilities such as, for example, people who like to run in a certain area, at the same pace, and at the same time can be automatically grouped based on physiologic information input into the social-networking system 160. Rapid exchange of information in a specific region to people who are in the same region may be provided. Users may suggest running paths to other users with the same fitness level among other criteria such as, time of run, running, difficulty of run, elevation, etc. Grouping also may be based on collective live display of steps, ingestions, other physiologic information to make a statement, support a cause, etc. In other grouping or forming of communities, information can be shared within the group anonymously, for example, during a crisis information may be aggregated by location and an event happening in that area without revealing user identities. In other aspects, grouping may be based on geographic location (e.g., as determined by GPS), age, interests, time overlays, among others. Relationships may be via sensors located on the body-associated personal communicator 104 rather than pictures. Accordingly, groups may be formed automatically based on sensor detected behavior/sickness. In another aspect, groups may be formed based on relationships between mentors and mentees. In one aspect the social-networking system 160 is configured to automatically determine mentors and/or mentees based on sensor detected behavior.

As a service model the IEM may be used as an identifier that is unique to the user and can be used for authentication and also social interaction. Other groupings may be based on blood donations or voting.

In addition to ingestion information, or in place thereof, groupings also may be based on goal setting and rewards for achieving certain goals.

Mentoring

In another aspect, the social-networking system 160 provides a social media platform for determining and recommending users for leadership and/or mentoring roles based on any of the social media categories described herein. For example, social-networking system 160 may recommend a user as a leader or mentor for a specific group based on the user's profile. The user may then choose whether or not to accept such recommendation. The social-networking system 160 also may associate a user fro remote to coaching roles for groups based on associations with sports and physical activity. Remote coaching association may be peer based, people who have previously accomplished goals you have set, many-to-one or one-to-one.

Mood/Emotion

In another aspect, the social-networking system 160 provides a social media platform for determining the mood and emotional state of a user based on information gathered from the body-associated personal communicator 104 or other techniques. Additionally, the social-networking system 160 provides a social media platform for intervention. A display of the user's mood or emotional state may be visualized during a crisis or specific event such as, for example, sleep, stress level, etc. Mood or emotion based on visualizations may be analogous to visualizations of weather forecast. The pulse of a community or city and its present mood may be based on outcomes of local events such as local team winning or losing other events unique to that location. Mood or emotion may be based on sociability on the social-networking system 160, which may prompt interventions by applications executing on the body-associated personal communicator 104. Physiologic and emotional responses can be monitored during certain events such as debates, voting, etc. Other outcomes include detection of sickness, condition, depression, pregnancy, sociability, or death.

In another aspect, the social-networking system 160 provides a social media platform for adding emotional states into written communications such as text messaging and email postings. Text messages and email are notorious for being easily misread as having the wrong agenda or with implied emotion, intent. Physiologic measurements from the body-associated personal communicator 104 communicated to the social-networking system 160 may be leveraged to create an emotional language that becomes imparted into messaging. The content of the text or email message combined with the measured emotional state of the user may be utilized by an algorithm to differentiate and classify differences in emotional states between fear, anger, excitement, etc. This added emotional language may be useful in other application and places, some more wholesome than others and provides a new dimension to all forms of written communication. The continuous information collected by body-associated personal communicator 104 could be used to validate measurements with timing of measurements, previous but recent measurements, time of message, if the message is a response to another message, when the message was viewed, etc.

Identification/Access

In another aspect, the social-networking system 160 provides a social media platform for identifying a user and enabling the user to access to the social-networking system 160 based on the identity. In one aspect, identification by and access to the social-networking system 160 may be based on uniquely identifiable ingestion information as communicated by an IEM to the body-associated personal communicator 104 or physiologic parameters associated with the user. The ingestion information may be utilized to unlock and provide access to the social-networking system 160 or to provide access to certain features of the social-networking system 160 or to obtain rewards.

In another aspect, the body-associated personal communicator 104 or client device 130 includes a fingerprinting module to capture the user's fingerprint(s). The fingerprint information can be utilized as an advanced form of user identification to access the social-networking system 160. In another aspect, the IEM ingestion information, which includes a unique identification number, may be utilized as another form of user identification to access the social-networking system 160. In yet another aspect, the physiologic information measured by the body-associated personal communicator 104 may be utilized as another form of user identification to access the social-networking system 160. In yet another aspect, device identification associated with the body-associated personal communicator 104 may be utilized as another form of user identification to access the social-networking system 160. In other aspects any combination of fingerprint information, IEM ingestion information, physiologic information, and/or device identification information may be utilized as a form of identification to enable access to the social-networking system 160 or features thereof. These various forms of identification may provide access to the private timeline and generally provide for better overall authentication.

Other Examples

In other aspects, the physiologic and ingestion information from the body-associated personal communicator 104 may be employed in other social media websites, such as, for example dating sites. People inherently like to receive feedback on their dates. Physiologic information is great feedback in such instances not only for the user from user's date. Social dating websites may be configured to provide feedback based on physiologic information received from a body-associated personal communicator 104. This would provide more comprehensive feedback information on dating and may help people understand their behaviors in not so ideal social situations and learn how to handle them. In one aspect, the body-associated personal communicator 104 would also provide fitness levels of the user as another parameter in the user profile. This information could be utilized to confirm whether a date is "athletically toned" as indicated in the user profile. The physiologic information provided by the body-associated personal communicator 104 would lend more credibility to user profiles. This aspect may extend to other social media websites reporting on events. People post pictures, write words, now post body data related to events. A user post may include "went out with someone last night here is the photo, here is how my body behaved."

In another aspect, the body-associated personal communicator 104 may be a component of hardware-augmented Internet businesses, otherwise referred to as the Internet-of-things. The body-associated personal communicator 104 and the social-networking system 160 provide a health and wellness social network. In one aspect, an FDA-approved physiologic sensing platform, including the body-associated personal communicator 104, capable of tracking exercise, recovery, and integrating data from other sources is combined with a worldwide social media network platform such as the social-networking system 160. The social-networking system 160 communities would be utilized to support health and wellness goals and healthy behaviors of all kinds. Information generated by the body-associated personal communicator 104 may be employed to login into the social-networking system 160 and tailor the personalized interaction model on the social-networking system 160 user profile. The social-networking system 160 may be configured to distribute alerts and data via its mobile platform, creating a new engagement mechanism for athletes and other social-networking system 160 users intent on achieving health and wellness goals.

Initially, users join a social-networking system 160 as individuals and do not attach to any particular community. They create linkages to friends who become part of their network, including companies, churches, charities, etc., and create social media networking pages. People also can create groups, like sports clubs, etc. that individuals can join or be invited to join. Depending on how the users set up their account, they can receive notifications when anything new is posted to that site. They are generally private but a user can make them public if desired. Companies, churches, charities, etc., create social media networking pages generally as a way to advertise. They might also choose to create a group that is more private. In one aspect, the social-networking system 160 creates specific groups to which users can or are subscribed. The linkages between the users are essentially created by the social-networking system 160 rather than by the users based on their choices. The social-networking system 160 has all the data associated with how users classify themselves, what they associate with, and how they think about sports, etc. The targeting tools provided by the social-networking system 160 may be used to reach out to specific users or groups of users based on demographics, likes, associations, etc. Finally, there are many social media pages/groups for specific sports and fitness. Everything from individual sports stars down to users who like football. In one aspect, the social-networking system 160 may be utilized for competition or as the engine to manage that process. Companies and clubs use the social-networking system 160 to drive users to their applications and their websites. Sports equipment companies build elements into their applications that allow users to compete with and challenge strangers or friends. In each case, a device agnostic application (e.g., Strava) or a hardware business that feeds their application. In one aspect, a mobile device application leverages the body-associated personal communicator 104 device agnostic hardware. Users use the device in simple to extreme ways from friendly banter about sitting too much to athletic competitions. Through device use, groups of users will become apparent and can be targeted and use that targeting to market the application and devices to similar users through the exhaustive database of information about what people like, do, buy, eat, support, etc., available from the social-networking system 160. The social-networking system 160 can leverage their game learning on rewards, progress towards goals, status upgrades, exclusive clubs, etc.

While various details have been set forth in the foregoing description, it will be appreciated that the various aspects of the personal authentication apparatus, system, and method may be practiced without these specific details. For example, for conciseness and clarity selected aspects have been shown in block diagram form rather than in detail. Some portions of the detailed descriptions provided herein may be presented in terms of instructions that operate on data that is stored in a computer memory. Such descriptions and representations are used by those skilled in the art to describe and convey the substance of their work to others skilled in the art. In general, an algorithm refers to a self-consistent sequence of steps leading to a desired result, where a "step" refers to a manipulation of physical quantities which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities.

Unless specifically stated otherwise as apparent from the foregoing discussion, it is appreciated that, throughout the foregoing description, discussions using terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

It is worthy to note that any reference to "one aspect," "an aspect," "one embodiment," or "an embodiment" means that a particular feature, structure, or characteristic described in connection with the aspect is included in at least one aspect. Thus, appearances of the phrases "in one aspect," "in an aspect," "in one embodiment," or "in an embodiment" in various places throughout the specification are not necessarily all referring to the same aspect. Furthermore, the particular features, structures or characteristics may be combined in any suitable manner in one or more aspects.

Some aspects may be described in accordance with the expression "coupled" and "connected" along with their derivatives. It should be understood that these terms are not intended as synonyms for each other. For example, some aspects may be described using the term "connected" to indicate that two or more elements are in direct physical or electrical contact with each other. In another example, some aspects may be described using the term "coupled" to indicate that two or more elements are in direct physical or electrical contact. The term "coupled," however, also may mean that two or more elements are not in direct contact with each other, but yet still co-operate or interact with each other.

It is worthy to note that any reference to "one aspect," "an aspect," "one embodiment," or "an embodiment" means that a particular feature, structure, or characteristic described in connection with the aspect is included in at least one aspect. Thus, appearances of the phrases "in one aspect," "in an aspect," "in one embodiment," or "in an embodiment" in various places throughout the specification are not necessarily all referring to the same aspect. Furthermore, the particular features, structures or characteristics may be combined in any suitable manner in one or more aspects.

Although various embodiments have been described herein, many modifications, variations, substitutions, changes, and equivalents to those embodiments may be implemented and will occur to those skilled in the art. Also, where materials are disclosed for certain components, other materials may be used. It is therefore to be understood that the foregoing description and the appended claims are intended to cover all such modifications and variations as falling within the scope of the disclosed embodiments. The following claims are intended to cover all such modification and variations.

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

All of the above-mentioned U.S. patents, U.S. patent application publications, U.S. patent applications, foreign patents, foreign patent applications, non-patent publications referred to in this specification and/or listed in any Application Data Sheet, or any other disclosure material are incorporated herein by reference, to the extent not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory).

A sale of a system or method may likewise occur in a territory even if components of the system or method are located and/or used outside the territory. Further, implementation of at least part of a system for performing a method in one territory does not preclude use of the system in another territory.

Although various embodiments have been described herein, many modifications, variations, substitutions, changes, and equivalents to those embodiments may be implemented and will occur to those skilled in the art. Also, where materials are disclosed for certain components, other materials may be used. It is therefore to be understood that the foregoing description and the appended claims are intended to cover all such modifications and variations as falling within the scope of the disclosed embodiments. The following claims are intended to cover all such modification and variations.

In summary, numerous benefits have been described which result from employing the concepts described herein. The foregoing description of the one or more embodiments has been presented for purposes of illustration and description. It is not intended to be exhaustive or limiting to the precise form disclosed. Modifications or variations are possible in light of the above teachings. The one or more embodiments were chosen and described in order to illustrate principles and practical application to thereby enable one of ordinary skill in the art to utilize the various embodiments and with various modifications as are suited to the particular use contemplated. It is intended that the claims submitted herewith define the overall scope.

The invention claimed is:

1. A social-networking system comprising:
a network addressable computing system configured to host an online social network, the computing system configured to receive, store, display, and transmit social network information from a body-associated client device, the social network information comprising physiologic or ingestion information, each of the physiologic or ingestion information obtained from the body-associated client device, the computing system comprising:
a processor coupled to a memory, the memory comprising machine executable instructions that when executed by the processor cause the processor to:
receive communications from one or more body-associated client devices, each communication including social network information identifying a user associated with one of the one or more body-associated client devices, the social network information obtained from each user by way of electrodes electrically coupled to a body of said user;
detect the physiologic information or ingestion information associated with each user, each of the physiologic information or ingestion information generated by an ingestible event marker ingested by said user;
associate each of the one or more body-associated client devices with a respective user account of one or more user accounts of the social-networking system, wherein each of the one or more user accounts correspond to a respective user of the social-networking system; and
generate a user profile of each user associated with the respective body-associated client device of the one or more body-associated client devices, each user profile comprising the physiologic information, if detected, or the ingestion information, if detected.

2. The social-networking system of claim 1, wherein the user profile is a first user profile, and wherein the online social network comprises a plurality of user profiles, wherein the plurality of user profiles comprises the first and a second user profile, wherein the social-networking system is configured to store relationship information between the first and second user profiles, and wherein the relationship information is based on the physiologic information, if detected, or the ingestion information, if detected.

3. The social-networking system of claim 1, further comprising an authorization server, wherein the authorization server is configured to provide each user with an option to choose whether actions associated with the physiologic or ingestion information are logged by the social-networking system.

4. The social-networking system of claim 1, wherein the social-networking system is configured to receive identification information of each user based on the physiologic or ingestion information and to provide access to each user based on the user identification information.

5. A method, comprising:
receiving, by a social-networking system, communications from one or more body-associated client devices, each communication including information identifying a user associated with one of the one or more body-associated client devices, the user identifying information comprising physiologic or ingestion information, each of the physiologic or ingestion information obtained from each user by way of electrodes electrically coupled to a body of said user;
detecting physiologic information or ingestion information associated with each user, each of the physiologic information or the ingestion information generated by an ingestible event marker ingested by said user;
associating each of the one or more body-associated client devices with a respective user account of one or more user accounts of the social-networking system, wherein each of the one or more user accounts correspond to a respective user of the social-networking system; and generating a user profile of each user associated with the respective body-associated client device of the one or more body-associated client devices, each user profile comprising at least one of the physiologic information, if detected, or the ingestion information, if detected.

6. The method of claim 5, further comprising generating a timeline for each user associated with the one or more body-associated client devices on the social-networking system based on the physiologic or ingestion information, wherein the timeline is at least one of a private timeline or a public timeline.

7. The method of claim 6, further comprising automatically updating the timeline based on additional physiologic or ingestion information received by the social-networking system from each of the one or more body-associated client devices associated with the respective user account of the one or more user accounts of the social-networking system.

8. The method of claim 5, further comprising providing at least one of rewards, awards, or incentives based on the physiologic or ingestion information to each user of the social-networking system associated with the respective body-associated client device of the one or more body-associated client devices.

9. The method of claim 5, further comprising providing an analytical framework based on the at least one of the physiologic or the ingestion information to authorized users of the social-networking system, wherein each of the authorized users is associated with the respective body-associated client device of the one or more body-associated client devices.

10. The method of claim 5, further comprising grouping based on the physiologic or ingestion information a plurality of users of the social-networking system, wherein each of the plurality of users is associated with the respective body-associated client device of the one or more body-associated client devices.

11. The method of claim 5, further comprising identifying at least a mentor or leader based on the physiologic or ingestion information from a plurality of users of the social-networking system, wherein each of the plurality of users is associated with the respective body-associated client device of the one or more body-associated client devices.

12. The method of claim 5, further comprising determining at least one of a mood or an emotional state based on the physiologic or ingestion information of each user of the social-networking system associated with the respective body-associated client device of the one or more body-associated client devices.

13. The method of claim 5, further comprising determining identification information of each user based on the physiologic or ingestion information received from each user of the social-networking system associated with the respective body-associated client device of the one or more body-associated client devices.

14. The method of claim 13, further comprising providing access to each user by the social-networking system based on the identification information.

15. The method of claim 5, wherein the physiologic information comprises at least one of information related to skin impedance, electro cardiogram signals, conductively transmitted current signals, position, temperature, heart rate, perspiration rate, humidity, altitude, pressure, global positioning system (GPS), proximity, bacteria levels, glucose level, chemical markers, or blood oxygen levels or the ingestion information of the user wherein the ingestion information comprises at least one of information associated with an event marker, a dose amount and type of medication ingested by each user of the social-networking system associated with the respective body-associated client device of the one or more body-associated client devices.

16. A receiver comprising:
a body-associated client device comprising:
one or more electrodes configured to be electrically coupled to a body of a user for detecting at least one of physiological or ingestion information, each of the physiologic information or ingestion information generated by an ingestible event marker ingested by the user, wherein the user is associated with the body-associated client device;
a processor coupled to a non-transitory memory and to the one or more electrodes, wherein the non-transitory memory comprises machine executable instructions that when executed by the processor, cause the processor to determine the identity of the user based on the at least one of physiological or ingestion information;
wherein:
the processor of the body-associated client device is configured to communicate the at least one of physiologic or ingestion information to a social-networking system comprising a network addressable computing system configured to host an online social network, the computing system configured to receive, store, display, and transmit the at least one of physiologic or ingestion information from the body-associated client device;
the computing system is configured to associate the body-associated client device with a user account of the social-networking system and to generate a user profile associated with the body-associated client device; and
the user profile comprises the at least one of physiologic or ingestion information.

17. The receiver of claim 16, wherein the processor of the body-associated client device is configured to receive physiologic information from the body of the user based on physical contact with the body of the user.

18. The receiver of claim 16, wherein the processor of the body-associated client device is configured to receive transbody conductive signals.

19. The receiver of claim 18, wherein the processor of the body-associated client device is configured to receive the transbody conductive signals from the ingestible event marker.

20. The receiver of claim 16, wherein the processor of the body-associated client device is configured to communicate the physiologic information to the social-networking system via wireless communication.

* * * * *